(12) United States Patent
Ganesan et al.

(10) Patent No.: US 7,977,304 B2
(45) Date of Patent: Jul. 12, 2011

(54) FK 228 DERIVATES AS HDAC INHIBITORS

(75) Inventors: Arasu Ganesan, Southampton (GB); Graham Keith Packham, Wiltshire (GB); Alexander Yurek-George, Berkshire (GB); Alexander Richard Liam Cecil, Southampton (GB)

(73) Assignee: University of Southampton Highfield, Southhampton (GB)

( * ) Notice: Subject to any disclaimer, the term of this patent is extended or adjusted under 35 U.S.C. 154(b) by 192 days.

(21) Appl. No.: 11/916,200

(22) PCT Filed: Jun. 2, 2006

(86) PCT No.: PCT/GB2006/002022
§ 371 (c)(1),
(2), (4) Date: Jun. 19, 2008

(87) PCT Pub. No.: WO2006/129105
PCT Pub. Date: Dec. 7, 2006

(65) Prior Publication Data
US 2009/0131390 A1     May 21, 2009

(30) Foreign Application Priority Data
Jun. 2, 2005   (GB) ................... 0511266.9

(51) Int. Cl.
A61K 38/12   (2006.01)
A61K 31/542  (2006.01)
C07K 11/00   (2006.01)
C07K 11/02   (2006.01)
C07K 7/54    (2006.01)

(52) U.S. Cl. .......... 514/1.1; 514/183; 530/317; 530/323
(58) Field of Classification Search .......... None
See application file for complete search history.

(56) References Cited

U.S. PATENT DOCUMENTS 4,977,138 A * 12/1990 Okuhara et al. .......... 514/10
5,798,097 A *  8/1998 McKenzie et al. ......... 424/181.1
2007/0190022 A1 * 8/2007 Bacopoulos et al. ....... 424/85.1

FOREIGN PATENT DOCUMENTS
EP        1 302 476 A1    4/2003
WO     WO 01/42282 A1    6/2001
WO     WO 2005/000332 A2  1/2005

OTHER PUBLICATIONS

Chuang D-M, Leng Y, Marinova Z, Kim H-J, Chiu C-T, "Multiple roles of HDAC inhibition in neurodegenerative conditions," Cell Press, 2009, 32(11): 591-601.*
Definition of isostere from http://dictionary.reference.com/browse/isostere, p. 1. Accessed Sep. 10, 2010.*
Dementia from Merck manual, pp. 1-17. Accessed Jul. 29, 2009.*
Mattson MP, "Pathways towards and away from Alzheimer's disease," Nature, 2004, 430: 631-639.*
Introduction to Cancer from Merck manual, p. 1. Accessed Mar. 5, 2008.*
Clinical Aspects of Cancer from Merck manual, pp. 1-4. Accessed Mar. 5, 2008.*
Auerbach R, Akhtar N, Lewis RL, Shinners BL, "Angiogenesis assays: Problems and pitfalls," Cancer and Metastasis Reviews, 2000, 19: 167-172.*
Gura T, "Systems for Identifying New Drugs Are Often Faulty," Science, 1997, 278: 1041-1042.*
Jain RK, "Barriers to drug delivery in solid tumors," Scientific American, 1994, 58-65.*
Yurek-George, Alexander et al. ((2004) "Total Synthesis of Spiruchostatin A, a Potent Histone Deacetylase Inhibitor" *J. Am. Chem. Soc.* 126(4):1030-1031.

* cited by examiner

*Primary Examiner* — Julie Ha
(74) *Attorney, Agent, or Firm* — Saliwanchik, Lloyd & Eisenschenk

(57) ABSTRACT

Compounds which are FK228 analogues of the general formula (I) or (I'), isosteres thereof and pharmaceutically acceptable salts thereof are found to inhibit HDAC wherein $R_1$, $R_2$, $R_3$ and $R_4$ are the same or different and represent an amino acid side chain moiety and each $R_6$ is the same or different and represents hydrogen or $C_1$-$C_4$ alkyl.

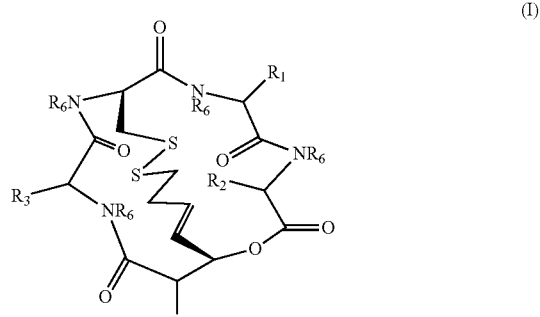

(I)

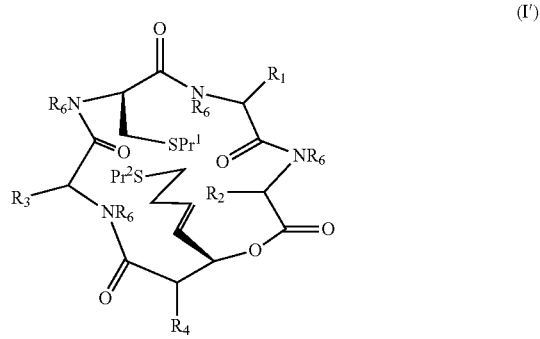

(I')

17 Claims, 4 Drawing Sheets

FK 228 DERIVATES AS HDAC INHIBITORS

This application is a National Stage Application of International Application Number PCT/GB2006/002022, filed Jun. 2, 2006; which claims priority to Great Britain Application No. 0511266.9, filed Jun. 2, 2005.

The present invention relates to specific depsipeptides which act as inhibitors of HDAC.

Histone deacetylases (HDACs) are zinc metalloenzymes that catalyse the hydrolysis of acetylated lysine residues. In histones, this returns lysines to their normal protonated state and is a global mechanism of eukaryotic transcriptional control, resulting in tight packaging of DNA in the nucleosome. Additionally, reversible lysine acetylation is an important regulatory process for non-histone proteins. Thus, compounds which are able to modulate HDAC have important therapeutic potential.

Two natural product depsipeptides, FK228 and Spiruchostatin A, have been reported to have potential as HDAC inhibitors. However, the possibilities for chemically modifying these natural products to provide additional analogues is extremely limited.

It has now surprisingly been found that compounds of the general formula (I) and (I') set out below act as inhibitors of HDAC. Accordingly, the present invention provides the use of a compound which is an FK228 analogue of formula (I) or (I'), an isostere thereof or a pharmaceutically acceptable salt thereof, in the manufacture of a medicament for use as an inhibitor of HDAC

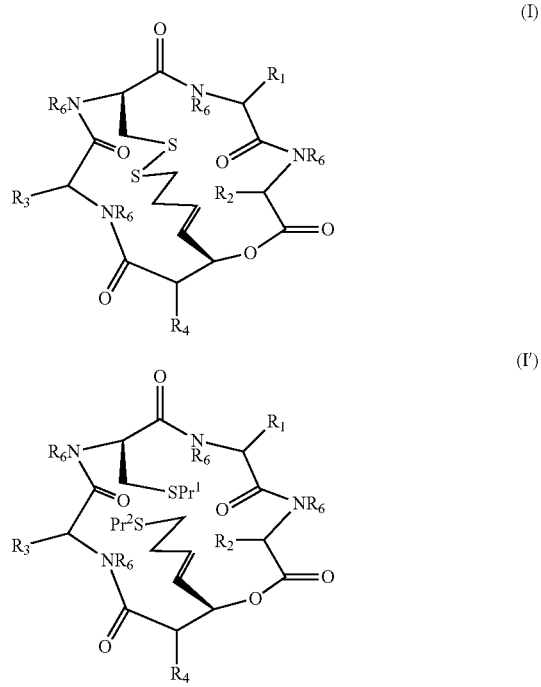

wherein $R_1$, $R_2$, $R_3$ and $R_4$ are the same or different and represent an amino acid side chain moiety, each $R_6$ is the same or different and represents hydrogen or $C_1$-$C_4$ alkyl, and $Pr^1$ and $Pr^2$ are the same or different and present hydrogen or a thiol-protecting group.

The present invention further provides the use of an FK228 analogue as defined above or a pharmaceutically acceptable salt thereof, in the manufacture of a medicament for use as an inhibitor of HDAC.

Results; Cell growth was inhibited by the compounds. Importantly, there were differences between the inhibitors and between cell types. The mean $IC_{50}$ for growth inhibition (±SD) was calculated from multiple experiments and are shown in Table 1 below.

Figure 2:
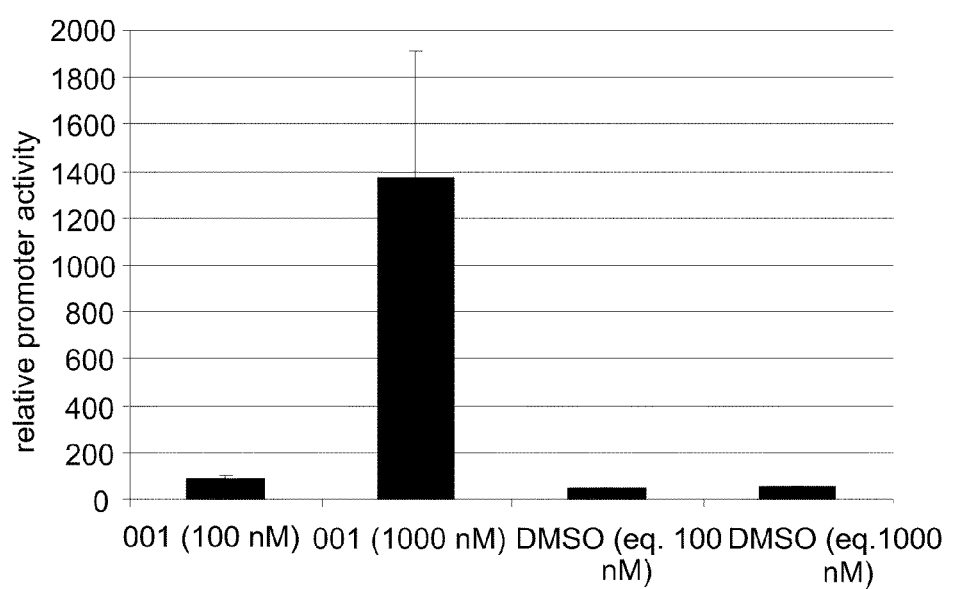

FIG. 2 shows the effect of compound 001 on the activity of the HDAC responsive SV40 promoter. MCF7 derived cells containing a stably integrated SV40 promoter-luciferase reporter plasmid were treated with the indicated concentrations of compound 001, or DMSO as a solvent control. Luciferase activity was determined after approx 16 hours. The data shown are derived from a single experiment performed in duplicate and are representative of multiple experiments.

Figure 3:
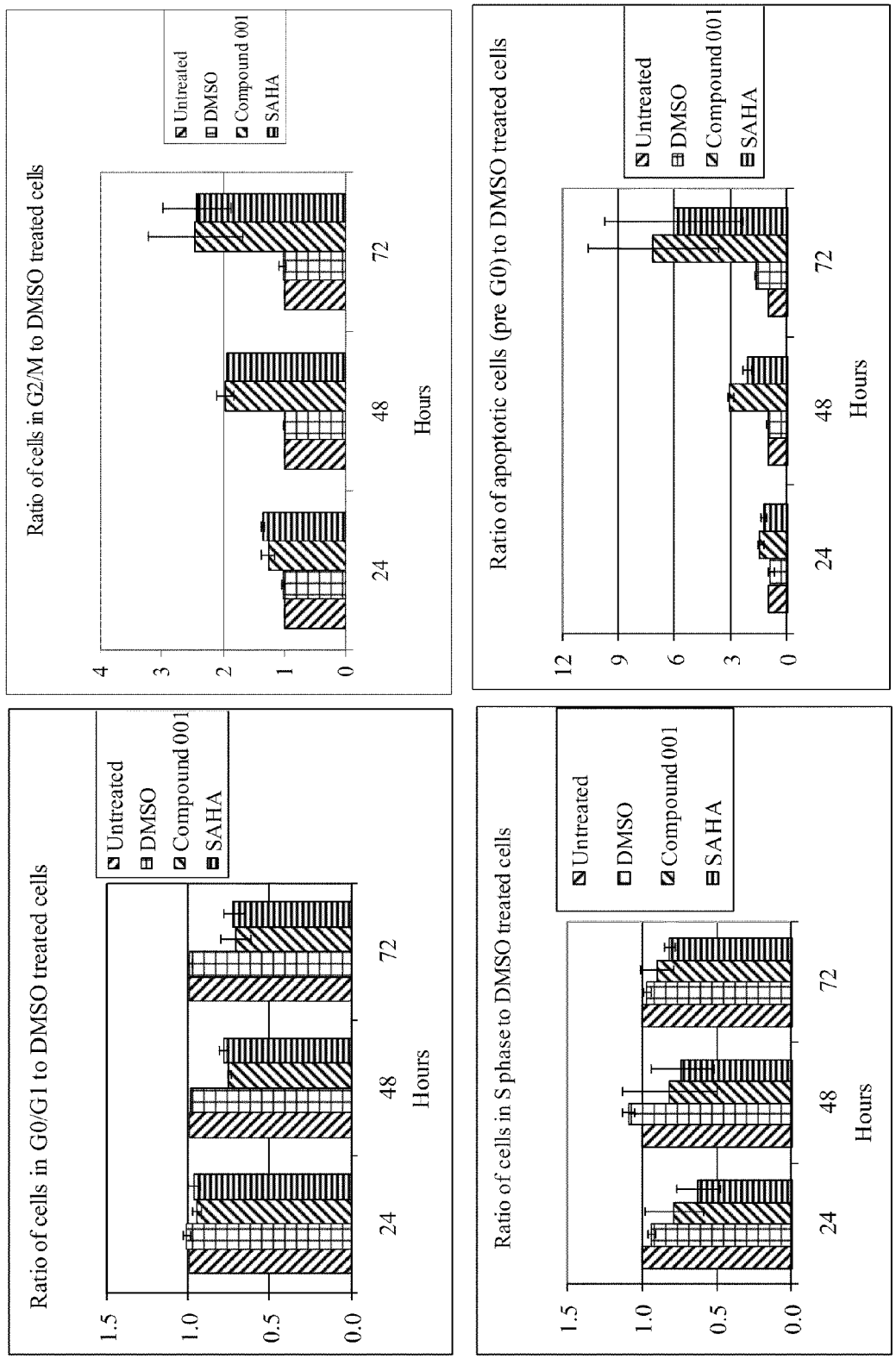

FIG. 3 shows the effects of compound 001 and SAHA on cell cycle distribution and survival in MCF7 cells. MCF7 cells were incubated with the indicated concentrations of compounds (each equivalent to ~10×$IC_{50}$ values for growth inhibition), or DMSO as a solvent control, for 24, 48 or 72 hours. The proportion of cells in different phases of the cell cycle was determined by flow cytometry. Data shown are mean values ±SD, derived from two separate experiments, relative to untreated cells which are normalised to 1.

Results; The figure shows that at equivalent effective concentrations, compound 001 and SAHA induce a predominant G2/M phase arrest and cell death in MCF7 cells.

Figure 4:
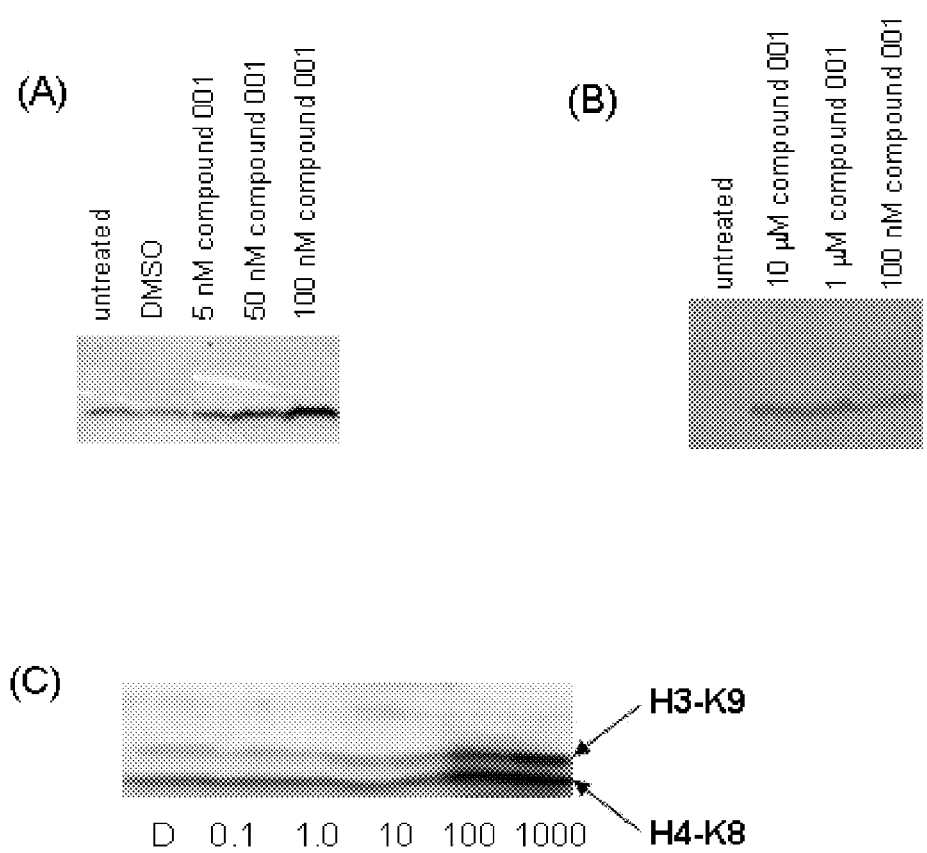

FIG. 4 shows the effect of compound 001 on Histone acetylation. (A) MCF7 cells were incubated with compound 001 for 24 hours. Histone H4 acetylation was measured by immunoblotting. (B) Cardiac myocytes were incubated with indicated compound 001 for 24 hours. Histone H4 acetylation was measured by immunoblotting. (C) MCF7 cells were incubated with compound 001 for 24 hours. Histone H3-K9 and Histone H4-K8 acetylation was measured by immunoblotting.

Results; The experiment shows that compound 001 induces the accumulation of acetylated histone H4 and specific Histone H3-K9 and Histone H4-K8 acetylation. We also demonstrated that Compound 001 increased the levels of acetylated histone H4 in primary chronic lymphocytic leukaemia cells (data not shown).

As used herein, the term "amino acid side chain moiety" refers to any amino acid side chain present in natural and unnatural amino acids. Examples of amino acid side chain moieties derived from unnatural amino acids, with the amino acids from which they are derived shown in brackets, are —$(CH_2)_2$—C(O)—O—C($CH_3)_3$ (tert-butoxycarbonylm-ethylanaline), —$(CH_2)_4$—NH—C(O)—O—C($CH_3)_3$ ($N_\epsilon$-(tert-butoxycarbonyl)-lysine), —$(CH_2)_3$—NH—C(O)$NH_2$ (citrulline), —$CH_2$—$CH_2$OH (homoserine) and —$(CH_2)_2$—$CH_2NH_2$ (ornithine). In particular —$(CH_2)_3$—NH—C(O)

NH$_2$ (citrulline), —CH$_2$—CH$_2$OH (homoserine) and —(CH$_2$)$_2$—CH$_2$NH$_2$ (ornithine) may be mentioned.

A C$_1$-C$_6$ alkyl group or moiety can be linear or branched. Typically, it is a C$_1$-C$_4$ alkyl group or moiety, for example methyl, ethyl, n-propyl, i-propyl, n-butyl, sec-butyl and t-butyl. Preferred examples include methyl, i-propyl and t-butyl.

A C$_2$-C$_6$ alkenyl group or moiety can be linear or branched. Typically, it is a C$_2$-C$_4$ alkenyl group or moiety. It is preferred that the alkenyl radicals are mono or diunsaturated, more preferably monounsaturated. Examples include vinyl, allyl, 1-propenyl, isopropenyl, 1-butenyl, 2-butenyl and 3-butenyl.

An alkylene group is a said alkyl group which is divalent.

A said thiol-protecting group is typically:

(a) a protecting group that forms a thioether to protect a thiol group, for example a benzyl group which is optionally substituted by C$_1$-C$_6$ alkoxy (for example methoxy), C$_1$-C$_6$ acyloxy (for example acetoxy), hydroxy and nitro, picolyl, picolyl-N-oxide, anthrylmethyl, diphenylmethyl, phenyl, t-butyl, adamanthyl, C$_1$-C$_6$ acyloxymethyl (for example pivaloyloxymethyl, tertiary butoxycarbonyloxymethyl);

(b) a protecting group that forms a monothio, dithio or aminothioacetal to protect a thiol group, for example C$_1$-C$_6$ alkoxymethyl (for example methoxymethyl, isobutoxymethyl), tetrahydropyranyl, benzylthiomethyl, phenylthiomethyl, thiazolidine, acetamidemethyl, benzamidomethyl;

(c) a protecting group that forms a thioester to protect a thiol group, such as tertiary butoxycarbonyl (BOC), acetyl and its derivatives, benzoyl and its derivatives; or (d) a protecting group that forms a carbamine acid thioester to protect a thiol group, such as carbamoyl, phenylcarbamoyl, C$_1$-C$_6$ alkylcarbamoyl (for example methylcarbamoyl and ethylcarbamoyl).

Typically, Pr$^1$ and Pr$^2$ are the same or different and each represent hydrogen or a protecting group that forms a thioether, a monothio, dithio or aminothioacetal, a thioester or a carbamine acid thioester to protect a thiol group. Preferably, Pr$^1$ and Pr$^2$ are the same or different and each represent hydrogen or a protecting group selected from a benzyl group which is optionally substituted by C$_1$-C$_6$ alkoxy (for example methoxy), C$_1$-C$_6$ acyloxy (for example acetoxy), hydroxy and nitro, picolyl, picolyl-N-oxide, anthrylmethyl, diphenylmethyl, phenyl, t-butyl, adamanthyl, C$_1$-C$_6$ acyloxymethyl (for example pivaloyloxymethyl, tertiary butoxycarbonyloxymethyl), C$_1$-C$_6$ alkoxymethyl (for example methoxymethyl, isobutoxymethyl), tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl and C$_1$-C$_6$ alkylcarbamoyl (for example methylcarbamoyl and ethylcarbamoyl). Most preferably, Pr$^1$ and Pr$^2$ are hydrogen.

In one embodiment, the amino acid side chain moieties are those derived from natural amino acids. Examples of amino acid side chain moieties derived from natural amino acids, with the amino acids from which they are derived shown in brackets, are —H (Glycine), —CH$_3$ (Alanine), —CH(CH$_3$)$_2$ (Valine), —CH$_2$CH(CH$_3$)$_2$ (Leucine), —CH(CH$_3$)CH$_2$CH$_3$ (Isoleucine), —(CH$_2$)$_4$NH$_2$ (Lysine), —(CH$_2$)$_3$NHC(=NH)NH$_2$ (Arginine), —CH$_2$-(5-1H-imidazolyl) (Histidine), —CH$_2$CONH$_2$ (Asparagine), —CH$_2$CH$_2$CONH$_2$ (Glutamine), —CH$_2$COOH (Aspartic acid), —CH$_2$CH$_2$COOH (Glutamic acid), —CH$_2$-phenyl (Phenylalanine), —CH$_2$-(4-OH-phenyl) (Tyrosine), —CH$_2$-(3-1H-indolyl) (Tryptophan), —CH$_2$SH (Cysteine), —CH$_2$CH$_2$SCH$_3$ (Methioine), —CH$_2$OH (Serine), and —CH(OH)CH$_3$ (Threonine).

In one embodiment, each amino acid side chain is an amino acid side chain moiety present in a natural amino acid or is —(CH$_2$)$_2$—C(O)—O—C(CH$_3$)$_3$ (tert-butoxycarbonylmethylanaline), —(CH$_2$)$_4$—NH—C(O)—O—C(CH$_3$)$_3$ (N$_\epsilon$-(tert-butoxycarbonyl)-lysine), —(CH$_2$)$_3$—NH—C(O)NH$_2$ (citrulline), —CH$_2$—CH$_2$OH (homoserine) or —(CH$_2$)$_2$—CH$_2$NH$_2$ (ornithine).

In a preferred embodiment of the invention, each amino acid side chain is a moiety selected from —H, —C$_1$-C$_6$ alkyl, —C$_2$-C$_6$ alkenyl, -L-O—C(O)—R', -L-C(O)—O—R", -L-A, -L-NR"R", -L-Het-C(O)-Het-R" and -L-Het-R", wherein L is a C$_1$-C$_6$ alkylene group, A is phenyl or a 5- to 6-membered heteroaryl group, each R' is the same or different and represents C$_1$-C$_4$ alkyl, each R" is the same or different and represents H or C$_1$-C$_6$ alkyl, each -Het- is the same or different and is a heteroatom spacer selected from —O—, —N(R''')— and —S— and each R''' is the same or different and represents H or C$_1$-C$_4$ alkyl.

When the group A is a 5 to 6 membered heteroaryl group, it may, for example, be furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazyl, pyrimidinyl, pyrazinyl, triazinyl. Typically, however, each A moiety is phenyl.

The hetero atom spacer group Het is typically —O— or —N(R''')—. More typically it is —O— or —N(H)—.

Preferably, each amino acid side chain is a moiety selected from —H, —C$_1$-C$_6$ alkyl, -L-C(O)—O—R", -L-A, -L-NR"R" and -L-N(R")—C(O)—O—R", wherein L, A and R" are as defined above.

Typically the amino side chain moieties of the compounds of the invention are selected from —(CH$_2$)$_2$—C(O)—O—C(CH$_3$)$_3$, —(CH$_2$)$_4$—NH—C(O)—O—C(CH$_3$)$_3$, —(CH$_2$)$_2$—C(O)OH, —CH$_2$—C$_6$H$_5$, —H, —CH$_3$, —CH(CH$_3$)$_2$, —CH$_2$CH(CH$_3$)$_2$, —CH(CH$_3$)CH$_2$CH$_3$, —(CH$_2$)$_4$NH$_2$, CH$_2$SH, —CH$_2$CH$_2$SCH$_3$, —CH$_2$OH and —CH(OH)CH$_3$. More typically the amino acid side chain moieties are selected from —H, —CH$_3$, —CH(CH$_3$)$_2$, —CH$_2$CH(CH$_3$)$_2$, —CH(CH$_3$)CH$_2$CH$_3$, —(CH$_2$)$_4$NH$_2$, CH$_2$SH, —CH$_2$CH$_2$SCH$_3$, —CH$_2$OH and —CH(OH)CH$_3$.

Preferably, the amino acid side chain moieties are selected from —H, —CH$_3$, —(CH$_2$)$_2$—C(O)—O—C(CH$_3$)$_3$, —(CH$_2$)$_4$—NH—C(O)—O—C(CH$_3$)$_3$, —(CH$_2$)$_2$—C(O)OH, —CH$_2$—C$_6$H$_5$, —(CH$_2$)$_4$NH$_2$ and —CH(CH$_3$)$_2$. In one embodiment of the invention, the amino acid side chain moieties are selected from —H, —CH$_3$ and —CH(CH$_3$)$_2$.

Typically, R$_1$ is an amino acid side chain moiety selected from —H, —C$_1$-C$_6$ alkyl, —C$_2$-C$_6$ alkenyl, -L-O—C(O)—R', -L-C(O)—O—R", -L-A, -L-NR"R", -L-Het-C(O)-Het-R" and -L-Het-R", wherein L, R', R", -Het- and R''' are as defined above. Preferably, R$_1$ is a moiety selected from —H, —C$_1$-C$_6$ alkyl, -L-C(O)—O—R", -L-A, -L-NR"R" and -L-N(R")—C(O)—O—R", wherein L, A and R" are as defined above. More preferably R$_1$ is a moiety selected from —H and —C$_1$-C$_6$ alkyl. More preferably still R$_1$ is —C$_1$-C$_4$ alkyl, in particular isopropyl.

Typically, R$_2$ is an amino acid side chain moiety selected from —H, —C$_1$-C$_6$ alkyl, —C$_2$-C$_6$ alkenyl, -L-O—C(O)—R', -L-C(O)—O—R", -L-A, -L-NR"R", -L-Het-C(O)-Het-R" and -L-Het-R", wherein L, R', R", -Het- and R''' are as defined above. Preferably, R$_2$ is a moiety selected from —H, —C$_1$-C$_6$ alkyl, -L-C(O)—O—R", -L-A, -L-NR"R" and -L-N(R")—C(O)—O—R", wherein L, A and R" are as defined above. More preferably R$_2$ is a moiety selected from —H and —C$_1$-C$_4$ alkyl. More preferably still R$_2$ is —H, —CH$_3$ or —CH(CH$_3$)$_2$. Even more preferably R$_2$ is —H or —CH$_3$.

Typically, $R_3$ is an amino acid side chain moiety selected from —H, —$C_1$-$C_6$ alkyl, —$C_2$-$C_6$ alkenyl, -L-O—C(O)—R', -L-C(O)—O—R'', -L-A, -L-NR''R''', -L-Het-C(O)-Het-R'' and -L-Het-R'', wherein L, R', R'', -Het- and R''' are as defined above. Preferably, $R_3$ is a moiety selected from —H, —$C_1$-$C_6$ alkyl, -L-C(O)—O—R'', -L-A, -L-NR''R'' and -L-N(R'')—C(O)—O—R'', wherein L, A and R'' are as defined above.

More preferably, $R_3$ is —$(CH_2)_2$—C(O)—O—$C(CH_3)_3$, —$(CH_2)_4$—NH—C(O)—O—$C(CH_3)_3$, —$(CH_2)_2$—C(O)OH, —$CH_2$—$C_6H_5$, —$CH_3$, —$CH(CH_3)_2$ or —$(CH_2)_4NH_2$.

Typically, $R_4$ is an amino acid side chain moiety selected from —H, —$C_1$-$C_6$ alkyl, —$C_2$-$C_6$ alkenyl, -L-O—C(O)—R', -L-C(O)—O—R'', -L-A, -L-NR''R''', -L-Het-C(O)-Het-R'' and -L-Het-R'', wherein L, R', R'', -Het- and R''' are as defined above. Preferably, $R_4$ is a moiety selected from —H, —$C_1$-$C_6$ alkyl, -L-C(O)—O—R'', -L-A, -L-NR''R'' and -L-N(R'')—C(O)—O—R'', wherein L, A and R'' are as defined above. More preferably, $R_4$ is hydrogen, —$C_1$-$C_6$ alkyl or —$C_2$-$C_6$ alkenyl. More preferably still, $R_4$ is hydrogen or —$C_1$-$C_4$ alkyl, more preferably hydrogen.

Typically, each $R_6$ is the same or different and is hydrogen or —$C_1$-$C_2$ alkyl. Preferably, each $R_6$ is hydrogen.

In one embodiment the present invention provides an FK228 analogue as defined above which is a compound of formula (I), an isostere thereof or a pharmaceutical acceptable salt thereof.

Preferred compounds of the invention are FK228 analogues as defined above wherein $R_1$ is selected from —H and —$C_1$-$C_6$ alkyl, $R_2$ is selected from —H and —$C_1$-$C_4$ alkyl, $R_3$ is selected from —H, —$C_1$-$C_6$ alkyl, -L-C(O)—O—R'', -L-A, -L-NR''R'' and -L-N(R'')—C(O)—O—R'' wherein L, A and R'' are as defined above, $R_4$ is selected from —H and —$C_1$-$C_6$ alkyl and each $R_6$ is the same or different and is hydrogen or —$C_1$-$C_2$ alkyl, isosteres thereof and pharmaceutically acceptable salts thereof.

Further preferred compounds of the invention are (a) compounds of formula (I) wherein $R_1$ is —$C_1$-$C_4$ alkyl, $R_2$ is selected from —H and —$CH_3$, $R_3$ is selected from —H, —$C_1$-$C_6$ alkyl, -L-C(O)—O—R'', -L-A, -L-NR''R'' and -L-N(R'')—C(O)—O—R'' wherein L, A and R'' are as defined above, $R_4$ is —H and each $R_6$ is —H, isosteres thereof and pharmaceutically acceptable salts thereof, and (b) compounds of formula (I') wherein $R_1$ is —$C_1$-$C_4$ alkyl, $R_2$ is selected from —H and —$CH_3$, $R_3$ is selected from —H, —$C_1$-$C_6$ alkyl, -L-C(O)—O—R'', -L-A, -L-NR''R'' and -L-N(R'')—C(O)—O—R'' wherein L, A and R'' are as defined above, $R_4$ is —H, each $R_6$ is —H and $Pr^1$ and $Pr^2$ are hydrogen, isosteres thereof and pharmaceutically acceptable salts thereof.

Further particularly preferred compounds of formula (I) are those wherein $R_1$ is —$CH(CH_3)_2$, $R_2$ is —$CH_3$, $R_3$ is —$CH_3$, $R_4$ is hydrogen and $R_6$ is —H;

$R_1$ is —$CH(CH_3)_2$, $R_2$ is —H, $R_3$ is —$(CH_2)_2$—C(O)—O—$C(CH_3)_3$, $R_4$ is hydrogen and $R_6$ is —H;

$R_1$ is —$CH(CH_3)_2$, $R_2$ is —H, $R_3$ is —$(CH_2)_2$—C(O)—OH, $R_4$ is hydrogen and $R_6$ is —H;

$R_1$ is —$CH(CH_3)_2$, $R_2$ is —H, $R_3$ is —$(CH_2)$—$C_6H_5$, $R_4$ is hydrogen and $R_6$ is —H;

$R_1$ is —$CH(CH_3)_2$, $R_2$ is —H, $R_3$ is —$CH(CH_3)_2$, $R_4$ is hydrogen and $R_6$ is —H;

$R_1$ is —$CH(CH_3)_2$, $R_2$ is —H, $R_3$ is —$(CH_2)_4$—NH—C(O)—O—$C(CH_3)_3$, $R_4$ is hydrogen and $R_6$ is —H; or $R_1$ is —$CH(CH_3)_2$, $R_2$ is —H, $R_3$ is —$(CH_2)_4$—$NH_2$, $R_4$ is hydrogen and $R_6$ is —H;

and pharmaceutically acceptable salts thereof.

Further particularly preferred compounds of formula (I') are those wherein $R_1$ is —$CH(CH_3)_2$, $R_2$ is —$CH_3$, $R_3$ is —$CH_3$, $R_4$ is hydrogen, $R_6$ is —H and $Pr^1$ and $Pr^2$ are hydrogen;

$R_1$ is —$CH(CH_3)_2$, $R_2$ is —H, $R_3$ is —$(CH_2)_2$—C(O)—O—$C(CH_3)_3$, $R_4$ is hydrogen, $R_6$ is —H and $Pr^1$ and $Pr^2$ are hydrogen;

$R_1$ is —$CH(CH_3)_2$, $R_2$ is —H, $R_3$ is —$(CH_2)_2$—C(O)—OH, $R_4$ is hydrogen, $R_6$ is —H and $Pr^1$ and $Pr^2$ are hydrogen;

$R_1$ is —$CH(CH_3)_2$, $R_2$ is —H, $R_3$ is —$(CH_2)$—$C_6H_5$, $R_4$ is hydrogen, $R_6$ is —H and $Pr^1$ and $Pr^2$ are hydrogen;

$R_1$ is —$CH(CH_3)_2$, $R_2$ is —H, $R_3$ is —$CH(CH_3)_2$, $R_4$ is hydrogen, $R_6$ is —H and $Pr^1$ and $Pr^2$ are hydrogen;

$R_1$ is —$CH(CH_3)_2$, $R_2$ is —H, $R_3$ is —$(CH_2)_4$—NH—C(O)—O—$C(CH_3)_3$, $R_4$ is hydrogen, $R_6$ is —H and $Pr^1$ and $Pr^2$ are hydrogen; or $R_1$ is —$CH(CH_3)_2$, $R_2$ is —H, $R_3$ is —$(CH_2)_4$—$NH_2$, $R_4$ is hydrogen, $R_6$ is —H and $Pr^1$ and $Pr^2$ are hydrogen;

and pharmaceutically acceptable salts thereof.

A preferred FK228 analogue is of formula (2) or (2')

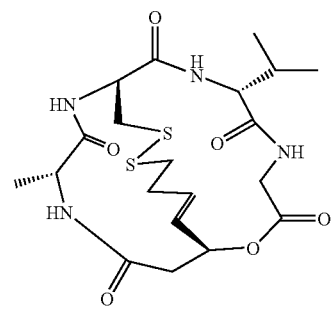

(2)

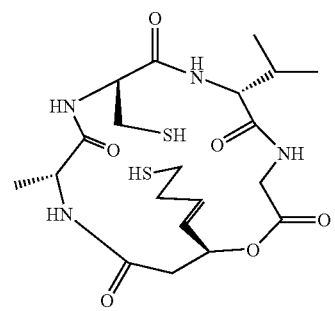

(2')

Another preferred FK228 analogue is of formula (3) or (3')

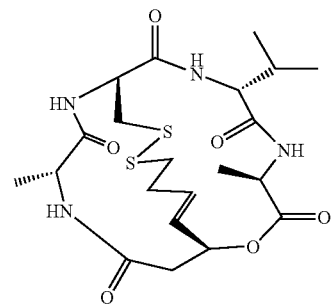

(3)

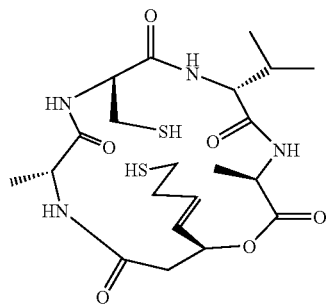
(3')
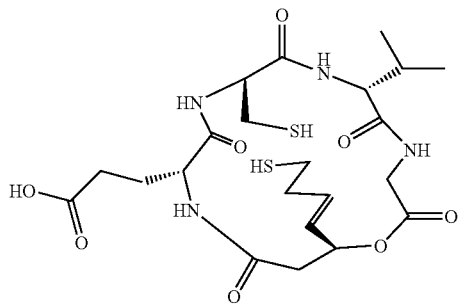
(5')
Another preferred FK228 analogue is of formula (4) or (4')
Another preferred FK228 analogue is of formula (6) or (6')
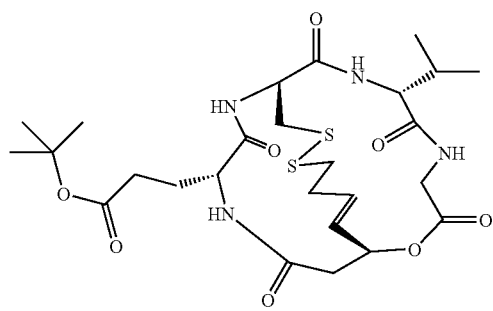
(4)
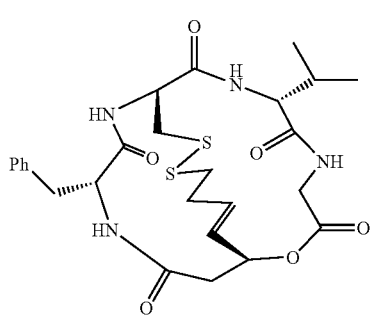
(6)
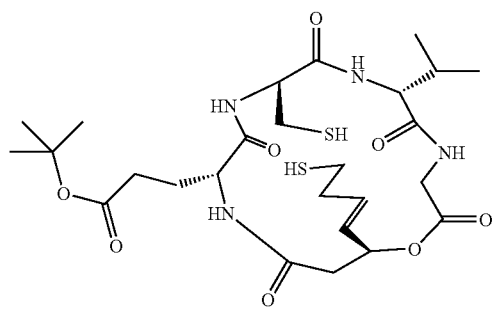
(4')
(6')
Another preferred FK228 analogue of formula (5) or (5')
Another preferred FK228 analogue is of formula (7) or (7')
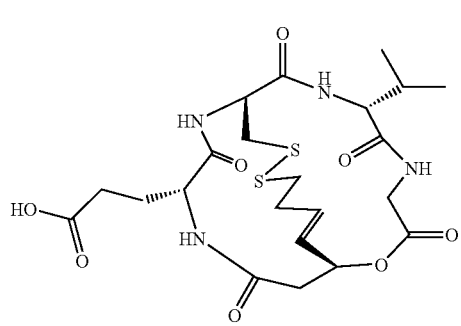
(5)
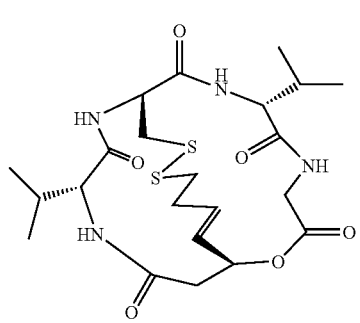
(7)

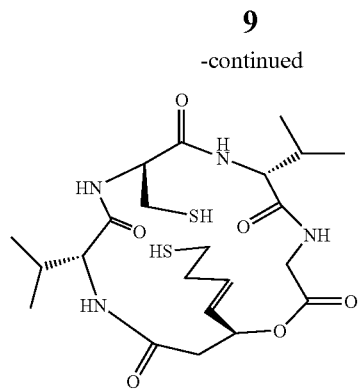
(7')
Another preferred FK228 analogue is of formula (8) or (8')
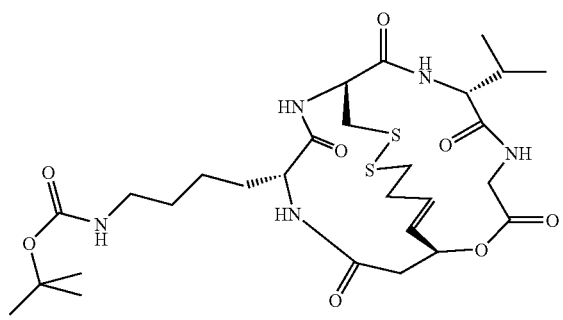
(8)
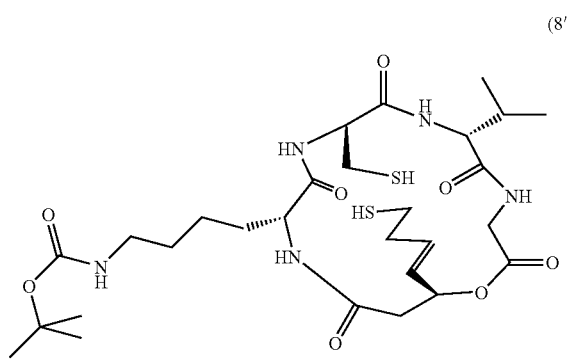
(8')
Another preferred FK228 analogue is of formula (9) or (9')
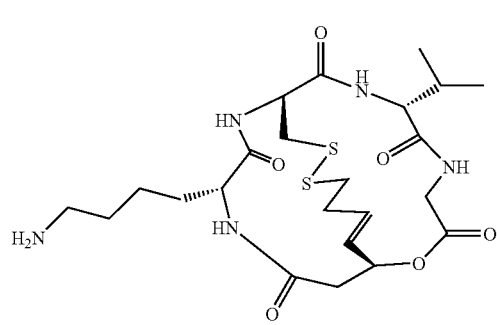
(9)
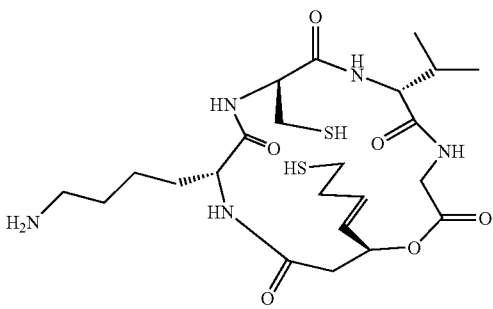
(9')
In one embodiment of the present invention, the FK228 analogues are of formula (II) or (II')
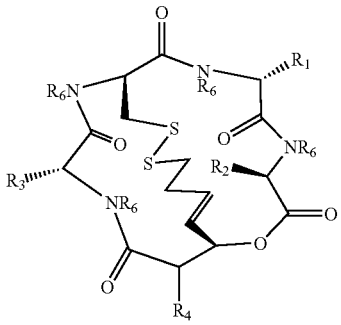
(II)
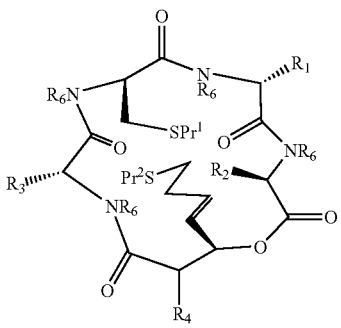
(II')
wherein $R_1$, $R_2$, $R_3$, $R_4$, $R_6$, $Pr^1$ and $Pr^2$ are as defined above.
In another embodiment of the present invention, the FK228 analogues are of formula (III) or (III')
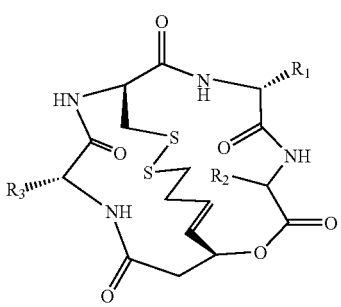
(III)

-continued (III')

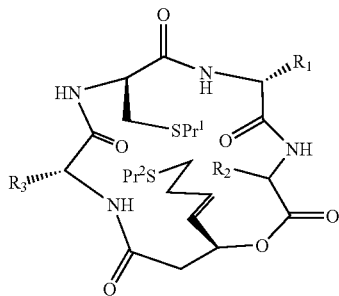

wherein $R_1$, $R_2$, $R_3$, $Pr^1$ and $Pr^2$ are as defined above.

In another embodiment of the present invention, the FK228 analogues are of formula (IV) or (IV')

(IV)

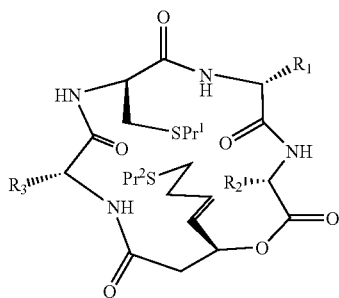

(IV')

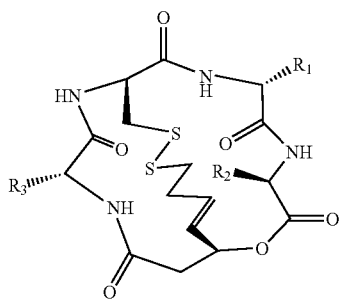

wherein $R_1$, $R_2$, $R_3$, $Pr^1$ and $Pr^2$ are as defined above.

In another embodiment of the present invention, the FK228 analogues are of formula (V) or (V')

(V)

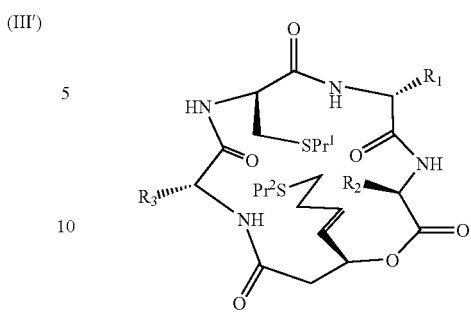

(V')

wherein $R_1$, $R_2$, $R_3$, $Pr^1$ and $Pr^2$ are as defined above.

In a further embodiment, the present invention provides the use of a compound of formula (VI), an isostere thereof or a pharmaceutically acceptable salt thereof, in the manufacture of a medicament for use as an inhibitor of HDAC (VI)

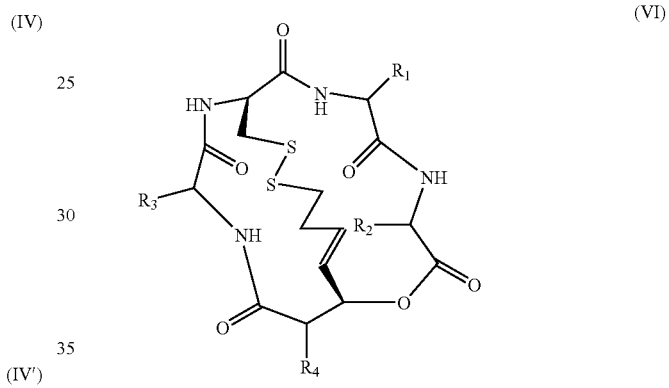

wherein $R_1$, $R_2$ and $R_3$ are the same or different and represent an amino acid side chain moiety and $R_4$ is hydrogen, $C_1$-$C_6$ alkyl or $C_2$-$C_6$ alkenyl.

Typically in this embodiment, $R_1$ is an amino acid side chain moiety derived from a natural amino acid. Preferably in this embodiment $R_1$ is —H, —$CH_3$, —$CH(CH_3)_2$, —$CH_2CH(CH_3)_2$, —$CH(CH_3)CH_2CH_3$, —$(CH_2)_4NH_2$, —$CH_2SH$, —$CH_2CH_2SCH_3$, —$CH_2OH$ or —$CH(OH)CH_3$. More preferably, $R_1$ is —H, —$CH_3$, —$CH(CH_3)_2$, —$CH_2CH(CH_3)_2$ or —$CH(CH_3)CH_2CH_3$. Most preferably, $R_1$ is —$CH(CH_3)_2$.

Typically in this embodiment, $R_2$ is an amino acid side chain moiety derived from a natural amino acid. Preferably $R_2$ is —H, —$CH_3$, —$CH(CH_3)_2$, —$CH_2CH(CH_3)_2$, —$CH(CH_3)CH_2CH_3$, —$(CH_2)_4NH_2$, —$CH_2SH$, —$CH_2CH_2SCH_3$, —$CH_2OH$ or —$CH(OH)CH_3$. More preferably, $R_2$ is —H, —$CH_3$ or —$CH(CH_3)_2$. Most preferably, $R_2$ is —H.

Typically in this embodiment, $R_3$ is an amino acid side chain moiety derived from a natural amino acid. Preferably $R_3$ is —H, —$CH_3$, —$CH(CH_3)_2$, —$CH_2CH(CH_3)_2$, —$CH(CH_3)CH_2CH_3$, —$(CH_2)_4NH_2$, —$CH_2SH$, —$CH_2CH_2SCH_3$, —$CH_2OH$ or —$CH(OH)CH_3$. More preferably, $R_3$ is —H, —$CH_3$, —$CH(CH_3)_2$, —$CH_2CH(CH_3)_2$ or —$CH(CH_3)CH_2CH_3$. Most preferably, $R_3$ is —$CH_3$.

Typically in this embodiment, $R_4$ is hydrogen or $C_1$-$C_6$ alkyl. Preferably, $R_4$ is hydrogen or $C_1$-$C_2$ alkyl. More preferably, $R_4$ is hydrogen.

In this embodiment preferred compounds of the invention are compounds of formula (VI) wherein:

R₁ is —H, —CH₃, —CH(CH₃)₂, —CH₂CH(CH₃)₂, —CH(CH₃)CH₂CH₃, —(CH₂)₄NH₂, —CH₂SH, —CH₂CH₂SCH₃, —CH₂OH or —CH(OH)CH₃;
R₂ is —H, —CH₃, —CH(CH₃)₂, —CH₂CH(CH₃)₂, —CH(CH₃)CH₂CH₃, —(CH₂)₄NH₂, —CH₂SH, —CH₂CH₂SCH₃, —CH₂OH or —CH(OH)CH₃;
R₃ is —H, —CH₃, —CH(CH₃)₂, —CH₂CH(CH₃)₂, —CH(CH₃)CH₂CH₃, —(CH₂)₄NH₂, —CH₂SH, —CH₂CH₂SCH₃, —CH₂OH or —CH(OH)CH₃; and
R₄ is hydrogen or C₁-C₂ alkyl.

In a preferred aspect of this embodiment the present invention provides compounds of formula (VI) wherein:
R₁ is —H, —CH₃, —CH(CH₃)₂, —CH₂CH(CH₃)₂ or —CH(CH₃)CH₂CH₃;
R₂ is —H, —CH₃ or —CH(CH₃)₂;
R₃ is —H, —CH₃, —CH(CH₃)₂, —CH₂CH(CH₃)₂ or —CH(CH₃)CH₂CH₃; and
R₄ is hydrogen.

Particularly preferred compounds of this embodiment are those of formula (VI) wherein R₁ is —CH(CH₃)₂, R₂ is —H, R₃ is —CH₃ and R₄ is hydrogen.

Further preferred compounds of this embodiment are compounds of formula (III)

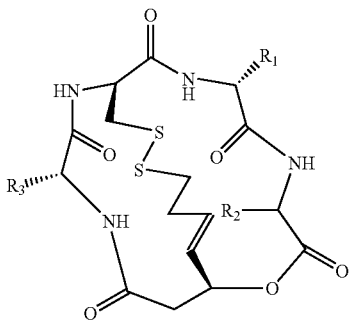

(III)

wherein R₁, R₂ and R₃ are as defined above.

Further more preferred compounds of this embodiment are compounds of formula (IV)

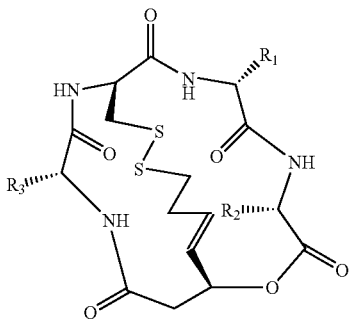

(IV)

wherein R₁, R₂ and R₃ are as defined above.

The compounds of the present invention are believed to be novel and the present invention thus provides for a compound of formula (I), an isostere thereof or a pharmaceutically acceptable salt thereof. The present invention further provides a compound of formula (I) or a pharmaceutically acceptable salt thereof.

The present invention also provides a compound of formula (I), an isostere thereof or a pharmaceutically acceptable salt thereof for use in a method of treating the human or animal body. The present invention further provides a compound of formula (I) or a pharmaceutically acceptable salt thereof for use in a method of treating the human or animal body.

The compounds of the present invention are particularly advantageous since they show high therapeutic effects. They are also advantageous since the tetrapeptide core can be readily synthesised.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines or heterocyclic amines.

As used herein, the term "isostere" refers to a compound resulting from the exchange of an atom or a group of atoms with another, broadly similar, atom or group of atoms. In the compounds of formula (I), the moieties which contain isosteric groups are preferably —NH—CHR₁—CO—, —NH—CHR₂—CO—O— and —NH—CO—CHR₃—NH—CO—. In the compounds of formula (I), the moieties which contain isosteric groups are more preferably —NH—CHR₁—CO— and —NH—CHR₂—CO—O—. Examples of such isosteres are compounds of formula (I) wherein the moiety —NH— has been replaced by —CH₂—, —O— or —S—, the moiety —CO— has been replaced by —CS— or —C(=NH)— and the moiety —O— has been replaced by —S—, CH₂— or —NH—.

The compounds of the present invention have the chirality shown in formula (I). However, the spatial positioning of the groups R₁, R₂ and R₃ can result in the formation of additional chiral centres in the compounds. For the avoidance of doubt, the chemical structures depicted herein are intended to embrace all of the stereoisomeric configurations associated with these additional chiral centres, including racemic and non-racemic mixtures and pure enantiomers and/or diastereoisomers.

For the avoidance of doubt, the present invention also embraces prodrugs which react in vivo to give a compound of the present invention or an isostere or pharmaceutically acceptable salt thereof.

Preferred compounds of the invention are optical isomers. Thus, for example, preferred compounds of formula (I) containing only one chiral centre include an R isomer in substantially pure form, an S enantiomer in substantially pure form and enantiomeric mixtures which contain an excess of the R enantiomer or an excess of the S enantiomer.

The present invention also provides a compound of formula (I), an isostere thereof or a pharmaceutically acceptable salt thereof and a pharmaceutically acceptable carrier or diluant.

Said pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions provided by the invention typically contain a compound of the invention which is a substantially pure optical isomer. Preferably, the pharmaceutical composition comprises a pharmaceutically acceptable salt of a compound of formula (I) or an isostere thereof.

The FK228 analogues may be prepared by conventional routes, for example using the following scheme wherein the groups $R_1$ to $R_4$ are as defined above:

a protected tetrapeptide. In step (d), the N-terminus of the tetrapeptide is deprotected, and the free amine is coupled with a β-hydroxy acid derivative wherein $R_5$ is a temporary blocking group which can be removed to produce a compound wherein $R_5$ is H, and X is a chiral auxiliary as reported in

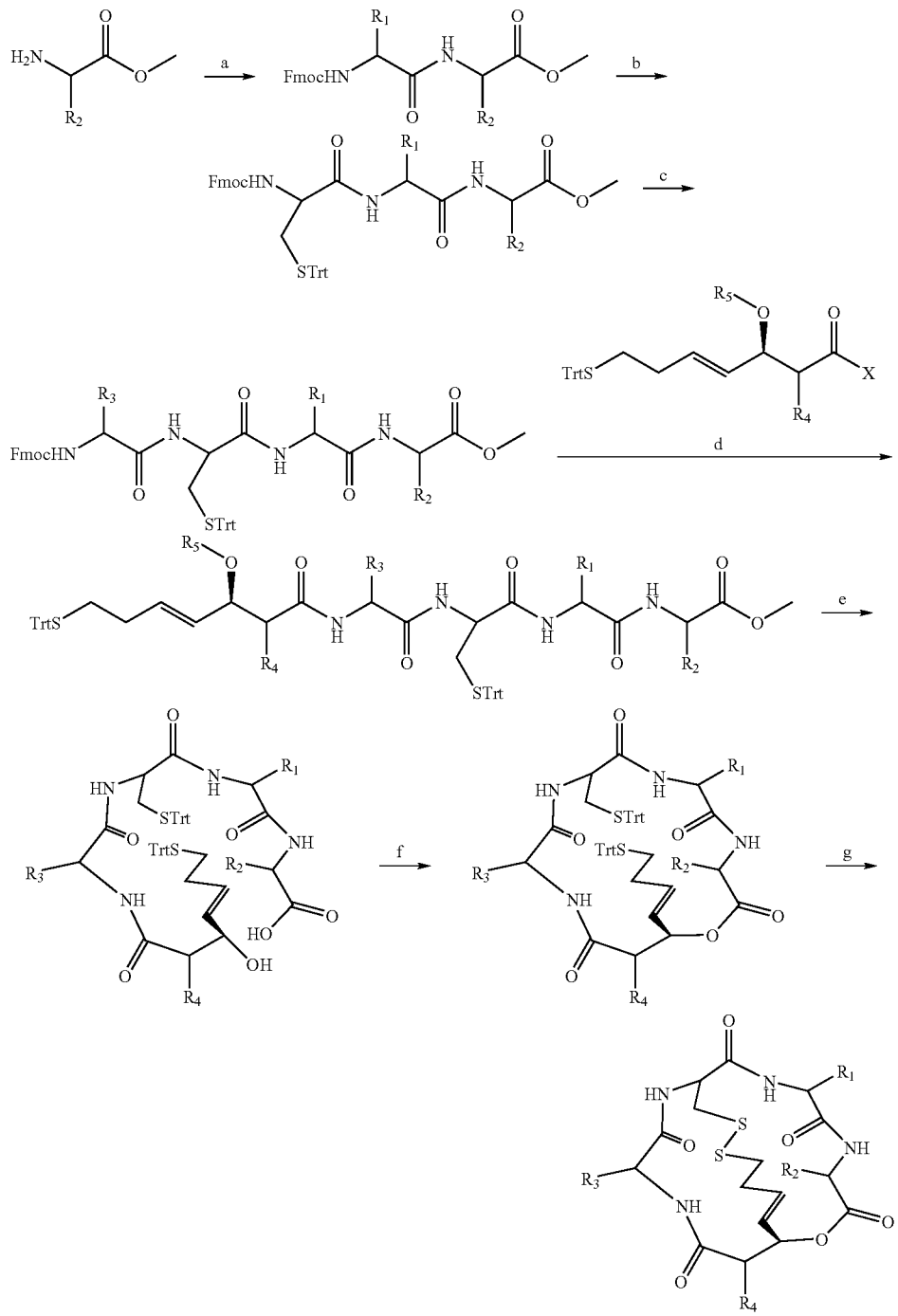

In step (a), an amino acid ester bearing the side-chain $R_2$ is condensed with a second amino acid bearing the side-chain $R_1$ to give a dipeptide. In step (b), the dipeptide is condensed with a protected cysteine derivative to give a tripeptide. In step (c) the tripeptide is coupled with an amino acid to provide Yurek-George, A.; Habens, F.; Brimmell, M.; Packham, G.; Ganesan, A. *J. Am. Chem. Soc.* 2004, 126, 1030-1031. In step (e), the ester group is hydrolysed, followed by cyclization in step (f) and disulfide bond formation in (g) to complete the synthesis of the bicyclic depsipeptide compounds (I).

Compounds of the invention in which $R_6$ is other than hydrogen can be obtained either by alkylating a corresponding compound of the invention or intermediate in which $R_6$ is hydrogen or by using appropriately substituted starting materials.

Compounds of formula (I') may be obtained by reaction of the product of step (g) above to cleave the disulfide bond. The cleavage of the disulfide bond is typically achieved using a thiol compound generally used for a reduction treatment of a protein having a disulfide bond, for example mercaptoethanol, thioglycol acid, 2-mercaptoethylamine, benzenethiol, parathiocresol and dithiothreitol. Preferably, mercaptoethanol and dithiothreitol are used. An excess thiol compound can be removed by for example dialysis or gel filtration. Alternatively, electrolysis, sodium tetrahydroborate, lithium aluminum hydride or sulfite may, for example, be used to cleave the disulfide bond.

Compounds of formula (I') in which $Pr^1$ and/or $Pr^2$ is other than hydrogen may be prepared by introducing a thiol-protecting group into a corresponding compound in which $Pr^1$ and/or $Pr^2$ is/are hydrogen. In this aspect a suitable agent for introducing thiol-protecting group to be used in this reaction is appropriately determined depending on the protecting group to be introduced. Examples include chlorides of the corresponding protecting group (for example benzyl chloride, methoxybenzyl chloride, acetoxybenzyl chloride, nitrobenzyl chloride, picolyl chloride, picolyl chloride-N-oxide, anthryl methyl chloride, isobutoxymethyl chloride, phenylthiomethyl chloride) and alcohols of the corresponding protecting group (for example diphenylmethyl alcohol, adamanthyl alcohol, acetamidemethyl alcohol, benzamidomethyl alcohol), dinitrophenyl, isobutylene, dimethoxymethane, dihydropyran and t-butyl chloroformate.

As the skilled person will appreciate, when one of $R_1$, $R_2$, $R_3$ and $R_4$ carries a functional group such as —OH, —SH, —$NH_2$ or —COOH, then it may be preferred for that group to be protected for one more of the reaction steps following its introduction. In this case the group in question could be protected in a separate step after its introduction, or, it could be protected already at the time it is introduced. The skilled person will be aware of suitable protecting groups that can be used in this regard.

The thus obtained FK228 analogues may be salified by treatment with an appropriate acid or base. Racemic mixtures obtained by any of the above processes can be resolved by standard techniques, for example elution on a chiral chromatography column.

Preferred compounds of the invention have an HDAC inhibitory activity which is at least equal to that exhibited by Suberoylanilide hydroxamic acid (SAHA). Thus, in a further embodiment, the present invention provides a process for selecting a compound which has an HDAC inhibitory activity which is at least equal to that exhibited by SAHA, which process comprises preparing a compound of formula (I) or (I') by:

(i) reacting a compound of formula (VI) with a compound of formula (VII)

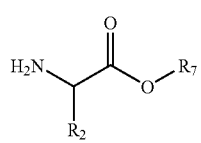
(VI)

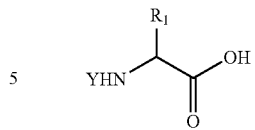
(VII)

wherein $R_1$ and $R_2$ are as defined above, $R_7$ is $C_1$-$C_4$ alkyl or $C_2$-$C_4$ alkenyl and Y is an amino protecting group;

(ii) deprotecting the thus obtained intermediate and reacting it with a compound of formula (VIII)

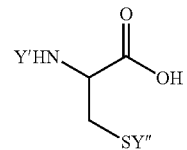
(VIII)

wherein Y' is an amino protecting group and Y" is hydrogen or a protecting group;

(iii) deprotecting the thus obtained intermediate and reacting it with a compound of formula (IX)

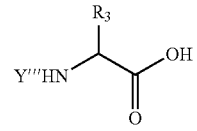
(IX)

wherein $R_3$ is as defined above and Y''' is an amino protecting group;

(iv) deprotecting the thus obtained intermediate and reacting it with a compound of formula (X)

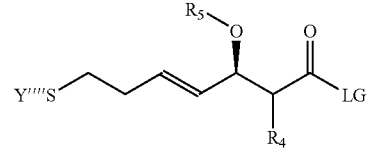
(X)

wherein $R_4$ is as defined above, $R_5$ is hydrogen or a hydroxy protecting group, LG is a leaving group and Y'''' is hydrogen or a protecting group;

(v) optionally deprotecting the β-hydroxy group on the thus obtained intermediate to remove the $R_5$ protecting group and replace it with H;

(vi) hydrolysing and cyclizing the thus obtained intermediate;

(vii) optionally reacting the thus obtained intermediate to effect disulfide bond formation, and, if a disulfide bond is formed, optionally cleaving the disulfide bond in the thus obtained compound, and if the thus obtained compound contains a thiol group, optionally introducing a thiol-protecting group; and (viii) screening the thus obtained compound to measure its activity as an HDAC inhibitor.

Typically, in step (vi), hydrolysis of the ester group is effected before cyclisation.

Typically in step (vii) DTT (dithiothreitol) is used to effect cleavage of the disulfide bond.

The person of skill in the art will appreciate that various identities may be used for the protecting groups Y, Y', Y", Y'" and Y"", and that the preferred identity will depend in each case on the nature of the particular groups present.

The groups Y, Y' and Y'" may, for example, be t-butoxycarbonyl (Boc) or 9-fluorenylmethoxycarbonyl (Fmoc). Typically, they are Fmoc.

The groups Y" and Y"" may, for example, be trityl (Trt).

The skilled person will be aware of suitable identities for the leaving group LG. It may, for example, be a chiral auxiliary, such as a thiazolidinethione group attached via its N atom, as explained in Yurek-George, A. et al (*J. Am. Chem. Soc.* 2004, 126, 1030-1031). Alternatively, it may be a —OH group.

The group $R_7$ is typically a $C_1$-$C_4$ alkyl or $C_1$-$C_4$ alkenyl group. More typically it is methyl or allyl.

The skilled person will appreciate that various assays are suitable for testing for HDAC inhibition and may be used to measure the activity of a compound obtained from step (vii) compared to that of the known HDAC inhibitor SAHA. Thus, the $IC_{50}$ of a test compound against HDAC can, for example, be determined in an in vitro assay, and compared with the $IC_{50}$ of SAHA under the same assay conditions. If a test compound has an $IC_{50}$ value equal to or lower than that of SAHA it should be understood as having an HDAC inhibitory activity which is at least equal to that exhibited by SAHA.

In a preferred embodiment the present invention provides a process for selecting a compound which has an HDAC inhibitory activity which is at least equal to that exhibited by SAHA as defined above, wherein in step (viii) the screening step is an in vitro HDAC assay. Typically, said assay comprises contacting a test compound and SAHA, at various concentrations, with diluted Hela Nuclear Extract to determine the $IC_{50}$ of the test compound and of SAHA against Hela Nuclear Extract. A test compound which has an $IC_{50}$ value measured against Hela Nuclear Extract which is equal to, or lower than, the $IC_{50}$ of SAHA under the same assay conditions should be understood as having an inhibitory activity which is at least equal to that exhibited by SAHA. Typically said assay is performed using a HDAC fluorescent activity assay kit (Biomol, UK) and the test compounds are reduced prior to analysis. Said assay test may, for example, be performed as described below under the heading "Activity Assay 5".

In another embodiment the present invention provides a process for selecting a compound which has a human cancer cell growth inhibitory activity which is at least equal to that exhibited by SAHA, which process comprises preparing a compound of formula (I) or (I') via steps (i) to (vii) as defined above followed by (viii) screening the thus obtained compound to measure its activity as a human cancer cell growth inhibitor.

The skilled person will appreciate that various assays are suitable for testing for human cancer cell growth inhibition and may be used to measure the activity of a compound obtained from step (vii) compared to that of SAHA. Thus, the $IC_{50}$ of a test compound against human cancer cell growth can, for example, be determined in an in vitro assay, and compared with the $IC_{50}$ of SAHA under the same assay conditions. If a test compound has an $IC_{50}$ value equal to or lower than that of SAHA it should be understood as having an inhibitory activity which is at least equal to that exhibited by SAHA. Typically in this embodiment step (viii) comprises an in vitro assay which comprises contacting a test compound and SAHA, at various concentrations, with an MCF7 breast, HUT78 T-cell leukaemia, A2780 ovarian, PC3 or LNCAP prostate cancer cell line to determine the $IC_{50}$ of the test compound and of SAHA against the cell line. A test compound which has an $IC_{50}$ value measured against any of these cell lines which is equal to, or lower than, the $IC_{50}$ of SAHA under the same assay conditions should be understood as having an inhibitory activity at least equal to that of SAHA. Typically in this embodiment, said assay is performed using the CyQuant™ assay system (Molecular Probes, Inc. USA). Said assay test may, for example, be performed as described below under the headings "Activity Assay 6" and/or "Activity Assay 1".

In another preferred embodiment the present invention provides a process for selecting a compound which has an anti-inflammatory activity which is at least equal to that exhibited by SAHA, which process comprises preparing a compound of formula (I) or (I') via steps (i) to (vii) as defined above followed by (viii) screening the thus obtained compound to measure its anti-inflammatory activity.

The skilled person will appreciate that various assays are suitable for assessing the anti-inflammatory activity of a compound. The anti-inflammatory activity of a test compound relative to SAHA may, for example, be determined by measuring the activity of a compound in inhibiting the production of TNFα from peripheral blood mononuclear cells (PBMCs) relative to SAHA. Thus, the ability of a test compound to inhibit the production of TNFα from PBMCs can, for example, be deteimined in an assay, and compared with the activity of SAHA under the same assay conditions. If a test compound has an in vitro inhibitory activity of TNFα production which is equal to or higher than that of SAHA under the same assay conditions it should be understood as having an anti-inflammatory activity which is at least equal to that exhibited by SAHA. Typically step (viii) is performed using the QUANTIKINE® Human-α assay kit (R&D systems, Abingdon UK). Said assay test may, for example, be performed as described below under the heading "Activity Assay 7".

In another aspect of this embodiment, the anti-inflammatory activity of a test compound relative to SAHA may be determined by assessing the activity of a compound in inhibiting inflammation in Balb/c mice relative to SAHA. If a test compound has an in vivo inhibitory activity which is equal to or higher than that of SAHA under the same test conditions it should be understood as having an anti-inflammatory activity which is at least equal to that exhibited by SAHA. Typically, in this embodiment step (viii) is performed by assessing the in vivo activity of a test compound and of SAHA in inhibiting inflammation in Balb/c mice induced by a chemical challenge. Typically, said chemical challenge involves the topical administration to the mice of oxalazone or acetone. In this embodiment, the compounds under investigation may be applied before or after the chemical challenge. Assessment of anti-inflammatory activity along such lines may, for example, be performed as described below under the heading "Activity Assay 8".

In another preferred embodiment the present invention provides a process for selecting a compound which has an activity in inducing a predominant G2/M phase arrest or cell death in MCF7 cells which is at least equal to that exhibited by SAHA, which process comprises preparing a compound of formula (I) or (I') via steps (i) to (vii) as defined above followed by (viii) screening the thus obtained compound to measure activity in inducing a predominant G2/M phase arrest or cell death in MCF7 cells relative to SAHA. Screening step (viii) may, for example, comprise an assay performed as described below under the heading "Activity Assay 3".

In the screening steps described above, the preferred form of the test compound depends on the nature of the screening step. Thus, if the screening step is an in vitro assay such as that described below under "Assay Activity 5", the test compound is preferably of formula (I') as defined above. If, however, the screening step is against a cell line, then the test compound is preferably of the formula (I).

The compounds of the present invention are found to be inhibitors of HDAC. The compounds of the present invention are therefore therapeutically useful.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

One preferred route of administration is inhalation. The major advantages of inhaled medications are their direct delivery to the area of rich blood supply in comparison to many medications taken by oral route. Thus, the absorption is very rapid as the alveoli have an enormous surface area and rich blood supply and first pass metabolism is bypassed.

Preferred pharmaceutical compositions of the invention therefore include those suitable for inhalation. The present invention also provides an inhalation device containing such a pharmaceutical composition. Typically said device is a metered dose inhaler (MDI), which contains a pharmaceutically acceptable chemical propellant to push the medication out of the inhaler. Typically, said propellant is a fluorocarbon.

Further preferred inhalation devices include nebulizers. Nebulizers are devices capable of delivering fine liquid mists of medication through a "mask" that fits over the nose and mouth, using air or oxygen under pressure. They are frequently used to treat those with asthma who cannot use an inhaler, including infants, young children and acutely ill patients of all ages.

Said inhalation device can also be, for example, a rotary inhaler or a dry powder inhaler, capable of delivering a compound of the invention without a propellant.

Typically, said inhalation device contains a spacer. A spacer is a device which enables individuals to inhale a greater amount of medication directly into the lower airways, where it is intended to go, rather than into the throat. Many spacers fit on the end of an inhaler; for some, the canister of medication fits into the device. Spacers with holding chambers and one-way valves prevent medication from escaping into the air. Many people, especially young children and the elderly, may have difficulties coordinating their inhalation with the action necessary to trigger a puff from a metered dose inhaler. For these patients, use of a spacer is particularly recommended.

Another preferred route of administration is intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. Drugs can be delivered nasally in smaller doses than medication delivered in tablet form. By this method absorption is very rapid and first pass metabolism is bypassed, thus reducing inter-patient variability. Nasal delivery devices further allow medication to be administered in precise, metered doses. Thus, the pharmaceutical compositions of the invention are typically suitable for intranasal administration. Further, the present invention also provides an intranasal device containing such a pharmaceutical composition.

A further preferred route of administration is transdermal administration. The present invention therefore also provides a transdermal patch containing a compound of the invention, or a pharmaceutically acceptable salt thereof. Also preferred is sublingual administration. The present invention therefore also provides a sub-lingual tablet comprising a compound of the invention or a pharmaceutically acceptable salt thereof.

A compound of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention are therapeutically useful in the treatment or prevention of conditions mediated by HDAC. Accordingly, the present invention provides the use of a compound of the formula (I), or a pharmaceutically acceptable salt thereof, in the manufacture of a medicament for use in the treatment or prevention of a condition mediated by HDAC. Also provided is a method of treating a patient suffering from or susceptible to a condition mediated by HDAC, which method comprises administering to said patient an effective amount of a compound of formula (I), an isostere thereof or a pharmaceutically acceptable salt thereof.

In one embodiment the compounds of the present invention may be used in combination with another known inhibitor of HDAC, such as SAHA. In this embodiment, the combination product may be formulated such that it comprises each of the medicaments for simultaneous, separate or sequential use.

The present invention therefore provides a product comprising (a) an FK228 analogue of the invention as defined above or an isostere or pharmaceutically acceptable salt thereof; and (b) another known inhibitor of HDAC, such as SAHA, for simultaneous, separate or sequential use.

The present invention therefore also provides the use of an FK228 analogue of the invention as defined above or an isostere or pharmaceutically acceptable salt thereof for use in the manufacture of a medicament for use in co-administration with another known inhibitor of HDAC, such as SAHA.

The skilled person will be aware of other known inhibitors of HDAC. US20040266769, for example, gives suitable examples. Examples include spiruchostatin A, FR-901228, trichostatin A and SAHA.

The compounds of the present invention can be used in both the treatment and prevention of cancer and can be used in a monotherapy or in a combination therapy. When used in a combination therapy, the compounds of the present invention are typically used together with small chemical compounds, radiation, antibody-based therapies (for example herceptin and rituximab), anti-cancer vaccination, gene therapy, cellular therapies, hormone therapies or cytokine therapy.

In a preferred embodiment of the invention a compound of the invention is used in combination with another chemotherapeutic or antineoplastic agent in the treatment of a cancer. Examples of such other chemotherapeutic or antineoplastic agents include mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN 38 and DNA methylation inhibitors for example the DNA methylation inhibitors disclosed in WO 02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of an FK228 analogue as defined above or an isostere thereof or a pharmaceutically acceptable salt thereof in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

HDAC is believed to contribute to the pathology and/or symptomology of several different diseases such that reduction of the activity of HDAC in a subject through inhibition may be used to therapeutically address these disease states. Examples of various diseases that may be treated using the HDAC inhibitors of the present invention are described herein. It is noted that additional diseases beyond those disclosed herein may be later identified as the biological roles that HDAC play in various pathways becomes more fully understood.

One set of indications that HDAC inhibitors of the present invention may be used to treat are those involving undesirable or uncontrolled cell proliferation. Such indications include benign tumors, various types of cancers such as primary tumors and tumor metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta.-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-(2-carboxyphenyl-4-chloroanthronilic acid disodium or "CCA", thalidomide; angostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumors retain their differentiated features and do not divide in a completely uncontrolled manner. A benign tumor is usually localized and nonmetastatic. Specific types of benign tumors that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumors, or metastases, are tumors that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumors, either primary or secondary, that can be treated using the HDAC inhibitors of the present invention include, but are not limited to, leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome. An example of a cell proliferative disorder that may be treated using the invention is a bone tumor.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularization and corneal neovascularization. Examples of retinal/choroidal neovascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, *Mycobacteria* infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulomas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angionesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischaemic heart disease, angina, arrythmias, hypercholesteremia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including *plasmodium, cryptosporidium parvum, toxoplasma gondii, sarcocystis neurona* and *Eimeria* sp.)

The compounds of the present invention are particularly suitable for the treatment of undesirable or uncontrolled cell proliferation, preferably for the treatment of benign tumours/hyperplasias and malignant tumors, more preferably for the treatment of malignant tumors and most preferably for the treatment of CCL, breast cancer and T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes, osteoporosis, MDS, benign prostatic hyperplasia, oral leukoplakia, a genetically related metabolic disorder, an infection, Rubens-Taybi, fragile X syndrome, or alpha-1 antitrypsin deficiency, or to accelerate wound healing, to protect hair follicles or as an immunosuppressant.

Typically, said inflammatory condition is a skin inflammatory condition (for example psoriasis, acne and eczema), asthma, chronic obstructive pulmonary disease (COPD), rheumatoid arthritis (RA), inflammatory bowel disease (IBD), Crohn's disease or colitis.

Typically, said cancer is chronic lymphocytic leukaemia, breast cancer, prostate cancer, ovarian cancer, mesothelioma or T-cell lymphoma.

Typically, said cardiovascular disease is hypertension, myocardial infarction (MI), ischemic heart disease (IHD) (reperfusion), angina pectoris, arrhythmia, hypercholesteremia, hyperlipidaemia, atherosclerosis, stroke, myocarditis, congestive heart failure, primary and secondary ie dilated (congestive) cardiomyopathy, hypertrophic cardiomyopathy, restrictive cardiomyopathy, peripheral vascular disease, tachycardia, high blood pressure or thrombosis.

Typically, said genetically related metabolic disorder is cystic fibrosis (CF), peroxisome biogenesis disorder or adrenoleukodystrophy.

Typically, the compounds of the invention are used as an immunosuppressant following organ transplant.

Typically, said infection is a viral, bacterial, fungal or parasitic infection, in particular an infection by *S aureus, P acne, candida* or *aspergillus*.

Typically, said CNS disorder is Huntingdon's disease, Alzheimer's disease, multiple sclerosis or amyotrophic lateral sclerosis.

Preferably, in this embodiment, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

Most preferably, the compounds of the invention are used to alleviate chronic lymphocytic leukaemia, breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

A therapeutically effective amount of a compound of the invention is administered to a patient. A typical dose is from about 0.001 to 50 mg per kg of body weight, according to the activity of the specific compound, the age, weight and conditions of the subject to be treated, the type and severity of the disease and the frequency and route of administration. Preferably, daily dosage levels are from 5 mg to 2 g.

The following Examples illustrate the invention. They do not, however, limit the invention in any way. In this regard, it is important to understand that the particular assays used in the Examples section are designed only to provide an indication of activity in inhibiting HDAC. There are many assays available to determine the activity of given compounds as HDAC antagonists, and a negative result in any one particular assay is therefore not determinative.

EXAMPLES
(E)-(1S,7R,10S,21R)-7-Isopropyl-21-methyl-2-oxa-12,13-dithia-5,8,20,23-tetraaza-bicyclo[8.7.6]tricos-16-ene-3,6,9,19,22-pentaone, hereinafter referred to as compound 001, was prepared using the scheme shown below:
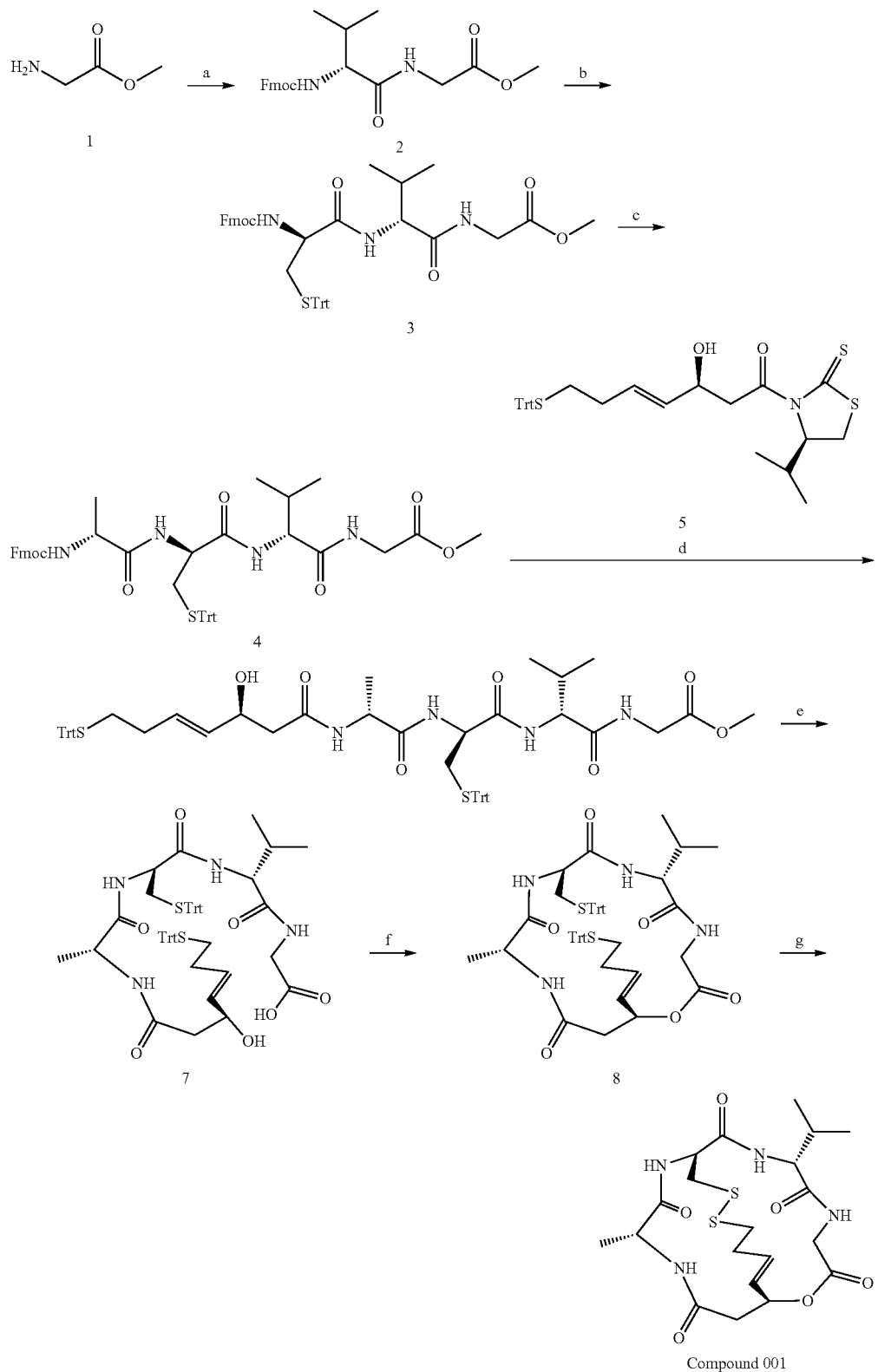
Compound 001

Preparation of [(R)-2-(9H-Fluoren-9-ylmethoxycarbonylamino)-3-methyl-butyrylamino]-acetic acid methyl ester (2)

To a stirred solution of Fmoc protected D-valine (2.70 g, 7.96 mmol) in CH$_2$Cl$_2$ (50 mL) was added EDAC.HCl (1.83 g, 9.55 mmol), HOBt (1.30 g, 9.55 mmol) and DIEA (3.8 mL, 27.86 mmol). After stirring at rt for 15 minutes, glycine methyl ester (1, 1.0 g, 7.96 mmol) was then added and the reaction mixture stirred for 4 h, diluted with CH$_2$Cl$_2$ (50 mL) washed with water (25 mL), 10% HCl (25 mL), 5% NaHCO$_3$ (25 mL) and sat NaCl (25 mL) solutions, dried (Na$_2$SO$_4$), filtered, and concentrated to give an off white solid which was re-crystallised from CH$_3$CN to give 2 as a white solid (2.81 g, 86%): mp=148-150° C.; [α]$^{22}_D$ −7.32 (c 0.50, CHCl$_3$); [α]$^{22}_D$ −7.32 (c 0.50, CHCl$_3$); IR $\nu_{max}$ 3287, 1750, 1690, 1649, 1535 cm$^{-1}$; $^1$H NMR 400 MHz 7.75 (d, J=7.5 Hz, 2H), 7.57 (d, J=7.0 Hz, 2H), 7.39 (t, J=7.0 Hz, 2H), 7.28 (m, 2H), 6.54 (s, 1H), 5.44 (s, 1H), 7.43-4.38 (m, 2H), 4.21 (t, J=7.0 Hz, 1H), 4.01-3.96 (m, 3H) 3.72 (s, 3H), 2.16 (m, 1H), 0.96 (t, J=9.0 Hz, 6H); $^{13}$C NMR 100 MHz 171.7 (C), 170.1 (C), 156.6 (C), 143.9 (C), 141.4 (C), 127.8 (CH), 127.2 (CH), 125.2 (CH), 120.1 (CH), 67.2 (CH$_2$), 60.4 (CH), 52.5 (CH), 47.3 (CH$_3$), 41.2 (CH$_2$), 31.2 (CH), 19.3 (CH$_3$), 17.9 (CH); MS m/z 432.9 (M+Na)$^+$, 842.8 (2M+Na)$^+$.

Preparation of {(R)-2-[(S)-2-(9H-Fluoren-9-ylmethoxycarbonylamino)-3-(tritylsulfanyl)-propionylamino]-3-methyl-butyrylamino}-acetic acid methyl ester (3)

To a stirred solution of 2 (1.0 g, 2.44 mmol) in CH$_3$CN (48.5 mL) at rt, was added Et$_2$NH (2.5 mL). After stirring for 3 h at rt the reaction mixture was diluted with hexane (100 mL) and concentrated to give the crude amine as a colourless oil. To a stirred solution of Fmoc-(STrt)-D-cysteine (1.70 g, 2.9 mmol) in CH$_3$CN (25 mL) was added EDAC.HCl (561.0 mg, 2.93 mmol), HOBt (396 mg, 2.93 mmol) and DIEA (1.31 ml, 7.32 mmol). After stirring at rt for 15 minutes, the crude amine was then added and the reaction mixture stirred for 4 h, solvent removed and the residue dissolved up in CH$_2$Cl$_2$ (100 mL), washed with water (25 mL), 10% HCl (25 mL), 5% NaHCO$_3$ (25 mL) and sat NaCl (25 mL) solutions, dried (Na$_2$SO$_4$), filtered, and solvent removed to give a off white solid which was re-crystallised from CH$_3$CN to give 3 as a white solid (1.46 g, 79%): [α]$^{22}_D$ −2.35 (c 0.50, CHCl$_3$); IR $\nu_{max}$ 3267, 1646, 1543 cm$^{-1}$; $^1$H NMR 400 MHz 7.76 (t, J=7.0 Hz, 2H), 7.54 (d, J=6.5 Hz, 2H), 7.39-7.21 (m 19H), 6.87 (s, 1H), 6.23 (d, J=8.0, 2H), 5.04 (d, J=7.0, 1H), 4.37 (d, J=7.0, 2H), 4.29 (dd, J=8.6, J=5.0, 1H), 4.17 (t, J=6.5, 1H), 3.96 (m, 1H), 3.72 (dd, , J=18.1, J=5.0, 1H), 3.65 (s, 3H), 3.60 (m, 1H), 2.70 (d, J=6.5, 2H), 2.30 (m, 1H), 1.70 (s, 1H), 0.87 (dd, J=13.0, J=7.0 Hz, 6H); $^{13}$C NMR 100 MHz 170.6 (C), 170.5 (C), 170.1 (C), 156.2 (C), 144.3 (C), 143.8 (C), 143.7 (C) 141.4 (C), 129.6 (CH), 128.4 (CH), 128.0 (CH), 127.8 (CH) 127.2 (CH), 125.1 (CH), 120.2 (CH), 67.6 (CH), 67.2 (CH$_2$), 58.4 (CH), 54.3 (CH), 52.4 (CH$_3$), 47.1 (CH), 40.9 (CH$_2$), 33.6 (CH$_2$), 30.0 (CH), 19.4 (CH$_3$), 17.4 (CH$_3$); MS m/z 777.8 (M+Na)$^+$. Anal. Calcd for C$_{45}$H$_{45}$N$_3$O$_6$S: 71.50; H, 6.00; N, 5.56. Found C, 71.42; H, 5.99; N, 5.55.

Preparation of ((R)-2-{(S)-2-[(R)-2-(9H-Fluoren-9-ylmethoxycarbonylamino)-propionylamino]-3-tritylsulfanyl-propionylamino}-3-methyl-butyrylamino)-acetic acid methyl ester (4)

To a stirred solution of 3 (400 mg, 0.53 mmol) in CH$_3$CN (30 mL) at rt was added Et$_2$NH (1.5 mL). After stirring for 3 h at rt the reaction mixture was diluted with heptane (60 mL) and concentrated to give the crude amine as a colourless oil. To a stirred solution of Fmoc-D-alanine (198 mg, 0.636 mmol) in CH$_3$CN (25 mL) was added EDAC.HCl (122.0 mg, 0.634 mmol), HOBt (86 mg, 0.636 mmol) and DIEA (502 μl, 1.91 mmol). After stirring at rt for 15 minutes the crude amine was then added and the reaction mixture stirred for 18 h, solvent removed and the residue dissolved up in CH$_2$Cl$_2$ (50 mL), washed with water (15 mL) 10% HCl (15 mL), 5% NaHCO$_3$ (15 mL) and sat NaCl (15 mL) solutions, dried (Na$_2$SO$_4$), filtered, and solvent removed to give a off white solid which was recrystallised from CH$_3$CN to give 4 as a white solid (670 mg, 81%): mp=195-197° C.; [α]$^{22}_D$ +5.1 (c 0.50, CHCl$_3$); IR $\nu_{max}$ 3267, 3054, 1744, 1706, 1635, 1531.1 cm$^{-1}$; $^1$H NMR 400 MHz 7.75 (d, J=7.5 Hz, 2H), 7.52 (d, J=7.0 Hz, 2H), 7.39 (m, 7H), 7.26-7.15 (m, 13H), 6.79 (s, 1H), 6.62 (s, 1H), 5.47 (s, 1H), 4.43-4.28 (m, 4H), 4.13 (m, 1H), 4.01 (m, 1H), 3.88 (s, 2H), 3.63 (s, 3H), 2.81 (m, 1H), 2.52 (m, 1H), 2.26, (m, 1H), 1.30 (d, J=6.0 Hz, 3H), 0.94 (d, J=6.0 Hz, 3H), 0.89 (d, J=7.0 Hz, 3H); $^{13}$C NMR 100 MHz 172.7, 171.1, 170.2, 156.1, 144.4, 143.9, 143.8, 141.4, 129.6, 128.3, 127.9, 127.2, 127.1, 125.1, 120.1, 58.5, 52.7, 52.3, 50.8, 47.2, 41.0, 33.5, 30.4, 19.3, 19.0, 17.7; MS m/z 849.2 (M+Na)$^+$, 865.1 (M+K)$^+$.

Preparation of ((R)-2-{(S)-2-[(R)-2-((E)-(S)-3-Hydroxy-7-tritylsulfanyl-hept-4-enoylamino)-propionylamino]-3-tritylsulfanyl-propionylamino}-3-methyl-butyrylamino)-acetic acid methyl ester (6)

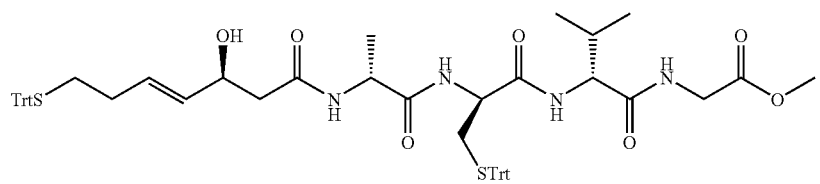

To a stirred solution of 4 (137 mg, 0.166 mmol) in CH$_3$CN (10 mL) at rt was added Et$_2$NH (0.5 mL). After stirring for 5 h at rt the reaction mixture was diluted with heptane (30 mL) and solvent removed, CH$_2$Cl$_2$ (10 ml) added, filtered and concentrated to give the crude amine as a colourless oil. To a stirred solution of the crude amine in CH$_2$Cl$_2$ (4 ml) was added 5 (84.0 mg, 0.149 mmol, prepared according to the procedure in Yurek-George, A.; Habens, F.; Brimmell, M.; Packham, G.; Ganesan, A. J. Am. Chem. Soc. 2004, 126, 1030-1031) and DMAP (2.2 mg, 0.0176 mmol) at 0° C. After stirring at rt for 8 hours, the solvent was removed and the residue was purified by flash chromatography (eluent 30-40% EtOAc/Hexanes) to give 6 as a white glass (127 mg, 85%): mp=191-193° C.; [α]$^{22}_D$ −18.0 (c 0.50, CHCl$_3$); IR $\nu_{max}$ 3272, 3064, 1758, 1692, 1621 cm$^{-1}$; $^1$H NMR 400 MHz (5%

CD$_3$OD/CDCl$_3$) 7.40 (m, 12H), 7.25 (m, 12H), 7.20 (m, 6H), 6.96 and 6.88 (labile NH, d, J=8.0 Hz, 1H), 5.49 (dt, J=15.0 Hz, 6.5 Hz, 1H), 5.37 (dd, J=15.5 Hz, 6.0 Hz, 1H), 4.32 (m, 2H), 4.22 (d, J=6.0 Hz, 1H), 3.98 (t, J=7.0 Hz, 1H), 3.92 (d, J=18.1 Hz, 1H), 3.72 (d, J=17.6 Hz, 1H), 3.67 (s, 3H), 2.64 (dd, J=13.0 Hz, 7.5 Hz, 1H), 2.58 (dd, J=13.0 Hz, 7.5 Hz, 1H), 2.56-2.18 (m, 9H), 2.11 (q, J=6.5 Hz, 2H), 1.31 (d, J=7.5 Hz, 3H), 0.91 (t, J=7.0 Hz, 6H); $^{13}$C NMR 100 MHz (5% CD$_3$OD/CDCl$_3$) 173.0, 172.0, 171.3, 170.5, 170.2, 144.9, 144.2, 132.8, 129.9, 129.7, 129.6, 129.5, 128.2, 128.1, 127.9, 127.1, 126.7, 69.6, 67.1, 66.7, 58.9, 58.8, 52.7, 52.2, 50.0, 49.8, 49.6, 49.5, 49.4, 49.1, 43.7, 40.9, 40.8, 33.1, 31.5, 31.3, 30.0, 19.2, 17.5; MS m/z 1050.4 (M+2Na)$^+$.

Preparation of ((R)-2-{(S)-2-[(R)-2-((E)-(S)-3-Hydroxy-7-tritylsulfanyl-hept-4-enoylamino)-propionylamino]-3-tritylsulfanyl-propionylamino}-3-methyl-butyrylamino)-acetic acid (7)

To a stirred solution of 6 (220 mg, 0.222 mmol) in 4:1 THF/H$_2$O (4.0 mL) at 0° C. was added LiOH (11 mg, 0.440 mmol). After stirring for 1 hour, the reaction mixture was diluted with H$_2$O (30 ml), acidified to pH 4-5 with 2M KHSO$_4$, and extracted with EtOAc (3×30 mL). The organic layer was washed with sat NaCl (15 mL), dried (Na$_2$SO$_4$), filtered, and concentrated to give a white solid which was triturated with ether, to give 7 as a white solid (199.5 mg 91%) which was used crude directly in the next step. mp=191-193° C.; [α]$^{22}_D$ –18.5 (c 0.50, CHCl$_3$); IR v$_{max}$ 3413, 1711, 1678, 1630, 1451 cm$^{-1}$; $^1$H NMR 400 MHz (5% CD$_3$OD/CDCl$_3$) 7.30 (m, 12H), 7.16 (m, 12H), 7.13 (m, 6H), 5.43 (dt, J=15.5 Hz, 6.0 Hz, 1H), 5.30 (dd, J=15.5 Hz, 6.0 Hz, 1H), 4.27 (m, 2H), 4.21 (m, 1H), 3.99 (m, 1H), 3.75 (s, 2H), 3.77 (m, br, 6H), 2.55 (dd, J=12.5 Hz, 6.5 Hz, 1H), 2.44 (dd, J=12.5 Hz, 7.5 Hz, 1H), 2.21 (m, 2H), 2.12 (m, 3H), 2.02 (m, 2H), 1.23 (d, J=7.0 Hz, 3H), 0.83 (d, J=7.0 Hz, 3H), 0.80 (d, J=7.0 Hz, 3H); $^{13}$C NMR 100 MHz (5% CD$_3$OD/CDCl$_3$) 173.0, 172.1, 171.6, 171.5, 170.5, 144.9, 144.3, 132.7, 129.8, 129.6, 129.5, 128.2, 127.9, 127.0, 126.7, 69.5, 67.1, 66.7, 58.7, 52.7, 43.5, 40.9, 33.2, 31.5, 31.3, 30.3, 19.2, 19.1, 17.6; MS m/z 1013.2 (M+Na)$^+$.

Preparation of (6R,9S,12R,16S)-6-Isopropyl-12-methyl-16-((E)-4-tritylsulfanyl-but-1-enyl)-9-tritylsulfanylmethyl-1-oxa-4,7,10,13-tetraaza-cyclohexadecane-2,5,8,11,14-pentaone (8)

To a stirred solution of the hydroxyl acid 7 (100 mg, 0.102 mmol) in CH$_2$Cl$_2$ (5 mL) at 0° C. was added a solution of DCC (28.2 mg, 0.137 mmol) in CH$_2$Cl$_2$ (0.5 mL) dropwise. After stirring for 30 minutes at 0° C. a solution of DMAP (2.5 mg, 0.0213 mmol) in CH$_2$Cl$_2$ (51 mL) was added, then stirred for 16 h at room temperature. The solid precipitate was filtered off, and the filtrate washed with CH$_2$Cl$_2$ (5 mL). The organic layer was washed with water (10 mL), 5% KHSO$_4$ (10 mL), 5% NaHCO$_3$ (10 mL) and sat NaCl (10 mL) solutions, dried (Na$_2$SO$_4$), filtered, and concentrated. The residue was purified by flash chromatography (eluent 30-50% EtOAc/hexanes) to give 8 as a white glass (37 mg, 38%).

Preparation of (E)-(1S,7R,10S,21R)-7-Isopropyl-21-methyl-2-oxa-12,13-dithia-5,8,20,23-tetraaza-bicyclo[8.7.6]tricos-16-ene-3,6,9,19,22-pentaone (Compound 001)

To a vigorously stirring solution of 12 (37.1 mg, 0.146 mmol) in MeOH (50 mL) was added the protected dithiol 8 (35 mg, 0.0365 mmol) in MeOH (20 mL) dropwise over 5 minutes. After stirring for a further 10 minutes, 0.2M ascorbate in 0.2M citric acid buffer (4 mL) was added and the organic phase concentrated, 1:1 EtOAc:NaCl (20 mL) was added, extracted with EtOAc (5×25 mL), the combined organic extract was dried (Na$_2$SO$_4$), filtered, and solvent removed. The residue was purified by flash chromatography (eluent 1-6% MeOH/CHCl$_3$) to give compound 001 as a white solid (11.8 mg, 67%): [α]$^{22}_D$ –98.0 (c 0.50, CHCl$_3$); IR v$_{max}$ 3300, 2477, 1734, 1659, 1526, 1446 cm$^{-1}$; $^1$H NMR 400 MHz 7.41 (d, J=6.0 Hz, 1H), 7.23 (d, J=8.5 Hz, 1H), 6.37 (s, 1H), 5.94 (dt, J=16.5, 7.5 Hz, 1H), 5.78-5.71 (m, 1H), 4.86 (m, 1H), 4.26 (d, J=7.5 Hz, 1H), 4.17 (d, J=14.0 Hz, 1H), 4.08 (d, J=14.0 Hz, 1H), 3.44 (dd, J=14.5 Hz, 10.0 Hz, 1H), 3.22 (d, J=10.0 Hz, 1H), 2.88-2.56 (m, 8H), 1.49 (d, J=7.5 Hz, 3H), 0.98 (d, J=6.5 Hz, 3H), 0.92 (d, J=6.5 Hz, 3H); $^{13}$C NMR 100 MHz 173.2, 171.9, 170.9, 170.1, 168.3, 129.8, 70.2, 64.4, 55.9, 51.7, 41.7, 38.2, 37.9, 35.7, 31.0, 26.9, 20.2, 19.7, 15.4; HRMS m/z 509.1495 (M+Na)$^+$ expected 509.1499.

General Procedure for Synthesis of Analogues Represented by Formula (I).

In step (a), an amino acid ester bearing the side-chain R$_2$ is condensed with a second amino acid bearing the side-chain R$_1$ to give a dipeptide. In step (b), the dipeptide is condensed with a protected cysteine derivative to give a tripeptide. In step (c) the tripeptide is coupled with an amino acid to provide a protected tetrapeptide. In step (d), the N-terminus of the tetrapeptide is deprotected, and the free amine is coupled with a β-hydroxy acid derivative. In the preferred embodiment of the invention, R$_4$ and R$_5$ are H, with X being a chiral auxiliary as reported in Yurek-George, A.; Habens, F.; Brimmell, M.; Packham, G.; Ganesan, A. J. Am. Chem. Soc. 2004, 126, 1030-1031. In step (e), the ester group is hydrolysed, followed by cyclization in step (f) and disulfide bond formation in (g) to complete the synthesis of the bicyclic depsipeptide compounds (I).

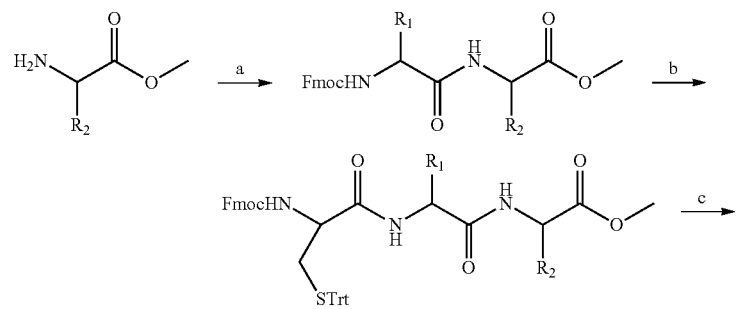

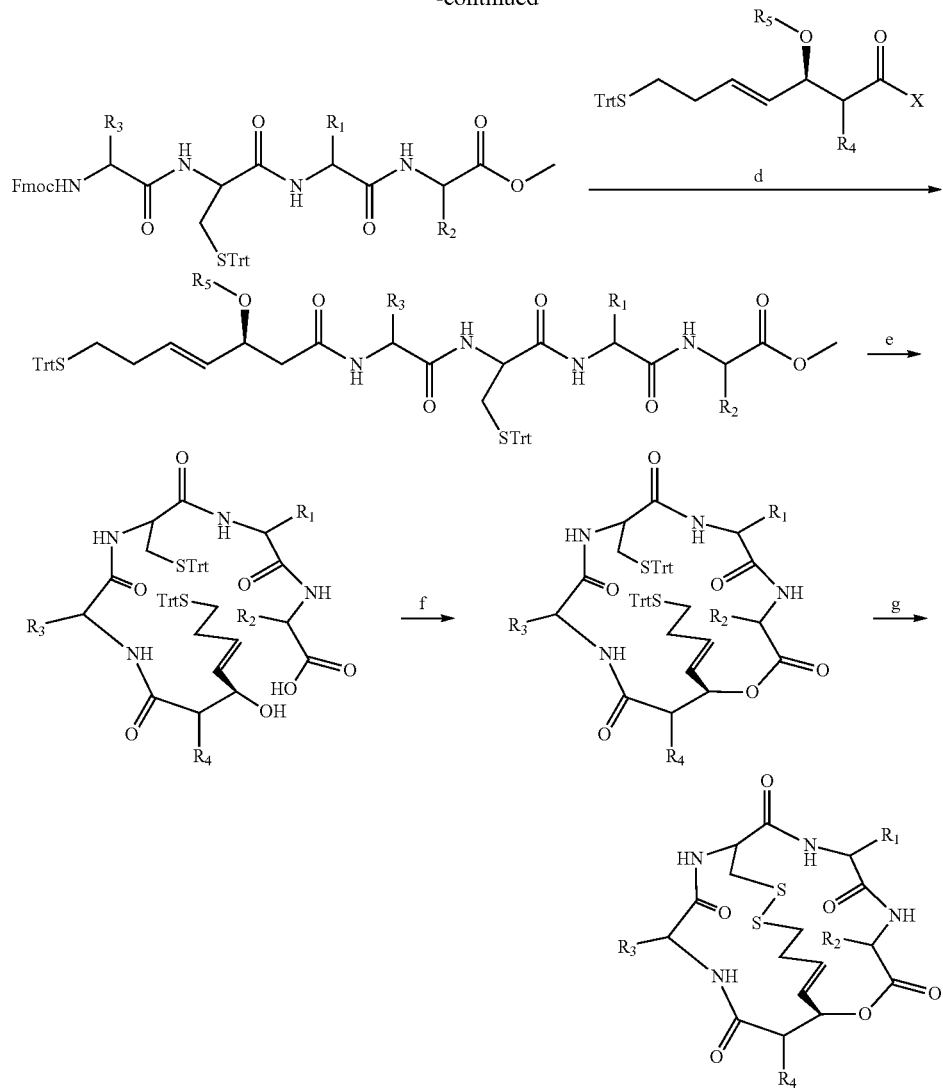
Synthesis of analogues 9A-F by the general scheme.
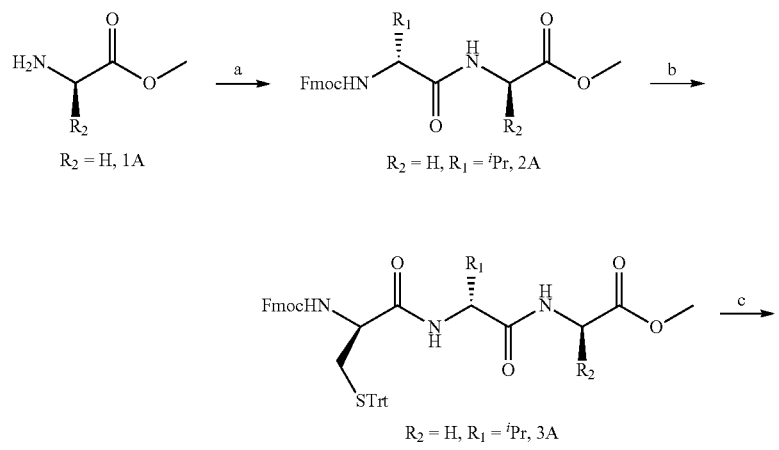

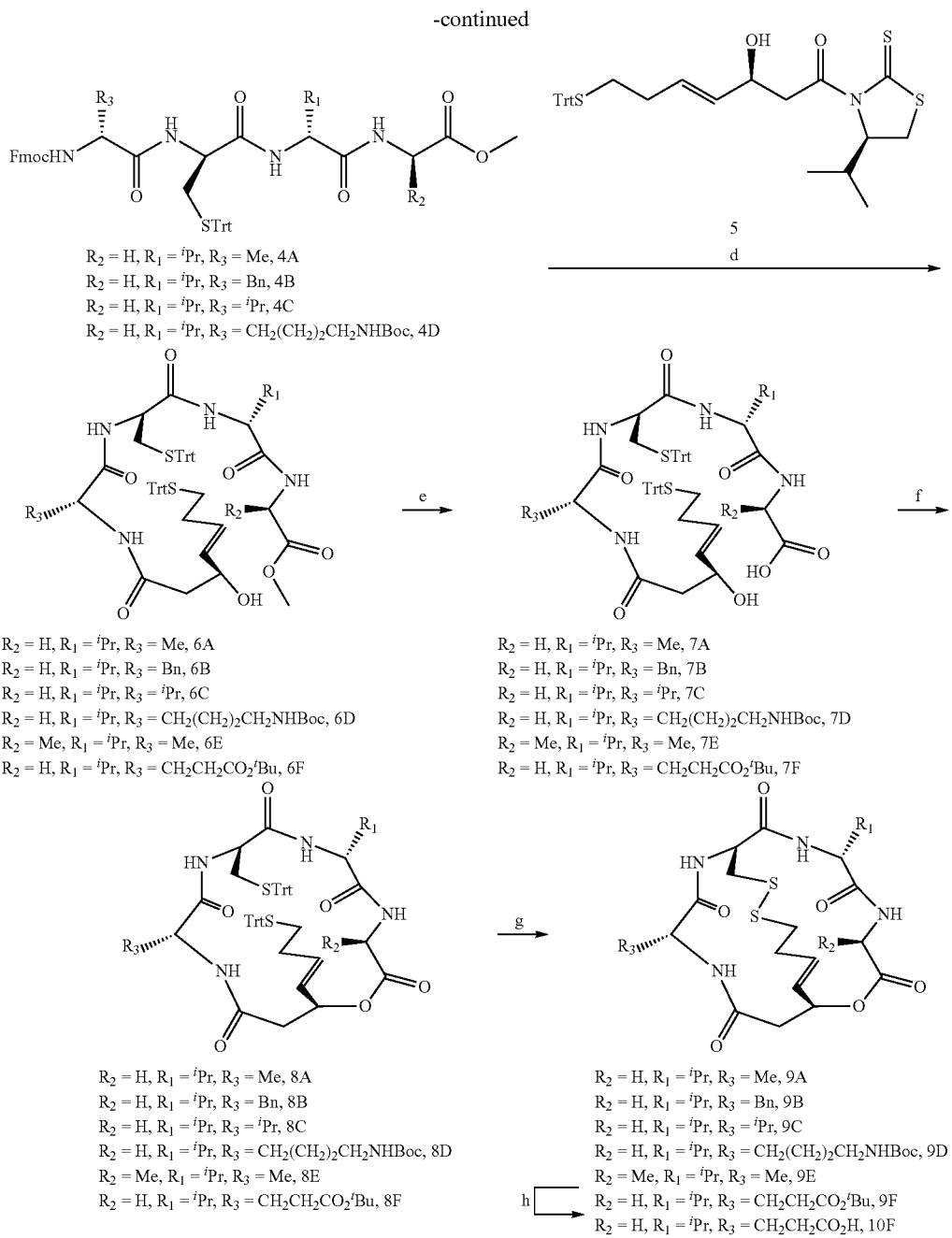

Preparation of [(R)-2-(9H-fluoren-9-ylmethoxycarbonylamino)-3-methyl-butyrylamino]-acetic acid methyl ester (2A)

To a stirred solution of Fmoc protected D-valine (2.70 g, 7.96 mmol) in CH$_2$Cl$_2$ (50 mL) was added EDAC.HCl (1.83 g, 9.55 mmol), HOBt (1.30 g, 9.55 mmol) and DIEA (3.8 mL, 27.86 mmol). After stirring at RT for 15 minutes, glycine methyl ester (1A, 1.0 g, 7.96 mmol) was then added and the reaction mixture stirred for 4 h, diluted with CH$_2$Cl$_2$ (50 mL) washed with water (25 mL), 10% HCl (25 mL), 5% NaHCO$_3$ (25 mL) and sat NaCl (25 mL) solutions, dried (Na$_2$SO$_4$), filtered, and concentrated to give an off white solid which was re-crystallised from CH$_3$CN to give 2A as a white solid (2.81 g, 86%): mp=148-150° C.; [α]$^{22}_D$ −7.32 (c 0.50, CHCl$_3$); IR $v_{max}$ 3287, 1750, 1690, 1649, 1535 cm$^{-1}$; $^1$H NMR (400 MHz, CDCl$_3$) δ 7.75 (d, J=7.5 Hz, 2H), 7.57 (d, J=7.0 Hz, 2H), 7.39 (t, J=7.0 Hz, 2H), 7.28 (m, 2H), 6.54 (s, 1H), 5.44 (s, 1H), 4.43-4.38 (m, 2H), 4.21 (t, J=7.0 Hz, 1H), 4.01-3.96 (m, 3H), 3.72 (s, 3H), 2.16 (m, 1H), 0.96 (t, J=9.0 Hz, 6H); $^{13}$C NMR (100 MHz, CDCl$_3$) δ 171.7 (C), 170.1 (C), 156.6 (C), 143.9 (C), 141.4 (C), 127.8 (CH), 127.2 (CH), 125.2 (CH), 120.1 (CH), 67.2 (CH$_2$), 60.4 (CH), 52.5 (CH), 47.3 (CH$_3$), 41.2 (CH$_2$), 31.2 (CH), 19.3 (CH$_3$), 17.9 (CH); MS m/z 842.8 (30%, [2M+Na]$^+$), 432.9 (100%, [M+Na]$^+$).

Preparation of {(R)-2-[(S)-2-(9H-fluoren-9-yl-methoxycarbonylamino)-3-(tritylsulfanyl)-propionylamino]3-methyl-butyrylamino}-acetic acid methyl ester (3A)

To a stirred solution of 2A (1.0 g, 2.44 mmol) in CH$_3$CN (48.5 mL) at RT, was added Et$_2$NH (2.5 mL). After stirring for 3 h at RT the reaction mixture was diluted with hexane (100 mL) and concentrated to give the crude amine as a colourless oil. To a stirred solution of Fmoc-(STrt)-D-cysteine (1.70 g, 2.9 mmol) in CH$_3$CN (25 mL) was added EDAC.HCl (561.0 mg, 2.93 mmol), HOBt (396 mg, 2.93 mmol) and DIEA (1.31 mL, 7.32 mmol). After stirring at RT for 15 minutes, the crude amine was then added and the reaction mixture stirred for 4 h, solvent removed and the residue dissolved up in CH$_2$Cl$_2$ (100 mL), washed with water (25 mL), 10% HCl (25 mL), 5% NaHCO$_3$ (25 mL) and sat NaCl (25 mL) solutions, dried (Na$_2$SO$_4$), filtered, and solvent removed to give an off white solid which was re-crystallised from CH$_3$CN to give 3A as a white solid (1.46 g, 79%): [α]$^{22}_D$ −2.35 (c 0.50, CHCl$_3$); IR ν$_{max}$ 3267, 1646, 1543 cm$^{-1}$; $^1$H NMR 400 MHz (400 MHz, CDCl$_3$) δ 7.76 (t, J=7.0 Hz, 2H), 7.54 (d, J=6.5 Hz, 2H), 7.39-7.21 (m 19H), 6.87 (s, 1H), 6.23 (d, J=8.0, 2H), 5.04 (d, J=7.0, 1H), 4.37 (d, J=7.0, 2H), 4.29 (dd, J=8.6, 5.0, 1H), 4.17 (t, J=6.5, 1H), 3.96 (m, 1H), 3.72 (dd, , J=18.1, 5.0, 1H), 3.65 (s, 3H), 3.60 (m, 1H), 2.70 (d, J=6.5, 2H), 2.30 (m, 1H), 1.70 (s, 1H), 0.87 (dd, J=13.0, J=7.0, 6H); $^{13}$C NMR (100 MHz, CDCl$_3$) δ 170.6 (C), 170.5 (C), 170.1 (C), 156.2 (C), 144.3 (C), 143.8 (C), 143.7 (C) 141.4 (C), 129.6 (CH), 128.4 (CH), 128.0 (CH), 127.8 (CH) 127.2 (CH), 125.1 (CH), 120.2 (CH), 67.6 (CH), 67.2 (CH$_2$), 58.4 (CH), 54.3 (CH), 52.4 (CH$_3$), 47.1 (CH), 40.9 (CH$_2$), 33.6 (CH$_2$), 30.0 (CH), 19.4 (CH$_3$), 17.4 (CH$_3$); LRMS m/z 777.8 (100%, [M+Na]$^+$); Anal. Calcd for C$_{45}$H$_{45}$N$_3$O$_6$S: 71.50; H, 6.00; N, 5.56. Found C, 71.42; H, 5.99; N, 5.55.

Preparation of ((R)-2-{(S)-2-[(R)-2-(9H-fluoren-9-ylmethoxycarbonylamino)-propionylamino]-3-tritylsulfanyl-propionylamino}-3-methyl-butyrylamino)-acetic acid methyl ester (4A)

To a stirred solution of 3A (900 mg, 1.19 mmol) in CH$_3$CN/CH$_2$Cl$_2$ (1:1, 60 mL) at RT was added Et$_2$NH (3 mL). After stirring for 3 h at RT the reaction mixture was diluted with heptane (60 mL) and concentrated to give the crude amine as a colourless oil. To a stirred solution of Fmoc-D-alanine (529 mg, 1.7 mmol) in CH$_2$Cl$_2$ (30 mL) was added EDAC.HCl (326 mg, 1.7 mmol), HOBt (230 mg, 1.7 mmol) and DIEA (627 μl, 3.6 mmol). After stirring at RT for 10 minutes a solution of the crude amine in CH$_2$Cl$_2$ (20 mL) was then added and the reaction mixture stirred for 18 h. Whereupon the reaction was washed with water (15 mL), 10% HCl (15 mL), 5% NaHCO$_3$ (15 mL) and sat NaCl (15 mL) solutions, dried (Na$_2$SO$_4$), filtered, and the solvent removed to give an off white solid which was recrystallised from CH$_3$CN to give 4A as a white solid (810 mg, 0.98 mmol, 82%). mp=195-197° C.; [α]$^{22}_D$ +5.1 (c 0.50, CHCl$_3$); IR ν$_{max}$ 3267, 3054, 1744, 1706, 1635, 1531.1 cm$^{-1}$; $^1$H NMR (400 MHz, CDCl$_3$) δ 7.75 (d, J=7.5 Hz, 2H), 7.52 (d, J=7.0 Hz, 2H), 7.39 (m, 7H), 7.26-7.15 (m, 13H), 6.79 (s, 1H), 6.62 (s, 1H), 5.47 (s, 1H), 4.43-4.28 (m, 4H), 4.13 (m, 1H), 4.01 (m, 1H), 3.88 (s, 2H), 3.63 (s, 3H), 2.81 (m, 1H), 2.52 (m, 1H), 2.26, (m, 1H), 1.30 (d, J=6.0 Hz, 3H), 0.94 (d, J=6.0 Hz, 3H), 0.89 (d, J=7.0 Hz, 3H); $^{13}$C NMR (100 MHz, CDCl$_3$) δ 172.7, 171.1, 170.2, 156.1, 144.4, 143.9, 143.8, 141.4, 129.6, 128.3, 127.9, 127.2, 127.1, 125.1, 120.1, 58.5, 52.7, 52.3, 50.8, 47.2, 41.0, 33.5, 30.4, 19.3, 19.0, 17.7; LRMS m/z 849.2 (100%, [M+Na]$^+$), 865.1 (20%, [M+K]$^+$).

Preparation of ((R)-2-{(S)-2-[(R)-2-((E)-(S)-3-hydroxy-7-tritylsulfanyl-hept-4-enoylamino)-propionylamino]-3-tritylsulfanyl-propionylamino}-3-methyl-butyrylamino)-acetic acid methyl ester (6A)

To a stirred solution of 4A (760 mg, 0.92 mmol) in CH$_2$Cl$_2$/CH$_3$CN (3:2, 150 mL) at RT was added Et$_2$NH (7.5 mL). After stirring for 5 h at RT the reaction mixture was diluted with heptane (60 mL) and solvent removed, CH$_2$Cl$_2$ (50 mL) added, filtered and concentrated to give the crude amine as a colourless oil. To a stirred solution of the crude amine in CH$_2$Cl$_2$ (30 mL) was added a solution of 5 (672 mg, 1.20 mmol, prepared according to the procedure in Yurek-George, A.; Habens, F.; Brimmell, M.; Packham, G.; Ganesan, A. *J. Am. Chem. Soc.* 2004, 126, 1030-1031) in CH$_2$Cl$_2$ (5 mL) and DMAP (15 mg, 0.12 mmol) at RT . After stirring at RT for 12 hours, the solvent was removed and the residue was purified by flash chromatography (eluent 10-100% EtOAc/CH$_2$Cl$_2$) to give 6A as a white glass (740 mg, 80%): mp=191-193° C.; [α]$^{22}_D$ −18.0 (c 0.50, CHCl$_3$); IR ν$_{max}$ 3272, 3064, 1758, 1692, 1621 cm$^{-1}$; $^1$H NMR (400 MHz, 5% CD$_3$OD/CDCl$_3$) δ 7.40 (m, 12H), 7.25 (m, 12H), 7.20 (m, 6H), 6.96 and 6.88 (labile NH, d, J=8.0 Hz, 1H), 5.49 (dt, J=15.0 Hz, 6.5 Hz, 1H), 5.37 (dd, J=15.5 Hz, 6.0 Hz, 1H), 4.32 (m, 2H), 4.22 (d, J=6.0 Hz, 1H), 3.98 (t, J=7.0 Hz, 1H), 3.92 (d, J=18.1 Hz, 1H), 3.72 (d, J=17.6 Hz, 1H), 3.67 (s, 3H), 2.64 (dd, J=13.0, 7.5 Hz, 1H), 2.58 (dd, J=13.0, 7.5 Hz, 1H), 2.56-2.18 (m, 9H), 2.11 (q, J=6.5 Hz, 2H), 1.31 (d, J=7.5 Hz, 3H), 0.91 (t, J=7.0 Hz, 6H); $^{13}$C NMR (100 MHz, 5% CD$_3$OD/CDCl$_3$) δ 173.0, 172.0, 171.3, 170.5, 170.2, 144.9, 144.2, 132.8, 129.9, 129.7, 129.6, 129.5, 128.2, 128.1, 127.9, 127.1, 126.7, 69.6, 67.1, 66.7, 58.9, 58.8, 52.7, 52.2, 50.0, 49.8, 49.6, 49.5, 49.4, 49.1, 43.7, 40.9, 40.8, 33.1, 31.5, 31.3, 30.0, 19.2, 17.5; LRMS m/z 1050.4 (100%, [M+Na]$^+$).

Preparation of ((R)-2-{(S)-2-[(R)-2-((E)-(S)-3-hydroxy-7-tritylsulfanyl-hept-4-enoylamino)-propionylamino]-3-tritylsulfanyl-propionylamino}-3-methyl-butyrylamino)-acetic acid (7A)

To a stirred solution of 6A (700 mg, 0.70 mmol) in THF (15 mL) at 0° C. was added a solution of LiOH (25 mg, 1.05 mmol) in H$_2$O (2.4 mL). After stirring for 1 hour, the reaction mixture was diluted with H$_2$O (30 mL), acidified to pH 3-4 with 1M KHSO$_4$, and extracted with EtOAc (3×30 mL). The organic layer was washed with sat NaCl (15 mL), dried (Na$_2$SO$_4$), filtered, and concentrated to give a white solid which was triturated with ether, to give 7A as a white solid (693 mg, 99%) which was used crude directly in the next step. mp=191-193° C.; [α]$^{22}_D$ 18.5 (c 0.50, CHCl$_3$); IR ν$_{max}$ 3413, 1711, 1678, 1630, 1451 cm$^{-1}$; $^1$H NMR (400 MHz, 5% CD$_3$OD/CDCl$_3$) δ 7.30 (m, 12H), 7.16 (m, 12H), 7.13 (m, 6H), 5.43 (dt, J=15.5 Hz, 6.0 Hz, 1H), 5.30 (dd, J=15.5 Hz, 6.0 Hz, 1H), 4.27 (m, 2H), 4.21 (m, 1H), 3.99 (m, 1H), 3.75 (s, 2H), 3.77 (m, br, 6H), 2.55 (dd, J=12.5 Hz, 6.5 Hz, 1H), 2.44 (dd, J=12.5 Hz, 7.5 Hz, 1H), 2.21 (m, 2H), 2.12 (m, 3H), 2.02 (m, 2H), 1.23 (d, J=7.0 Hz, 3H), 0.83 (d, J=7.0 Hz, 3H), 0.80 (d, J=7.0 Hz, 3H); $^{13}$C NMR (100 MHz, 5% CD$_3$OD/CDCl$_3$) δ 173.0, 172.1, 171.6, 171.5, 170.5, 144.9, 144.3, 132.7, 129.8, 129.6, 129.5, 128.2, 127.9, 127.0, 126.7, 69.5, 67.1, 66.7, 58.7, 52.7, 43.5, 40.9, 33.2, 31.5, 31.3, 30.3, 19.2, 19.1, 17.6; LRMS m/z 1013.2 (100%, [M+Na]$^+$).

Preparation of (6R,9S,12R,16S)-6-isopropyl-12-methyl-16-((E)-4-tritylsulfanyl-but-1-enyl)-9-tritylsulfanylmethyl-1-oxa-4,7,10,13-tetraaza-cyclohexadecane-2,5,8,11,14-pentaone (8A)

To a solution of 2-methyl-6-nitrobenzoic anhydride (MNBA) (289 mg, 0.84 mmol) and DMAP (205 mg, 1.68 mmol) in $CH_2Cl_2$ (160 mL) was added dropwise a solution of acid 7A (693 mg, 0.70 mmol) in $CH_2Cl_2$/THF (2:1, 600 mL) over 5 hours. After a further 12 hours 1M HCl (150 mL) was added, extracting with $CH_2Cl_2$ (3×100 mL). The combined organic phase was then washed with sat. $NaHCO_3$ (150 mL) followed by brine (80 mL), dried ($MgSO_4$), filtered, and concentrated. The residue was purified by flash chromatography (eluent 50-100% EtOAc/hexanes) to give 8A as a white glass (478 mg, 0.49 mmol, 70%): $[\alpha]^{22}_D$ −7.0 (c 0.50, $CHCl_3$); IR $\nu_{max}$ 1735, 1659, 1526 cm$^{-1}$; $^1$H NMR (400 MHz, $CDCl_3$) δ 7.43-7.33 (m, 12H), 7.32-7.13 (m, 20H), 6.77 (d, J=5.3 Hz, 1H), 6.54 (d, J=7.3 Hz, 1H), 5.58 (dt, J=15.1, 6.8 Hz, 1H), 5.44-5.29 (m, 2H), 4.55 (dd, J=16.8, 9.0 Hz, 1H), 4.46 (dd, J=9.5, 4.3 Hz, 1H), 3.89 (quin, (dd, J=7.0 Hz, 1H), 3.77 (dt, J=8.3, 5.3 Hz, 1H), 3.43 (dd, J=16.8, 2.8 Hz, 1H), 3.03 (dd, J=12.6, 8.3 Hz, 1H), 2.61-2.49 (m, 3H), 2.18 (t, J=7.5 Hz, 2H), 2.11-1.95 (m, 2H), 1.38 (d, J=7.0 Hz, 3H), 0.94 (d, J=6.8 Hz, 3H), 0.90 (d, J=6.8 Hz, 3H); $^{13}$C-NMR (100 MHz, $CDCl_3$) δ 174.0 (C), 170.9 (C), 170.8 (C), 169.8 (C), 169.3 (C), 144.9 (C), 144.3 (C), 133.2 (CH), 129.7 (CH), 129.5 (CH), 128.3 (CH), 128.0 (CH), 127.2 (CH), 126.8 (CH), 72.3 (CH), 67.3 (C), 66.8 (C), 58.3 (CH), 55.9 (CH), 50.5 (CH), 41.7 (2×$CH_2$), 32.5 ($CH_2$), 31.3 ($CH_2$), 31.2 ($CH_2$), 28.8 (CH), 19.8 ($CH_3$), 19.8 ($CH_3$), 17.2 ($CH_3$), 16.7 ($CH_3$); LRMS (ES$^+$) m/z 996 (100%, [M+Na]$^+$), 974 (10%, [M+H]$^+$).

Preparation of (E)-(1S,7R,10S,21R)-7-isopropyl-21-methyl-2-oxa-12,13-dithia-5,8,20,23-tetraaza-bicyclo[8.7.6]tricos-16-ene-3,6,9,19,22-pentaone (9A)

To a vigorously stirring solution of 12 (1120 mg, 4.42 mmol) in $CH_2Cl$/MeOH (9:1, 1000 mL) was added the protected dithiol 8A (430 mg, 0.44 mmol) in $CH_2Cl_2$/MeOH (9:1, 500 mL) dropwise over 30 minutes. After stirring for a further 30 minutes, 0.1M sodium thiosulfate (300 mL) and sat. NaCl (100 mL) were added, extracting with $CH_2Cl_2$ (3×100 mL). The combined organic extract was dried ($MgSO_4$), filtered, and solvent removed. The residue was purified by flash chromatography (eluent 1-6% MeOH/$CH_2Cl_2$) to give 9A (205 mg, 0.42 mmol, 96%) as a white solid: $[\alpha]^{22}_D$ −98.0 (c 0.50, $CHCl_3$); IR $\nu_{max}$ 3300, 2477, 1734, 1659, 1526, 1446 cm$^{-1}$; $^1$H NMR (400 MHz, $CDCl_3$) δ 7.46 (d, J=6.5 Hz, 1H), 7.33 (t, J=5.3 Hz, 1H), 7.28 (d, J=8.8 Hz, 1H), 6.60 (d, J=3.8 Hz, 1H), 5.95 (dtd, J=16.1, 6.5, 2.0 Hz, 1H), 5.80-5.70 (m, 2H), 4.85 (ddd, J=9.8, 8.5, 3.8 Hz, 1H), 4.21 (qd, J=7.3, 3.8 Hz, 1H), 4.11 (d, J=5.3 Hz, 2H), 3.44 (dd, J=15.6, 10.0 Hz, 1H), 3.20 (dd, J=10.3, 6.8 Hz, 1H), 3.01-2.95 (m, 2H), 2.92 (dd, J=15.6, 4.0 Hz, 1H), 2.85-2.58 (m, 5H) 1.49 (d, J=7.5 Hz, 3H), 0.98 (d, J=6.5 Hz, 3H), 0.92 (d, J=6.5 Hz, 3H); $^{13}$C NMR 100 MHz 173.3 (C), 171.6 (C), 171.0 (C), 169.4 (C), 168.2 (C), 130.4 (CH), 130.3 (CH), 69.8 (CH), 64.9 (CH), 54.5 (CH), 52.0 (CH), 42.4 (2×$CH_2$), 38.7 ($CH_2$), 38.6 ($CH_2$), 32.7 ($CH_2$), 27.5 (CH), 20.8 ($CH_3$), 20.1 ($CH_3$), 16.7 ($CH_3$); LRMS (ES$^+$) m/z 995 (50%, [2M+Na]$^+$), 509 (80%, [M+Na]$^+$), 487 (100%, [M+H]$^+$); HRMS m/z 509.1495 (M+Na)$^+$ expected 509.1499.

Preparation of ((R)-2-{(S)-2-[(R)-2-(9H-fluoren-9-ylmethoxycarbonylamino)-3-phenyl-propionylamino]-3-tritylsulfanyl-propionylamino}-3-methyl-butyrylamino)-acetic acid methyl ester (4B)

To a stirred solution of 3A (836 mg, 1.11 mmol) in $CH_3CN$/$CH_2Cl_2$ (1:1, 60 mL) at RT was added $Et_2NH$ (3 mL). After stirring for 3 h at RT the reaction mixture was diluted with heptane (60 mL) and concentrated to give the crude amine as a colourless oil. To a stirred solution of Fmoc-D-phenylalanine (650 mg, 1.7 mmol) in $CH_2Cl_2$ (30 mL) was added EDAC.HCl (326 mg, 1.7 mmol), HOBt (230 mg, 1.7 mmol) and DIEA (627 μl, 3.6 mmol). After stirring at RT for 10 minutes a solution of the crude amine in $CH_2Cl_2$ (20 mL) was then added and the reaction mixture stirred for 12 h. Whereupon the reaction was washed with water (15 mL), 10% HCl (15 mL), 5% $NaHCO_3$ (15 mL) and sat NaCl (15 mL) solutions, dried ($Na_2SO_4$), filtered, and the solvent removed to give an off white solid which was recrystallised from $CH_3CN$ to give 4B as a white solid (800 mg, 0.89 mmol, 80%): IR $\nu_{max}$ 3264, 3053, 1742, 1701, 1636, 1532 cm$^{-1}$; $^1$H-NMR (400 MHz, $CDCl_3$) δ 7.75 (d, J=7.5 Hz, 2H), 7.46 (t, J=7.5 Hz, 2H), 7.41-7.31 (m, 8H), 7.30-7.07 (m, 16H), 7.01 (br s, 1H), 6.54 (br s, 2H), 5.29 (br s, 1H), 4.48-4.32 (m, 3H), 4.25-4.13 (m, 1H), 4.10 (t, J=8.5 Hz, 1H), 3.99-3.76 (m, 3H), 3.65 (s, 3H), 3.10-2.88 (m, 2H), 2.83-2.69 (m, 1H), 2.49 (dd, J=13.0, 6.3 Hz, 1H), 2.36-2.22, (m, 1H), 0.93 (t, J=7.0 Hz, 6H); $^{13}$C NMR 100 MHz 171.2 (C), 171.0 (C), 170.2 (C), 170.0 (C), 156.2 (C), 144.3 (C), 143.9 (C), 143.7 (C), 141.4 (C), 136.0 (C), 129.5 (CH), 129.3 (CH), 129.0 (CH), 128.3 (CH), 127.9 (CH), 127.4 (CH), 127.2 (CH), 127.1 (CH), 125.2 (CH), 120.1 (CH), 67.3 ($CH_2$), 58.6 (CH), 56.2 (CH), 52.8 (CH), 52.3 ($CH_3$), 47.2 (CH), 41.0 ($CH_2$), 38.3 ($CH_2$), 33.5 ($CH_2$), 30.2 (CH), 19.4 ($CH_3$), 17.7 ($CH_3$); LRMS (ES$^+$) m/z 1828 (30%, [2M+Na]$^+$), 925 (100%, [M+Na]$^+$).

Preparation of ((R)-2-{(S)-2-[(R)-2-((E)-(S)-3-hydroxy-7-tritylsulfanyl-hept-4-enoylamino)-3-phenyl-propionylamino]-3-tritylsulfanyl-propionylamino}-3-methyl-butyrylamino)-acetic acid methyl ester (6B)

To a stirred solution of 4B (245 mg, 0.28 mmol) in $CHCl_3$/$CH_3CN$ (1:1, 14 mL) at RT was added $Et_2NH$ (1 mL). After stirring for 5 h at RT the reaction mixture was diluted with heptane (10 mL) and solvent removed to give the crude amine as a colourless oil. To a stirred solution of the crude amine in $CH_2Cl_2$ (10 mL) was added a solution of 5 (193 mg, 0.34 mmol) in $CH_2Cl_2$ (5 mL) and DMAP (4 mg, 0.034 mmol) at RT. After stirring at RT for 12 hours, the solvent was removed and the residue was purified by flash chromatography (eluent 2-4% MeOH/$CH_2Cl_2$) to give 6B (190 mg, 64%) as a white solid: $^1$H NMR (400 MHz, $CDCl_3$) δ 7.46-7.05 (m, 37H), 6.85 (br s, 1H), 6.34 (br s, 1H), 5.44 (dt, J=15.3, 6.5 Hz, 1H), 5.29 (dd, J=15.3, 6.2 Hz, 1H), 4.74 (br d, J=5.3 Hz, 1H), 4.37 (t, J=7.0 Hz, 1H), 4.33-4.25 (m, 1H), 4.20-4.08 (m, 1H), 3.93-3.74 (m, 2H), 3.65 (s, 3H), 3.31 (br s, 1H), 3.06 (dd, J=14.3, 5.3 Hz, 1H), 2.96 (dd, J=14.3, 7.3 Hz, 1H), 2.59 (dd, J=12.5, 6.8 Hz, 1H), 2.33-2.08 (m, 5H), 2.04 (q, J=7.0 Hz, 2H), 0.90 (t, J=6.3 Hz, 6H); $^{13}$C NMR (100 MHz, $CDCl_3$) δ 171.9 (C), 171.2 (C), 171.1 (C), 170.4 (2×C), 145.0 (C), 144.3 (C), 136.1 (C), 132.5 (CH), 130.1 (CH), 129.7 (CH), 129.5 (CH), 129.3 (CH), 128.8 (CH), 128.2 (CH), 128.0 (CH), 127.3 (CH), 127.1 (CH), 126.7 (CH), 69.8 (CH), 67.1 (C), 66.8 (C), 58.9 (CH), 54.4 (CH), 52.6 (CH), 52.3 ($CH_3$), 43.7 ($CH_2$), 41.0 ($CH_2$), 37.6 ($CH_2$), 33.8 ($CH_2$), 31.5 ($CH_2$), 31.4

($CH_2$), 30.3 (CH), 19.3 ($CH_3$), 17.9 ($CH_3$); LRMS ($ES^+$) m/z 1104 (100%, $[M+Na]^+$), 1082 (50%, $[M+H]^+$).

Preparation of (6R,9S,12R,16S)-12-benzyl-6-isopropyl-16-((E)-4-tritylsulfanyl-but-1-enyl)-9-tritylsulfanylmethyl-1-oxa-4,7,10,13-tetraaza-cyclohexadecane-2,5,8,11,14-pentaone (8B)

To a solution of methyl ester 6B (180 mg, 0.17 mmol) in THF at 0° C. (10 mL) was added a solution of LiOH (6 mg, 0.25) in $H_2O$ (1.5 mL). After 1 h the reaction was quenched by addition of 1 M HCl (6 mL). $CHCl_3$ (50 mL) was added and the organic phase separated, extracting with $CHCl_3$ (2×10 mL). The organic phase was washed with brine (15 mL), dried ($MgSO_4$), filtered, and concentrated in vacuo to give the crude acid 7B (179 mg, quantative) as a white solid that was used immediately in the next step: ($ES^-$) m/z 1066 (100%, $[M-H]^-$).

To a solution of MNBA (68 mg, 0.20 mmol) and DMAP (49 mg, 0.40 mmol) in $CH_2Cl_2$ (40 mL) was added dropwise a solution of acid 7B (179 mg, 0.17 mmol) in $CH_2Cl_2$/THF (15:1, 160 mL) over 3 h (Nb dissolve acid in THF first then add $CH_2Cl_2$). After a further 14 h the reaction was quenched by the addition of 1 M HCl (40 mL). The organic phase was separated (extracting with $CH_2Cl_2$) and washed sequentially with $NaHCO_3$ (30 mL) and brine (20 mL). The combined organic phase was dried ($MgSO_4$), filtered, and concentrated in vacuo to give a yellow oil. Purification by column chromatography on silica gel (30-70% EtOAc/$CH_2Cl_2$) gave 8B (108 mg, 0.10 mmol, 60%) as a white solid: $^1$H-NMR (400 MHz, $CDCl_3$) δ 7.42-7.08 (m, 35H), 7.05 (d, J=7.3 Hz, 2H), 6.96 (br s, 1H), 6.54 (br s, 1H), 5.46 (dt, J=15.3, 6.5 Hz, 2H), 5.21 (dd, J=15.3, 6.6 Hz, 1H), 4.49 (dd, J=13.5, 4.3 Hz, 1H), 4.32 (dd, J=16.8, 9.0 Hz, 1H), 4.16-4.06 (m, 1H), 3.85 (br q, J=6.0 Hz, 1H), 3.02-2.82 (m, 4H), 2.65-2.53 (m, 2H), 2.40 (dd, J=14.6, 3.3 Hz, 1H), 2.23 (dd, J=14.6, 11.3 Hz, 1H), 2.10 (t, J=7.0 Hz, 2H), 1.97-1.84 (m, 2H), 0.98 (d, J=7.0 Hz, 3H), 0.92 (d, J=7.0 Hz, 3H); $^{13}$C-NMR (100 MHz, $CDCl_3$) δ 173.5 (C), 170.8 (C), 170.7 (C), 169.9 (2×C), 144.9 (C), 144.2 (C), 136.3 (C), 132.7 (CH), 129.6 (CH), 129.5 (CH), 129.3 (CH), 128.9 (CH), 128.3 (CH), 128.0 (CH), 127.9 (CH), 127.3 (CH), 127.1 (CH), 126.7 (CH), 72.2 (CH), 67.3 (C), 66.7 (C), 58.3 (CH), 55.8 (2×CH), 42.0 ($CH_2$), 41.4 ($CH_2$), 36.7 ($CH_2$), 32.3 ($CH_2$), 31.3 ($CH_2$), 31.1 ($CH_2$), 28.7 (CH), 19.8 ($CH_3$), 17.2 ($CH_3$); LRMS ($ES^+$) m/z 1071 (100%, $[M+Na]^+$), 1066 (10%, $[M+NH_4]^+$), 1049 (10%, $[M+H]^+$).

Preparation of (E)-(1S,7R,10S,21R)-21-benzyl-7-isopropyl-2-oxa-12,13-dithia-5,8,20,23-tetraazabicyclo[8.7.6]tricos-16-ene-3,6,9,19,22-pentaone (9B)

To a vigorously stirred solution of 12 (254 mg, 1.0 mmol) in $CH_2Cl_2$/MeOH (9:1, 230 mL) was added dropwise a solution of bis-trityl 8B (105 mg, 0.10 mmol) over 30 minutes. After a further 30 min the reaction was quenched by the addition of sodium thiosulfate (0.05M, 100 mL) followed by brine (10 mL). The organic phase was separated and the aqueous phase extracted with $CH_2Cl_2$ (3×15 mL). The combined organic phase was dried ($MgSO_4$), filtered, and concentrated in vacuo to give a white solid. Purification by column chromatography on silica gel (1-3.5% MeOH/$CH_2Cl_2$) gave bicyclic depsipeptide 9B (43 mg, 0.08 mmol, 75%) as a white solid: $[α]^{25}_D$ −98 (c 0.05, 1:1 MeOH/$CHCl_3$); IR $v_{max}$ 3280, 1732, 1627, 1538, 1445 $cm^{-1}$; $^1$H-NMR (400 MHz, 19:1 $CD_3OD/CDCl_3$) δ 7.35-7.18 (m, 5H), 5.86-5.76 (m, 1H), 5.74-5.66 (m, 2H), 4.62 (dd, J=11.3, 4.0 Hz, 1H), 4.45 (dd, J=9.3, 5.3 Hz, 1H), 4.28 (d, J=17.6 Hz, 1H), 3.77 (d, J=17.6 Hz, 1H), 3.39 (d, J=10.5 Hz, 1H), 3.27-3.17 (m, 2H), 3.11-2.99 (m, 3H), 2.97-2.83 (m, 2H), 2.81 (dd, J=13.6, 2.0 Hz, 1H), 2.70-2.53 (m, 3H), 0.96 (d, J=6.5 Hz, 3H), 0.92 (d, J=6.5 Hz, 3H); $^{13}$C-NMR (100 MHz, 19:1 $CD_3OD/CDCl_3$) δ 173.8 (C), 173.2 (C), 172.9 (C), 171.3 (C), 169.4 (C), 137.7 (CH), 131.3 (CH), 131.3 (CH), 129.7 (CH), 129.6 (CH), 128.0 (CH), 71.9 (CH), 65.9 (CH), 58.3 (CH), 58.1 (CH), 42.6 ($CH_2$), 39.3 (2×$CH_2$), 36.9 ($CH_2$), 36.8 ($CH_2$), 31.8 ($CH_2$), 28.1 (CH), 20.6 ($CH_3$), 20.5 ($CH_3$); LRMS ($ES^+$) m/z 580 (50%, $[2M+Na]^+$), 563 (100%, $[M+NH_4]^+$), 563 (10% $[M+H]^+$).

Preparation of ((R)-2-{(S)-2-[(R)-2-(9H-fluoren-9-ylmethoxycarbonylamino)-3-methyl-butyrylamino]-3-tritylsulfanyl-propionylamino}-3-methyl-butyrylamino)-acetic acid methyl ester (4C)

To a stirred solution of 3A (836 mg, 1.11 mmol) in $CH_3CN$/$CH_2Cl_2$ (1:1, 60 mL) at RT was added $Et_2NH$ (3 mL). After stirring for 3 h at RT the reaction mixture was diluted with heptane (60 mL) and concentrated to give the crude amine as a colourless oil. To a stirred solution of Fmoc-D-valine (577 mg, 1.7 mmol) in $CH_2Cl_2$ (40 mL) was added EDAC.HCl (326 mg, 1.7 mmol), HOBt (230 mg, 1.7 mmol) and DIEA (627 μl, 3.6 mmol). After stirring at RT for 10 minutes a solution of the crude amine in $CH_2Cl_2$ (20 mL) was then added and the reaction mixture stirred for 12 h. Whereupon the reaction was washed with water (15 mL), 10% HCl (15 mL), 5% $NaHCO_3$ (15 mL) and sat NaCl (15 mL) solutions, dried ($Na_2SO_4$), filtered, and the solvent removed to give an off white solid which was recrystallised from $CH_3CN$ to give 4C as a white solid (734 mg, 0.86 mmol, 78%): $^1$H-NMR (400 MHz, $CDCl_3$) δ 7.74 (d, J=7.5 Hz, 2H), 7.53 (t, J=7.5 Hz, 2H), 7.42-7.32 (m, 9H), 7.30-7.19 (m, 9H), 7.16 (t, J=7.0 Hz, 2H), 6.80 (d, J=8.0 Hz, 1H), 6.57 (d, J=7.0 Hz, 1H), 5.52 (d, J=8.0 Hz, 1H), 4.44 (t, J=8.0 Hz, 1H), 4.38 (dd, J=10.5, 7.5 Hz, 1H), 4.25 (dd, J=10.5, 7.0 Hz, 1H), 4.17-3.95 (m, 3H), 3.87 (dd, J=18.1, 5.5 Hz, 1H), 3.78 (dd, J=18.1, 5.5 Hz, 1H), 3.63 (s, 3H), 2.71 (dd, J=12.5, 6.0 Hz, 1H), 2.53 (dd, J=12.5, 6.0 Hz, 1H), 2.21 (sept, J=6.4 Hz, 1H), 2.07-1.93 (m, 1H), 0.93-0.83 (m, 12H); $^{13}$C NMR 100 MHz 171.5 (C), 171.1 (C), 170.2 (2×C), 156.6 (C), 144.4 (C), 144.0 (C), 143.8 (C), 141.4 (C), 129.6 (CH), 128.3 (CH), 127.9 (CH), 127.2 (CH), 127.1 (CH), 125.2 (CH), 120.1 (CH), 67.3 ($CH_2$), 67.2 (C), 60.3 (CH), 58.5 (CH), 52.5 (CH), 52.3 (CH), 47.3 (CH), 41.0 ($CH_2$), 33.8 ($CH_2$), 31.5 (CH), 30.5 (CH), 19.2 (2×$CH_3$), 18.0 ($CH_3$), 17.8 ($CH_3$); LRMS ($ES^+$) m/z 1832 (10%, $[2M+Na]^+$), 877.5 (100%, $[M+Na]^+$).

Preparation of ((R)-2-{(S)-2-[(R)-2-((E)-(S)-3-hydroxy-7-tritylsulfanyl-hept-4-enoylamino)-3-methyl-butyrylamino]-3-tritylsulfanyl-propionylamino}-3-methyl-butyrylamino)-acetic acid methyl ester (6C)

To a stirred solution of 4C (235 mg, 0.28 mmol) in $CHCl_3$/$CH_3CN$ (1:1, 14 mL) at RT was added $Et_2NH$ (1 mL). After stirring for 5 h at RT the reaction mixture was diluted with heptane (10 mL) and solvent removed to give the crude amine as a colourless oil. To a stirred solution of the crude amine in $CH_2Cl_2$ (10 mL) was added a solution of 5 (193 mg, 0.34 mmol) in $CH_2Cl_2$ (5 mL) and DMAP (4 mg, 0.034 mmol) at RT. After stirring at RT for 12 hours, the solvent was removed and the residue was purified by flash chromatography (eluent 1-3% MeOH/$CH_2Cl_2$) to give 6C (230 mg, 81%) as a white solid: $^1$H NMR (400 MHz, $CDCl_3$) δ 7.42-7.38 (m, 12H), 7.30-7.14 (m, 20H), 6.74 (br s, 1H), 6.39 (br s, 1H), 5.49 (dtd, J=15.3, 6.5, 0.8 Hz, 1H), 5.36 (dd, J=15.3, 6.3 Hz, 1H), 4.39-4.26 (m, 3H), 4.16-4.06 (m, 1H), 3.83 (d, J=5.5 Hz, 2H), 3.65 (s, 3H), 3.33 (br s, 1H), 2.60 (dd, J=12.8, 7.3 Hz, 1H), 2.54 (dd, J=12.8, 6.8 Hz, 1H), 2.37 (dd, J=14.0, 3.0 Hz, 1H), 2.30-2.02 (m, 7H), 0.90 (d, J=7.0 Hz, 3H), 0.89 (d, J=7.0 Hz, 3H), 0.88 (d, J=7.0 Hz, 3H), 0.85 (d, J=7.0 Hz, 3H); $^{13}$C NMR (100 MHz, CDCl$_3$) δ 172.1 (C), 171.4 (C), 171.2 (C), 170.5 (C), 170.3 (C), 145.0 (C), 144.3 (C), 132.6 (CH), 130.2 (CH), 129.7 (CH), 129.5 (CH), 128.3 (CH), 128.0 (CH), 127.1 (CH), 126.8 (CH), 69.8 (CH), 67.1 (C), 66.8 (C), 59.0 (CH), 58.9 (CH), 52.5 (CH), 52.3 (CH$_3$), 43.9 (CH$_2$), 41.0 (CH$_2$), 33.7 (CH$_2$), 31.5 (2×CH$_2$), 30.4 (CH), 30.2 (CH$_2$), 19.5 (CH$_3$), 19.3 (CH$_3$), 17.9 (2×CH$_3$); LRMS (ES$^+$) m/z 1056 (100%, [M+Na]$^+$), 1051 (50%, [M+NH$_4$]$^+$).

Preparation of (6R,9S,12R,16S)-6,12-diisopropyl-16-((E)-4-tritylsulfanyl-but-1-enyl)-9-tritylsulfanyl-methyl-1-oxa-4,7,10,13-tetraaza-cyclohexadecane-2,5,8,11,14-pentaone (8C)

At 0° C. to a solution of methyl ester 6B (220 mg, 0.21 mmol) in THF (12 mL) was added a solution of LiOH (7.6 mg, 0.32) in H$_2$O (2 mL). After 1 h the reaction was quenched by addition of 1 M HCl (6 mL). CHCl$_3$ (50 mL) was added and the organic phase separated, extracting with CHCl$_3$ (2×15 mL). The organic phase was washed with brine (10 mL), dried (MgSO$_4$), filtered, and concentrated in vacuo to give the crude acid 7C (217 mg, quantative) as a white solid that was used immediately in the next step: (ES$^-$) m/z 1017 (100%, [M–H]$^-$).

To a solution of MNBA (90 mg, 0.26 mmol) and DMAP (62 mg, 0.51 mmol) in CH$_2$Cl$_2$ (50 mL) was added dropwise a solution of acid 7C (217 mg, 0.21 mmol) in CH$_2$Cl$_2$/THF (15:1, 200 mL) over 3 h (Nb. dissolve acid in THF first then add CH$_2$Cl$_2$). After a further 14 h the reaction was quenched by the addition of 1 M HCl (40 mL). The organic phase was separated (extracting with CH$_2$Cl$_2$) and washed sequentially with NaHCO$_3$ (30 mL) and brine (20 mL). The combined organic phase was dried (MgSO$_4$), filtered, and concentrated in vacuo to give a yellow oil. Purification by column chromatography on silica gel (30-70% EtOAc/CH$_2$Cl$_2$) gave 8C (130 mg, 0.13 mmol, 62%) as a white solid: $^1$H-NMR (400 MHz, CDCl$_3$) δ 7.88 (br s, 2H), 7.42-7.34 (m, 12H), 7.29-7.14 (m, 19H), 6.20 (br d, J=7.0 Hz, 1H), 5.62-5.50 (m, 2H), 5.31 (dd, J=15.3, 6.4 Hz, 1H), 4.36 (dd, J=17.3, 8.3 Hz, 1H), 4.24 (dd, J=8.5, 4.5 Hz, 1H), 4.11 (t, J=7.3 Hz, 1H), 3.65-3.56 (m, 1H), 3.42 (d, J=14.5 Hz, 1H), 2.99 (t, J=10.8 Hz, 1H), 2.64 (dd, J=12.0, 6.3 Hz, 1H), 2.50 (dd, J=15.1, 2.5 Hz, 1H), 2.35 (dd, J=14.8, 9.8 Hz, 1H), 2.17 (t, J=7.5 Hz, 2H), 2.06-1.86 (m, 3H), 1.84-1.72 (m, 1H), 0.91 (d, J=6.8 Hz, 3H), 0.88 (d, J=6.3 Hz, 6H), 0.83 (d, J=6.8 Hz, 3H); $^{13}$C-NMR (100 MHz, CDCl$_3$) δ 173.8 (C), 172.2 (C), 171.0 (C), 169.5 (C), 168.9 (C), 145.0 (C), 144.4 (C), 132.7 (CH), 129.7 (CH), 128.2 (CH), 128.1 (CH), 128.0 (CH), 127.0 (CH), 126.8 (CH), 72.2 (CH), 67.3 (C), 66.8 (C), 58.8 (CH), 58.7 (CH), 58.4 (CH), 42.1 (CH$_2$), 41.9 (CH$_2$), 32.0 (CH$_2$), 31.5 (CH$_2$), 31.3 (CH$_2$), 31.2 (CH$_2$), 29.4 (CH), 19.6 (CH$_3$), 19.4 (CH$_3$) 18.5 (CH$_3$), 17.0 (CH$_3$); LRMS (ES$^+$) m/z 1023 (100%, [M+Na]$^+$), 1018 (60%, [M+NH$_4$]$^+$).

Preparation of (E)-(1S,7R,10S,21R)-7,21-diisopropyl-2-oxa-12,13-dithia-5,8,20,23-tetraaza-bicyclo[8.7.6]tricos-16-ene-3,6,9,19,22-pentaone (9C)

To a vigorously stirred solution of 12 (305 mg, 1.2 mmol) in CH$_2$Cl$_2$/MeOH (9:1, 280 mL) was added dropwise a solution of bis-trityl 8C (120 mg, 0.12 mmol) over 30 minutes. After a further 30 min the reaction was quenched by the addition of sodium thiosulfate (0.05M, 100 mL) followed by brine (10 mL). The organic phase was separated and the aqueous phase extracted with CH$_2$Cl$_2$ (3×15 mL). The combined organic phase was dried (MgSO$_4$), filtered, and concentrated in vacuo to give a white solid. Purification by column chromatography on silica gel (1-4% MeOH/CH$_2$Cl$_2$) gave bicyclic depsipeptide 9C (60 mg, 0.12 mmol, 97%) as a white solid: [α]$^{25}_D$ –105.7 (1:1 MeOH/CHCl$_3$, c 0.15); $^1$H-NMR (400 MHz, CD$_3$OD) δ 5.76-5.63 (m, 3H), 4.52 (dd, J=11.3, 4.7 Hz, 1H), 3.96 (d, J=5.1 Hz, 1H), 3.74 (d, J=17.5 Hz, 1H), 3.38 (d, J=10.9 Hz, 1H), 3.19-3.11 (m, 2H), 3.09-2.96 (m, 3H), 2.90 (dd, J=13.6, 2.5 Hz, 1H), 2.71-2.62 (m, 2H), 2.58-2.44 (m, 1H), 2.31-2.18 (m, 1H), 1.11 (d, J=7.0 Hz, 3H), 1.09 (d, J=7.0 Hz, 3H), 1.01 (d, J=6.6 Hz, 3H), 0.91 (d, J=6.6 Hz, 3H); $^{13}$C-NMR (100 MHz, CD$_3$OD) δ 171.8 (C), 171.7 (C), 170.7 (C), 170.4 (C), 168.3 (C), 130.0 (CH), 129.6 (CH), 69.8 (CH), 64.6 (CH), 61.9 (CH), 54.8 (CH), 42.2 (CH$_2$), 39.3 (CH$_2$), 37.5 (CH$_2$), 37.1 (CH$_2$), 32.1 (CH$_2$), 29.2 (CH), 27.3 (CH), 20.6 (CH$_3$), 20.0 (CH$_3$), 19.4 (CH$_3$), 19.0 (CH$_3$); LRMS (ES$^+$) m/z 537 (100%, [M+Na]$^+$), 515 (90%, [M+H]$^+$).

Preparation of ((R)-2-{(S)-2-[(R)-6-tert-Butoxycarbonylamino-2-(9H-fluoren-9-ylmethoxycarbonylamino)-hexanoylamino]-3-tritylsulfanyl-propionylamino}-3-methyl-butyrylamino)-acetic acid methyl ester (4D)

The tripeptide 3A (548 mg, 0.7 mmol) under argon was dissolved in CH$_2$Cl$_2$/CH$_3$CN (44 mL, 1:1), then with stirring diethylamine (1.65 mL, 16 mmol) was added and the reaction mixture was stirred at room temperature for 4.5 h. Hexane (100 mL) was then added to the reaction mixture and the solvent was removed in vacuo, this was repeated again with hexane (3×25 mL). The crude amine was then dried under high vacuum for 40 mins. Then to a solution of PyBop (558 mg, 1.1 mmol) and Fmoc-D-Lysine(Boc)-OH (477 mg, 1 mmol) in CH$_3$CN (16.5 mL) was added diisopropylethylamine (0.45 mL, 2.6 mmol) under argon with stirring. The resultant deprotected amine of 3 was added in CH$_2$Cl$_2$ (19 mL) and the reaction mixture stirred at room temperature for 16 h. The solvent was then removed in vacuo and the solid formed was purified by column chromatography on silica gel (eluent 6:4 EtOAc/Hexane to give 4D (571 mg, 0.57 mmol, 81%) as a white solid: R$_f$ 0.17 EtOAc/Hexane (6:4): [α]$_D^{26}$=+47 (c 0.3, MeOH); IR 3294, 1744, 1646, 1515, 1445 (m); $^1$H NMR (400 MHz, CDCl$_3$) δ 7.74 (d, J=8.0, 2H), 7.56-7.51 (m, 2H), 7.42-7.34 (m, 8H), 7.30-7.17 (m, 11H), 7.02 (br s, 1H), 6.94 (br s, 1H), 6.59 (d, J=8.03 Hz, 1H), 5.75 (s, 1H), 4.38-4.21 (m, 2H), 4.18 (dd, J=8.5, 6.0 Hz, 1H), 4.15-4.05 (m, 2H), 3.87 (d, J=5.5 Hz, 3H), 3.55 (s, 3H), 3.03 (br d, J=8.0 Hz, 2H), 2.76-2.67 (m, 1H), 2.66-2.58 (m, 1H), 2.20-2.10 (m, 1H), 1.93-1.84 (m, 2H), 1.82-1.72 (m, 1H), 1.70-1.59 (m, 1H), 1.43 (s, 9H), 1.50-1.30 (m, 3H), 0.89 (d, J=7.02 Hz, 3H), 0.84 (d, J=7.03 Hz, 3H), $^{13}$C NMR (100 MHz, CDCl$_3$) δ 172.6 (C), 171.4 (C), 170.6 (C), 170.6 (C), 156.6 (C), 156.3 (CO), 144.4 (C), 144.3 (C), 143.9 (C), 143.8 (C), 141.4 (C), 129.7 (CH), 129.5 (CH), 128.3 (CH), 128.2 (CH), 127.2 (CH), 127.1 (CH), 125.2 (CH), 120.0 (CH), 67.4 (CH$_2$), 47.2 (CH$_3$), 41.1 (CH$_2$), 40.0 (CH$_2$), 33.5 (CH$_2$), 31.9 (CH$_2$), 30.3 (CH$_2$), 29.8 (CH), 28.6 (CH$_3$), 22.5 (CH$_2$), 19.4 (CH$_3$), 17.9 (CH$_3$), 52.3 (CH), 52.8 (CH), 55.1 (CH), 59.0 (CH); LRMS (ES$^+$) 1007.0 (100%, [M+Na]$^+$).

Preparation of ((R)-2-{(S)-2-[(R)-6-tert-Butoxycarbonylamino-2-((S)-3-hydroxy-7-tritylsulfanyl-hept-4-enoylamino)-hexanoylamino]-3-tritylsulfanyl-propionylamino}-3-methyl-butyrylamino)-acetic acid methyl ester (6D)

To a solution of tetrapeptide 4D (201 mg, 0.2 mmol) in $CH_2Cl_2$ (13.5 mL) and $CH_3CN$ (16.5 mL) was added triethylamine (1 mL, 9.6 mmol) under argon and the reaction mixture was stirred for 5 h. The solvent was then removed in vacuo and this was repeated with hexane (2×10 mL). Then to a solution of the crude amine in $CH_2Cl_2$ (7 mL) was added DMAP (4 mg, 0.03 mmol) followed by a solution of 5 (158 mg, 0.28 mmol) in $CH_2Cl_2$ (7 mL). The reaction was then stirred for 18 h. The solvent was then removed in vacuo and the solid formed was purified by column chromatography on silica gel (eluent 6:4-7:3 EtOAc/Hexane) to give 6D (136 mg, 0.12 mmol, 60%) as a white solid: mp 85-87° C.; $R_f$ 0.29 EtOAc/Hexane (8:2); $[\alpha]^{29}_D$=+19 (c 0.49, $CH_2Cl_2$); IR (thin film) 3289, 1751, 1687, 1634, 1521, 1490, 1443; $^1$H NMR (400 MHz, $CDCl_3$) δ 7.42-7.35 (m, 15H), 7.29-7.16 (m, 17H), 6.95 (d, J=7.5 Hz, 1H), 6.80 (d, J=8.0 Hz, 1H), 5.48 (dt, J=15.1, 6.5 Hz, 1H), 5.35 (dd, J=15.1, 6.0 Hz, 1H), 4.65 (s, 1H), 4.46-4.35 (m, 2H), 4.21 (dd, J=8.5, 6.52 Hz, 1H), 4.04-3.96 (m, 1H), 3.93 (d, J=5.5 Hz, 1H), 3.89-3.81 (m, 2H), 3.62 (s, 3H), 3.02 (d, J=5.5 Hz, 2H), 2.60-2.45 (m, 2H), 2.35-2.00 (m, 9H), 1.85-1.74 (m, 1H), 1.66-1.54 (m, 1H), 1.40 (s, 9H), 1.47-1.25 (m, 2H), 0.88 (d, J=7.0 Hz, 3H), 0.84 (d, J=7.0 Hz, 3H), $^{13}$C NMR (100 MHz, $CDCl_3$) δ 172.3 (C), 172.2 (C), 171.5 (C), 170.7 (C), 170.5 (C), 156.2 (C), 145.0 (C), 145.0 (C), 144.3 (C), 132.9 (CH), 129.7 (CH), 129.6 (CH), 129.5 (CH), 129.5 (CH), 128.2 (CH), 128.2 (CH), 128.0 (CH), 127.0 (CH), 126.7 (CH), 69.5 (CH), 67.1 ($CH_2$), 66.7 ($CH_2$), 58.6 (CH), 52.9 (CH), 52.6 (CH), 52.3 (CH), 52.2 ($CH_3$), 44.2 ($CH_2$), 41.1 ($CH_2$), 40.1 ($CH_2$), 33.9 ($CH_2$), 31.4 ($CH_2$), 31.0 ($CH_2$), 31.0 ($CH_2$), 30.6 (CH), 29.8 ($CH_2$), 28.6 ($CH_3$), 22.6 ($CH_2$), 19.3 ($CH_3$), 18.0 ($CH_3$), MS (ES$^+$) 1185 (100%, [M+Na]$^+$), 1163 (40%, [M+H]$^+$).

Preparation of {4-[(6R,9S,12R)-6-isopropyl-2,5,8,11,14-pentaoxo-16-((S)-4-tritylsulfanyl-but-1-enyl)-9-tritylsulfanylmethyl-1-oxa-4,7,10,13-tetraaza-cyclohexadec-12-yl]-butyl}-carbamic acid tert-butyl ester (8D)

At 0° C. to a solution of 6D (136 mg, 0.12 mmol) in THF (1.9 mL) was added a solution of LiOH (6.8 mg, 0.28 mmol) in water (0.5 mL) and the reaction mixture stirred for 55 mins. Then citric acid was added dropwise until the pH was lowered to between 3-4 then water was added (3.7 mL) followed by EtOAc (15 mL). The layers were separated and product was extracted with EtOAc (2×10 mL). The combined organic layers were then washed with sat. brine (10 mL), dried over $MgSO_4$ and the solvent was removed in vacuo to give the crude acid 7D (132 mg, quantitative) as a white solid that was used immediately in the next step: LRMS (ES$^-$) 1147 (100%, [M−H]$^-$).

Then to a solution of MNBA (47 mg, 0.14 mmol) and DMAP (33 mg, 0.27 mmol) in $CH_2Cl_2$ (25 mL) was added dropwise a solution of the acid 7D (132 mg, 0.11 mmol) in $CH_2Cl_2$ (96 mL) over 10 h and the reaction mixture stirred for another 9.5 h at room temperature. Then 0.2% HCl (50 mL) was added and the layers formed were separated, the organic layer was washed with sodium hydrogen sulfate (30 mL) and sat. brine (30 mL) dried over $MgSO_4$ and concentrated in vacuo to give a brown solid. This was then purified by flash column chromatography with an eluent of EtOAc/Hexane (6:4) which was increased to (3:1) gave the product 8D (52 mg, 0.05 mmol, 42%) as a white solid: $R_f$ 0.07 EtOAc/Hexane (6:4); $[\alpha]^{25}_D$=−76 (c 0.1, $CH_2Cl_2$); IR (thin film) 3271 1739 (m), 1683, 1641, 1536, 1490, 1444, 1391; $^1$H NMR (400 MHz, $CDCl_3$) δ 7.54 (s, 1H), 7.44-7.36 (m, 12H), 7.30-7.17 (m, 19H), 6.80 (d, J=8.5 Hz, 1H), 6.47 (d, J=8.5 Hz, 1H), 5.58 (dt, J=15.1, 7.0 Hz, 1H), 5.47 (td, J=6.5, 2.5 Hz, 1H), 5.39 (dd, J=15.1, 6.5 Hz, 1H), 4.68 (s, 1H), 4.29 (q, J=7.0 Hz, 1H), 4.20 (dd, J=17.1, 7.5 Hz, 1H), 4.16 (dd, J=9.0, 6.0 Hz, 1H), 3.53 (dd, J=17.1, 5.5 Hz, 1H), 3.44 (q, J=7.5 Hz, 1H), 3.00-2.90 (m, 2H), 2.66 (d, J=7.5 Hz, 2H), 2.55-2.48 (m, 1H), 2.39 (dd, J=15.1, 8.0 Hz, 1H), 2.30-2.15 (m, 3H), 2.13-2.01 (m, 4H), 1.68-1.58 (m, 1H), 1.51 (dd, J=13.5, 7.0 Hz, 1H), 1.40 (s, 9H), 1.45-1.34 (m, 2H), 1.36-1.28 (m, 2H), 1.31-1.23 (m, 2H), 0.89 (d, J=6.5 Hz, 3H), 0.84 (d, J=6.5 Hz, 3H), $^{13}$C NMR (100 MHz, $CDCl_3$) δ 173.1 (C), 171.3 (C), 171.3 (C), 169.8 (C), 168.9 (C), 156.2 (C), 145.0 (C), 144.5 (C), 132.6 (CH), 129.7 (CH), 128.2 (CH), 128.0 (CH), 127.0 (CH), 126.8 (CH), 79.1 (CH), 67.5 (C), 66.8 (C), 58.7 (CH), 53.1 (CH), 53.0 (CH), 42.0 ($CH_2$), 41.8 ($CH_2$), 40.2 ($CH_2$), 32.2 ($CH_2$), 31.5 ($CH_2$), 31.4 ($CH_2$), 31.2 ($CH_2$), 31.0 ($CH_2$), 29.7 (CH), 28.6 ($CH_3$), 22.8 ($CH_2$), 19.5 ($CH_3$), 17.6 ($CH_3$); LRMS (ES$^+$) 1152 (100%, [M+Na]$^+$]).

Preparation of [4-((7R,10S,14S,21R)-7-isopropyl-3,6,9,19,22-pentaoxo-2-oxa-12,13-dithia-5,8,20,23-tetraaza-bicyclo[8.7.6]tricos-16-en-21-yl)-butyl]-carbamic acid tert-butyl ester (9D)

To a stirred solution of iodine (117 mg, 0.5 mmol) in $CH_2Cl_2$/MeOH (9:1) (148 mL) was added dropwise a solution of 8D (52 mg, 0.05 mmol) in $CH_2Cl_2$/MeOH (9:1) (77 mL) over 30 mins, the reaction mixture was then allowed to stir for a further 30 mins after which time sodium thiosulfate (128 mL, 0.02 M) was added. The layers were separated and the product was extracted with $CH_2Cl_2$ (3×25 mL), dried over $MgSO_4$, and the solvent was removed in vacuo. Purification was then carried out by column chromatography on silica gel (eluent 2:98-8:92 MeOH/$CH_2Cl_2$) which gave 9D (3 mg, 0.005 mmol, 10%) as a white solid: $R_f$ 0.05 MeOH/$CH_2Cl_2$ (5:95), LRMS (ES$^+$) 666.8 (100%, [M+Na]$^+$).

Preparation of (R)-2-((R)-2-{(R)-2-[(R)-2-((E)-(S)-3-Hydroxy-9,9,9-triphenyl-non-4-enoylamino)-propionylamino]-5,5,5-triphenyl-pentanoylamino}-3-methyl-butyrylamino)-propionic acid methyl ester (6E)

To a solution of $H_2$N-D-Ala-D-Cys(STrt)-D-Val-D-Ala-OMe (96 mg, 0.155 mmol, purchased from Biopeptide Co., CA 92121-1510, USA, 60% purity) in $CH_2Cl_2$/THF (1:1, 30 mL) was added a solution of 5 (87 mg, 0.155 mmol) in $CH_2Cl_2$ (5 mL) followed by DMAP (2 mg, 0.02 mmol). After 18 h the reaction mixture was concentrated in vacuo. Purification by column chromatography on silica gel (1-3.5% MeOH/$CH_2Cl_2$) gave bis-trityl 6E (55 mg, 0.054 mmol, 35%) as a white solid with low solubility: LRMS (HPLC ES$^+$ using an XTerra MS $C_{18}$ column with 5 μm particle size, 3.0×50 mm, linear gradient 5% methanol (0.1% HCOOH)/$H_2O$ to 100% over 5 min at 1.25 mL/min. Then 100% methanol (0.1% HCOOH) for 5 min at 1.5 mL/min) rt=7.93 min, m/z 1041.7 (100%, [M+Na]$^+$), 1019.7 (30%, [M+H]$^+$).

Preparation of (3R,6R,9S,12R,16S)-6-isopropyl-3,12-dimethyl-16-((E)-4-tritylsulfanyl-but-1-enyl)-9-tritylsulfanylmethyl-1-oxa-4,7,10,13-tetraaza-cyclohexadecane-2,5,8,11,14-pentaone (8E)

At 0° C. to a solution of methyl ester 6E (81 mg, 0.080 mmol) in THF (5 mL) was added a solution of LiOH (3 mg, 0.12) in H₂O (0.8 mL). After 1 h the reaction was quenched by addition of 1 M HCl (10 mL). CHCl₃ (20 mL) was added and the organic phase separated, extracting with CHCl₃ (2×10 mL). The organic phase was washed with brine (15 mL), dried (MgSO₄) and concentrated in vacuo to give the crude acid 7E (80 mg, quantative) as a white solid that was used immediately in the next step: LRMS (ES⁻) m/z 1003 (100%, [M−H]⁻).

To a solution of MNBA (35 mg, 0.10 mmol) and DMAP (25 mg, 0.20 mmol) in CH₂Cl₂ (20 mL) was added dropwise a solution of acid 7E (80 mg, 0.080 mmol) in CH₂Cl₂/THF (75:5, 80 mL) over 3 h. After a further 14 h the reaction was quenched by the addition of 1 M HCl (25 mL). The organic phase was separated (extracting with CH₂Cl₂) and washed sequentially with NaHCO₃ (30 mL) and brine (20 mL). The combined organic phase was dried (MgSO₄) and concentrated in vacuo to give a yellow oil. Purification by column chromatography on silica gel (70-100% EtOAc/CH₂Cl₂) gave 8E (34 mg, 0.035 mmol, 43%) as a white solid: ¹H-NMR (400 MHz, CDCl₃) δ 7.49-7.08 (m, 33H), 6.31 (br s, 1H), 5.57 (dt, J=15.3, 6.5 Hz, 1H), 5.47 (q, J=6.1 Hz, 1H), 5.36 (dd, J=15.3, 6.8 Hz, 1H), 4.45 (quin, J=7.0 Hz, 1H), 4.21 (quin, J=7.0 Hz, 1H), 3.87 (t, J=7.3 Hz, 1H), 3.59 (br s, 1H), 2.92 (dd, J=12.5, 8.5 Hz, 1H), 2.55 (dd, J=12.5, 5.4 Hz, 1H), 2.51-2.36 (m, 2H), 2.17 (t, J=7.3 Hz, 2H), 2.05-1.86 (m, 3H), 1.36 (d, J=7.0 Hz, 3H), 1.33 (d, J=7.0 Hz, 3H), 0.88 (d, J=6.8 Hz, 3H), 0.83 (d, J=7.0 Hz 3H); ¹³C-NMR (100 MHz, CDCl₃) δ 173.6 (C), 170.8 (C), 170.4 (C), 170.2 (C), 169.7 (C), 144.9 (C), 144.4 (C), 132.9 (CH), 129.7 (CH), 129.6 (CH), 128.2 (CH), 128.1 (CH), 128.0 (CH), 127.0 (CH), 126.8 (CH), 72.0 (CH), 67.2 (C), 66.8 (C), 61.4 (CH), 55.3 (CH), 49.9 (CH), 49.5 (CH), 41.3 (CH₂), 32.4 (CH₂), 31.4 (CH₂), 31.3 (CH₂), 29.8 (CH), 19.8 (CH₃), 18.4 (CH₃), 17.9 (CH₃), 17.8 (CH₃); LRMS (ES⁺) m/z 1009 (100%, [M+Na]⁺), 987 (10%, [M+H]⁺).

Preparation of (E)-(1S,4R,7R,10S,21R)-7-isopropyl-4,21-dimethyl-2-oxa-12,13-dithia-5,8,20,23-tetraaza-bicyclo[8.7.6]tricos-16-ene-3,6,9,19,22-pentaone (9E)

To a solution of I₂ (87 mg, 0.34 mmol) in CH₂Cl₂/MeOH (9:1, 100 mL) was added dropwise a solution of bis-trityl 8E (34 mg, 0.034 mmol) over 30 minutes. After a further 30 min the reaction was quenched by the addition of sodium thiosulfate (0.05M, 25 mL) followed by brine (10 mL). The organic phase was separated and the aqueous phase extracted with CH₂Cl₂ (3×15 mL). The combined organic phase was dried (MgSO₄), filtered, before concentration in vacuo gave a white solid. Purification by column chromatography on silica gel (3-5% MeOH/CH₂Cl₂) gave cyclised depsipeptide 9E (10 mg, 0.02 mmol, 60%) as a white solid: [α]²⁵_D −51.8 (c 0.45, MeOH); ¹H-NMR (400 MHz, CDCl₃) δ 7.52 (d, J=6.5 Hz, 1H), 7.40 (d, J=6.3 Hz, 1H), 6.94 (d, J=9.5 Hz, 1H), 6.46 (d, J=3.0 Hz, 1H), 6.23-6.10 (m, 1H), 5.80-5.72 (m, 2H), 5.06 (ddd, J=10.0, 6.8, 3.7 Hz, 1H), 4.47 (quin, J=7.0 Hz, 1H), 4.20 (qd, J=7.3, 3.5 Hz, 1H), 3.81 (dd, J=14.3, 6.5 Hz, 1H), 2.96-2.77 (m, 3H), 2.76-2.64 (m, 5H), 2.61 (dd, J=13.5, 2.2 Hz, 1H), 1.49 (d, J=7.0 Hz, 3H), 1.48 (d, J=7.2 Hz, 3H), 0.95 (d, J=6.5 Hz, 3H), 0.93 (d, J=6.5 Hz, 3H); ¹³C-NMR (100 MHz, CD₃OD) δ 174.9 (C), 173.9 (C), 172.4 (C), 172.2 (C), 172.0 (C), 131.9 (CH), 131.1 (CH), 71.8 (CH), 67.2 (CH), 56.3 (CH), 53.0 (CH), 50.7 (CH), 40.4 (CH₂), 39.9 (CH₂), 39.3 (CH₂), 34.4 (CH₂), 28.7 (CH), 20.7 (CH₃), 20.3 (CH₃), 17.7 (CH₃), 16.4 (CH₃); LRMS (ES⁺) m/z 1024 (200%, [2M+Na]⁺), 523 (50%, [M+Na]⁺), 501 (100% [M+H]⁺).

Preparation of (R)-4-((E)-(S)-3-Hydroxy-7-tritylsulfanyl-hept-4-enoylamino)-4-{(S)-1-[(R)-1-(methoxycarbonylmethyl-carbamoyl)-2-methyl-propylcarbamoyl]-2-tritylsulfanyl-ethylcarbamoyl}-butyric acid tert-butyl ester (6F)

To a solution of H₂N-D-Glu(OʹBu)-D-Cys(STrt)-D-Val-Gly-OMe (145 mg, 0.2 mmol, purchased from Biopeptide Co., CA 92121-1510, USA, ~60% purity) in CH₂Cl₂ (40 mL) was added a solution of 5 (113 mg, 0.2 mmol) in CH₂Cl₂ (10 mL) followed by DMAP (2.5 mg, 0.02 mmol). After 18 h the reaction was concentrated in vacuo. Purification by column chromatography on silica gel (1-3% MeOH/CH₂Cl₂) gave 6F (97 mg, 0.087 mmol, 44%) as a white solid: ¹H-NMR (400 MHz, CDCl₃) δ 7.46-7.33 (m, 12H), 7.32-7.13 (m, 20H), 7.07 (br s, 1H), 6.77 (d, J=8.3 Hz, 1H), 5.46 (dt, J=15.3, 6.5 Hz, 1H), 5.34 (dd, J=15.3, 6.3 Hz, 1H), 4.40-4.23 (m, 3H), 4.11-3.86 (m, 2H), 3.79 (dd, J=17.8, 5.5 Hz, 1H), 3.70-3.58 (m, 1H), 3.64 (s, 3H), 3.06 (br s, 1H), 2.63 (dd, J=12.8, 7.5 Hz, 1H), 2.53 (dd, J=12.8, 5.8 Hz, 1H), 2.48-2.12 (m, 6H), 2.11-1.85 (m, 4H), 1.41 (s, 9H), 0.92 (d, J=6.7 Hz, 3H), 0.91 (d, J=6.7 Hz, 3H); ¹³C-NMR (100 MHz, CDCl₃) δ 173.7 (C), 172.3 (C), 171.6 (C), 171.3 (C), 170.4 (C), 170.3 (C), 145.0 (C), 144.3 (C), 133.6 (CH), 130.3 (CH), 129.7 (CH), 129.5 (CH), 128.2 (CH), 128.0 (CH), 127.1 (CH), 126.7 (CH), 81.5 (C), 70.0 (CH), 67.1 (C), 66.7 (C), 59.3 (CH), 54.6 (CH), 53.0 (CH), 52.2 (CH₃), 44.1 (CH₂), 41.0 (CH₂), 33.3 (CH₂), 32.2 (CH₂), 31.4 (CH₂×2), 29.9 (CH), 28.1 (CH₃), 26.1 (CH₂), 19.3 (CH₃), 17.7 (CH₃); LRMS (ES⁺) m/z 1142 (100%, [M+Na]⁺).

Preparation of 3-[(6R,9S,12R,16S)-6-Isopropyl-2,5,8,11,14-pentaoxo-16-((E)-4-tritylsulfanyl-but-1-enyl)-9-tritylsulfanylmethyl-1-oxa-4,7,10,13-tetraaaza-cyclohexadec-12-yl]-propionic acid tert-butyl ester (8F)

At 0° C. to a solution of methyl ester 6F (98 mg, 0.088 mmol) in THF (5 mL) was added a solution of LiOH (3 mg, 0.13) in H₂O (0.8 mL). After 1 h the reaction was quenched by addition of 1 M HCl (15 mL). CHCl₃ (20 mL) was added and the organic phase separated, extracting with CHCl₃ (2×10 mL). The organic phase was washed with brine (15 mL), dried (MgSO₄) and concentrated in vacuo to give the crude acid 7F (96 mg, quantative) as a white solid that was used immediately in the next step: (ES⁻) m/z 1103 (100%, [M−H]⁻).

To a solution of MNBA (36 mg, 0.10 mmol) and DMAP (25 mg, 0.21 mmol) in CH₂Cl₂ (20 mL) was added dropwise a solution of acid 7F (96 mg, 0.087 mmol) in CH₂Cl₂/THF (75:2, 77 mL) over 3 h. After a further 14 h the reaction was quenched by the addition of 1 M HCl (25 mL). The organic phase was separated (extracting with CH₂Cl₂) and washed sequentially with NaHCO₃ (30 mL) and brine (20 mL). The combined organic phase was dried (MgSO₄) and concentrated in vacuo to give a yellow oil. Purification by column chromatography on silica gel (50-70% EtOAc/CH₂Cl₂, then +0.1% MeOH) gave 8F (53 mg, 0.049 mmol, 56%) as a white solid: ¹H-NMR (400 MHz, CDCl₃) δ 7.44-7.32 (m, 12H), 7.31-7.15 (m, 19H), 7.11-7.03 (m, 2H), 6.68 (br s, 1H), 5.58 (dt, J=15.6, 6.5 Hz, 1H), 5.43 (ddd, J=9.5, 7.0, 3.0 Hz, 1H), 5.33 (dd, J=15.6, 7.0 Hz, 1H), 4.44 (dd, J=17.0, 9.6 Hz, 1H), 4.30 (dd, J=9.0, 4.5 Hz, 1H), 4.04 (q, J=7.0 Hz, 1H), 3.59 (m, 1H), 3.50 (dd, J=6.5, 2.0 Hz, 1H), 3.07 (t, J=11.0 Hz, 1H), 2.60-2.45 (m, 3H), 2.42-2.23 (m, 3H), 2.22-2.12 (m, 2H), 2.08-1.89 (m, 4H), 1.40 (s, 9H), 0.88 (d, J=7.0 Hz, 3H), 0.83 (d, J=7.0 Hz, 3H); $^{13}$C-NMR (100 MHz, CDCl$_3$) δ 173.4 (C), 172.6 (C), 171.1 (C), 170.9 (C), 170.0 (C), 169.0 (C), 145.0 (C), 144.3 (C), 133.2 (CH), 129.7 (CH), 129.6 (CH), 128.3 (CH), 128.0 (CH), 127.1 (CH), 126.8 (CH), 81.3 (C), 72.1 (CH), 67.3 (C), 66.8 (C), 58.7 (CH), 56.8 (CH), 54.1 (CH), 41.9 (CH$_2$), 41.3 (CH$_2$), 32.4 (CH$_2$), 31.8 (CH$_2$), 31.4 (CH$_2$), 31.2 (CH$_2$), 29.0 (CH), 28.2 (CH$_3$), 25.9 (CH$_2$), 19.7 (CH$_3$), 17.2 (CH$_3$); LRMS (ES$^+$) m/z 1109 (100%, [M+Na]$^+$), 1087 (50%, [M+H]$^+$).

Preparation of 3-((E)-(1S,7R,10S,21R)-7-Isopropyl-3,6,9,19,22-pentaoxo-2-oxa-12,13-dithia-5,8,20,23-tetraaza-bicyclo[8.7.6]tricos-16-en-21-yl)-propionic acid tert-butyl ester (9F)

To a solution of I$_2$ (117 mg, 0.46 mmol) in CH$_2$Cl$_2$/MeOH (9:1, 130 mL) was added dropwise a solution of bis-trityl 8F (50 mg, 0.046 mmol) over 30 minutes. After a further 30 min the reaction was quenched by the addition of sodium thiosulfate (0.05M, 50 mL) followed by brine (20 mL). The organic phase was separated and the aqueous phase extracted with CH$_2$Cl$_2$ (3×25 mL). The combined organic phase was dried (MgSO$_4$) before concentration in vacuo gave a white solid. Purification by column chromatography on silica gel (1-3% MeOH/CH$_2$Cl$_2$) gave bicyclic depsipeptide 9F (19 mg, 0.032 mmol, 69%) as a white solid: [α]$^{25}_D$ −76.7 (c 0.60, MeOH); $^1$H-NMR (400 MHz, CDCl$_3$) δ 8.15 (d, J=4.0 Hz, 1H), 7.35 (d, J=6.5 Hz, 1H), 7.23 (t, J=5.5 Hz, 1H), 7.11 (d, J=9.0 Hz, 1H), 6.05 (ddt, J=15.5, 7.0, 2.0 Hz, 1H), 5.84-5.73 (m, 2H), δ 4.97 (td, J=8.0, 4.5 Hz, 1H), 4.18-4.01 (m, 3H), 3.61 (dd, J=15.1, 8.0 Hz, 1H), 3.24 (dd, J=10.5, 6.5 Hz, 1H), 2.95-2.75 (m, 5H), 2.73-2.62 (m, 3H), 2.51 (dd, J=13.6, 2.0 Hz, 1H), 2.42 (ddd, J=18.0, 9.0, 3.5 Hz, 1H), 2.19-2.04 (m, 2H), 1.83 (s, 9H), 0.98 (d, J=6.5 Hz, 3H), 0.92 (d, J=6.5 Hz, 3H); $^{13}$C-NMR (100 MHz, CDCl$_3$) δ 175.7 (C), 171.8 (C), 171.7 (C), 170.9 (C), 169.9 (C), 168.2 (C), 130.2 (CH), 129.6 (CH), 82.6 (C), 69.4 (CH), 65.4 (CH), 57.6 (CH), 53.8 (CH), 42.4 (CH$_2$), 40.0 (2×CH$_2$), 38.6 (CH$_2$), 34.1 (CH$_2$), 33.1 (CH$_2$), 28.2 (CH$_3$), 27.4 (CH), 24.9 (CH$_2$), 20.6 (CH$_3$), 20.2 (CH$_3$); LRMS (ES$^+$) m/z 623 (90%, [M+Na]$^+$), 601 (100%, [M+H]$^+$).

Preparation of 3-((E)-(1S,7R,10S,21R)-7-Isopropyl-3,6,9,19,22-pentaoxo-2-oxa-12,13-dithia-5,8,20,23-tetraaza-bicyclo[8.7.6]tricos-16-en-21-yl)-propionic acid (10F)

To a solution of 9F (12 mg, 0.02 mmol) and Et$_3$SiH (10 μL, 0.06 mmol) in CH$_2$Cl$_2$ (1.5 mL) was added TFA (150 μL, 2.0 mmol). After 6 h the solvent was removed and the residue purified by column chromatography on silica gel (10% methanol/CH$_2$Cl$_2$ then +1% AcOH) to give 1° F. (5.6 mg, 0.01 mmol, 55%) as a white solid: [α]$^{25}_D$ −63.4 (c 0.25, MeOH); $^1$H-NMR (400 MHz, CD$_3$OD) δ 7.5 (1×NH observed, d, J=7.5 Hz, 1H), 5.81 (dddd, J=16.8, 6.8, 4.8, 2.5 Hz, 1H), 5.75-5.67 (m, 2H), 4.62 (ddd, J=11.0, 8.0, 5.5 Hz 1H), 4.28 (d, J=17.5 Hz, 1H), 4.15 (dd, J=9.0, 6.0 Hz, 1H), 3.78 (d, J=17.5 Hz, 1H), 3.43 (d, J=10.5 Hz, 1H), 3.20-3.10 (m, 2H), 3.07-3.00 (m, 2H), 2.94-2.81 (m, 1H), 2.82 (dd, J=13.2, 2.2 Hz, 1H), 2.73-2.50 (m, 4H), 2.38 (q, J=7.0 Hz, 1H), 2.23-1.99 (m, 2H), 0.98 (d, J=6.5 Hz, 3H), 0.92 (d, J=6.5 Hz, 3H); $^{13}$C-NMR (100 MHz, CD$_3$OD) δ 176.5 (C), 174.0 (C), 173.5 (C), 173.0 (C), 171.6 (C), 169.5 (C), 131.4 (CH), 131.3 (CH), 72.1 (CH), 66.0 (CH), 58.5 (CH), 57.0 (CH), 42.7 (CH$_2$), 39.7 (CH$_2$), 39.4 (CH$_2$), 36.8 (CH$_2$), 31.8 (CH$_2$), 31.6 (CH$_2$), 28.2 (CH$_3$), 26.6 (CH$_2$), 20.6 (CH$_3$), 20.5 (CH$_3$); LRMS (ES$^−$) m/z 543 (100%, [M−H]$^−$).

Results
Activity Assay 1

We compared the ability of Suberoylanilide hydroxamic acid (SAHA), a known HDAC inhibitor, and compound 001 (the compound of formula (2) on page 7) to inhibit the growth of MCF7 human breast cancer cells and normal human dermal fibroblasts (NHDF).

Method; Cell proliferation assays were performed using the CyQuant™ assay system (Molecular Probes, Inc. USA) according to the manufacturer's instructions. This system utilises a proprietary green fluorescent dye which undergoes strong fluorescent enhancement on binding cellular nucleic acids, to allow determination of cell number with a linear detection range between 50 to 250,000 cells. Estrogen receptor positive MCF7 breast cancer cells (ECAAC) and NHDF cells (Cambrex, UK) were plated in 96 well plates, at a density of 1000 cells in 100 μl of cell culture medium per well. Compounds were added a minimum of 5 hours later, in serial dilutions in cell culture medium, in 100 μl volumes at 2× final concentration. Six days later cell culture medium was removed by inversion of the plate onto blotting paper and cells were gently washed once with 200 μl PBS. Plates were frozen immediately for a minimum of one hour at −80° C. and then thawed. 200 μl of 1× CyQuant cell lysis buffer supplemented with dye, made according to the manufacturer's instruction, was added immediately to each well and incubated at room temperature for 3-5 minutes. Fluorescence was then measured for each well using a Cytofluor II Fluoresence Multiwell Plate Reader and CytoFluor II software with filters at 480 nm for excitation and 520 nm for emission maxima. Cell proliferation was determined for mean values of duplicate samples as percentages relative to untreated cell samples (=100%). Growth inhibition curves were used to derive IC$_{50}$ values.

Figure 1:
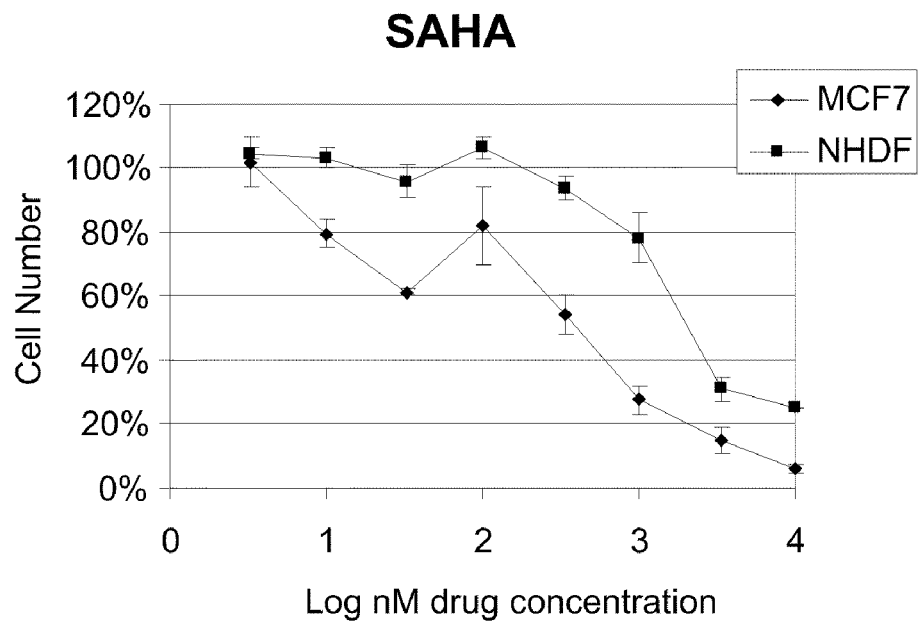
FIG. 1 shows the effect of compound 001 and SAHA on the growth of MCF7 and Normal Human Dermal Fibroblasts (NHDF). MCF7 and NHDF were incubated with the indicated concentrations of compounds. After 6 days cell growth relative to untreated cells (=100%) was determined using the CyQuant™ assay. Equivalent amounts of DMSO, as a solvent control, had no effect on cell growth (not shown). Data shown are mean ± standard deviation for duplicate determinations and are representative of multiple experiments.
Figure 1:
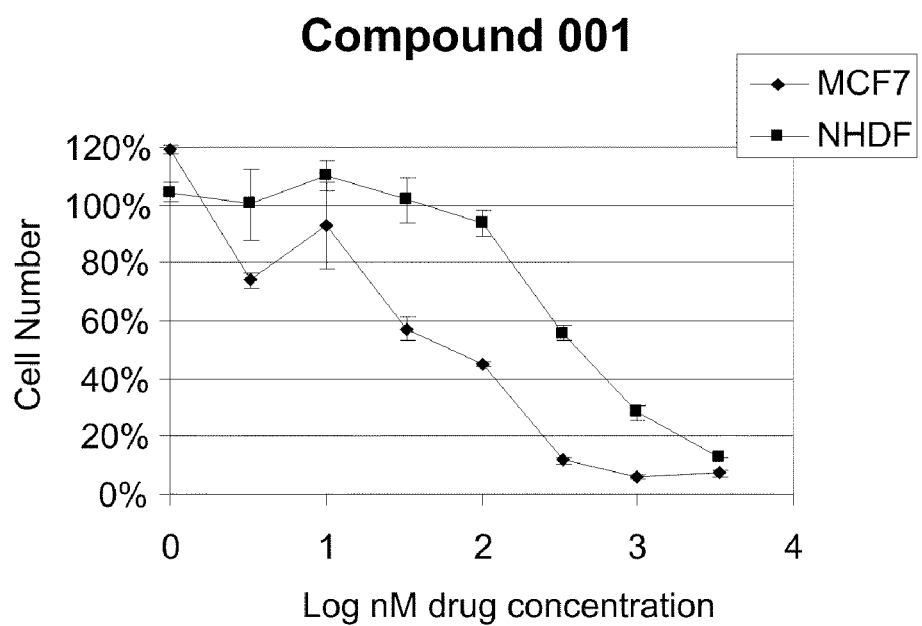

FIG. 1 shows the effect of compound 001 and SAHA on the growth of MCF7 and Normal Human Dermal Fibroblasts (NHDF). MCF7 and NHDF were incubated with the indicated concentrations of compounds. After 6 days cell growth relative to untreated cells (=100%) was determined using the CyQuant™ assay. Equivalent amounts of DMSO, as a solvent control, had no effect on cell growth (not shown). Data shown are mean±standard deviation for duplicate determinations and are representative of multiple experiments.

Results; Cell growth was inhibited by the compounds. Importantly, there were differences between the inhibitors and between cell types. The mean IC$_{50}$ for growth inhibition (±SD) was calculated from multiple experiments and are shown in Table 1 below.

TABLE 1

|  | Compound 001 | SAHA |
| --- | --- | --- |
| MCF7 | 121 ± 52 nM | 483 ± 109 nM |
| NHDF | 420 ± 42 nM | ~2000 nM$^a$ |

$^a$IC$_{50}$ calculated from single experiment performed in duplicate

Compound 001 was a potent inhibitor of cancer cell growth. Importantly, compound 001 was significantly more potent than SAHA (p=0.003, Student's t-test), currently in phase II trials. Both compounds were relatively more effective in MCF7 cells versus NHDF demonstrating selectivity towards malignant cells. Similar experiments performed using HUT78 T-cell leukaemia cells (performed as described above) demonstrated that Compound 001 also inhibited the growth of these cells (data not shown).

Activity Assay 2

We investigated whether compound 001 (the compound of formula (2) on page 7) activated the SV40 promoter, previously demonstrated to be responsive to HDAC-mediated repression.

Method. We generated a stable clone derived from MCF7 cells containing an integrated reporter construct with the SV40 immediate early promoter cloned upstream of the luciferase gene. MCF7 cells were transfected with pGL2-Basic (SV40/luciferase reporter) (Promega, UK) and pcDNA3 (expresses neomycin resistance gene) using Transfast transfection reagent. After 24 hours, cells were collected by trypsinisation and plated at low density. The following day, G418 was added to the growth medium. After ~21 days, individual drug-resistant colonies were isolated and cultured. We selected a clone (2.1.1 cells) which demonstrated high level of induction of luciferase activity following addition of an HDAC inhibitor for further study. To test the effects of compound 001, 2.1.1 cells were incubated with various concentrations of compound 001 or an equivalent amount of DMSO as a control. The following day, cells were collected and luciferase activity detected using the Promega luciferase assay system and a TopCount (Perkin-Elmer).

FIG. 2 shows the effect of compound 001 on the activity of the HDAC responsive SV40 promoter. MCF7 derived cells containing a stably integrated SV40 promoter-luciferase reporter plasmid were treated with the indicated concentrations of compound 001, or DMSO as a solvent control. Luciferase activity was determined after approx 16 hours. The data shown are derived from a single experiment performed in duplicate and are representative of multiple experiments.

Results; The experiment shows that compound 001 effectively reverses HDAC-mediated repression of the SV40 immediate early promoter.

Activity Assay 3

We investigated the effects of compound 001 (the compound of formula (2) on page 7) and SAHA on cell cycle distribution and survival in MCF7 cells Method; MCF7 cells were incubated with indicated concentrations of compounds, or left untreated as a control, for various times, as detailed in the figure legends. Cells were collected and the proportion of cells in different phases of the cell cycle determined using propidium iodide staining and flow cytometry as previously described (Purohit et al., Int J Ca 85, 584-9 2000). The proportion of cells with <G0/G1 content (pre G0) relative to total cells was calculated first. The proportion of cells in different cell cycle phases (G0/G1, S, G2/M) was calculated as a proportion of all cells in the cell cycle (i.e., total cells minus cells with <G0/G1 content).

FIG. 3 shows the effects of compound 001 and SAHA on cell cycle distribution and survival in MCF7 cells. MCF7 cells were incubated with the indicated concentrations of compounds (each equivalent to ~10×$IC_{50}$ values for growth inhibition), or DMSO as a solvent control, for 24, 48 or 72 hours. The proportion of cells in different phases of the cell cycle was determined by flow cytometry. Data shown are mean values ±SD, derived from two separate experiments, relative to untreated cells which are normalised to 1.

Results; The figure shows that at equivalent effective concentrations, compound 001 and SAHA induce a predominant G2/M phase arrest and cell death in MCF7 cells.

Activity Assay 4

We investigated the effects of compound 001 (the compound of formula (2) on page 7) on histone acetylation in MCF7 breast cancer cells and cardiac myocytes.

Method; Cardiac myocytes were prepared as described in Chembiochem. 2005 January; 6(1):162-70 and incubated with the indicated concentrations of compound 001 for 24 hours. MCF7 cells were incubated with the indicated concentrations of compound 001 for 24 hours. Expression of total histone H4 acetylation, or specific acetylation of Histone H4-K8 or Histone H3-K9 was analysed by Western blotting, as previously described (Brimmell et al. Br J Cancer. 1999 November; 81(6):1042-51) using antibodies from Upstate Biotech.

FIG. 4 shows the effect of compound 001 on Histone acetylation. (A) MCF7 cells were incubated with compound 001 for 24 hours. Histone H4 acetylation was measured by immunoblotting. (B) Cardiac myocytes were incubated with indicated compound 001 for 24 hours. Histone H4 acetylation was measured by immunoblotting. (C) MCF7 cells were incubated with compound 001 for 24 hours. Histone H3-K9 and Histone H4-K8 acetylation was measured by immunoblotting Results; The experiment shows that compound 001 induces the accumulation of acetylated histone H4 and specific Histone H3-K9 and Histone H4-K8 acetylation. We also demonstrated that Compound 001 increased the levels of acetylated histone H4 in primary chronic lymphocytic leukaemia cells (data not shown).

Activity Assay 5

We analysed the ability of compounds to inhibit in vitro HDAC activity. In vitro HDAC assays were performed using a HDAC fluorescent activity assay kit (Biomol, UK) according to the manufacturer's instructions. Compounds were reduced prior to analysis; 1 mM compound was reduced with 30 mM DTT in DMSO overnight at room temperature, protected from light. Reactions were then set up in a 96-well plate. For each reaction 10l compound (5× required concentration in assay buffer) was mixed with 15 μl diluted Hela Nuclear Extract (30-fold in assay buffer). Serial dilutions were set up for each compound. Reactions containing Hela extract only and assay buffer only were also set up. 25 μl diluted Fluor de Lys™ substrate (100-fold in assay buffer) was added to each reaction, which were then incubated at 37° C. for 1 hour. The reaction was stopped by addition of 50 μl Fluor de Lys™ Developer (20-fold dilution in assay buffer, plus TSA diluted 100-fold). The reactions were then incubated at room temperature for 10 minutes before fluorescence was measured using a CytoFluor II Fluorescence Multiwell Plate Reader and CytoFluor II software with filters set at 360 nM for excitation and 460 nM for emission. Inhibition of in vitro HDAC activity was determined for mean values of duplicate samples as percentages relative to HeLa extract only reactions. $IC_{50}$ values were calculated using GraphPad Prism software.

TABLE 2

Inhibition of HDAC activity

| Compound | Corresponding formula on page 7, 8 or 9 | $IC_{50}$ (nM) |
|---|---|---|
| SAHA | N/A | 330 |
| 9A | (2) | 9.9 |
| 9E | (3) | 87 |
| 9F | (4) | 8.0 |
| 10F | (5) | 1.7 |
| 9B | (6) | 25 |
| 9C | (7) | 9.9 |

Activity Assay 6

We analysed the ability of compounds to inhibit the in vitro growth of human cancer cells. Cell proliferation assays were performed using the CyQuant™ assay system (Molecular Probes, Inc. USA) according to the manufacturer's instructions. MCF7 breast, A2780 ovarian and PC3 and LNCAP prostate cancer cells were plated in 96 well plates, at a density of 1000 cells for MCF7 cells or 5000 cells for M780/PC3/LNCAP cells, in 100 μl of cell culture medium per well. Compounds were added a minimum of 5 hours later, in serial dilutions in cell culture medium, in 100 μl volumes at 2× final concentration. Cell culture medium was removed after 4 (A2780, PC3 or LNCAP cells) or 6 days (MCF7 cells) by inversion of the plate onto blotting paper and cells were gently washed once with 200 μl PBS. Plates were frozen immediately for a minimum of one hour at −80° C. and then thawed. 200 μl of 1× CyQuant cell lysis buffer supplemented with dye, made according to the manufacturer's instruction, was added immediately to each well and incubated at room temperature for 3-5 minutes. Fluorescence was then measured for each well using a Cytofluor II Fluoresence Multiwell Plate Reader and CytoFluor II software with filters at 480 nm for excitation and 520 nm for emission maxima. Cell proliferation was determined for mean values of duplicate samples as percentages relative to untreated cell samples (=100%). Growth inhibition curves were used to derive $IC_{50}$ values.

TABLE 3

Cell growth inhibition ($IC_{50}$ values (nM))

| Compound | Corresponding formula on page 7, 8 or 9 | MCF7 | PC3 | LNCAP | A2780 |
|---|---|---|---|---|---|
| SAHA | | 483 | nd | 4000 | 595 |
| 9A | (2) | 36.6 | 50 | 252 | 130 |
| 9E | (3) | 117 | 296 | 1189 | 651 |
| 9F | (4) | 1.6 | 0.8 | 6.7 | 3 |
| 10F | (5) | 457 | nd | nd | nd |
| 9B | (6) | 2.9 | nd | nd | nd |
| 9C | (7) | 5.2 | nd | nd | nd | nd = not determined

Activity Assay 7

We analysed the ability of compounds to inhibit the production of TNFα from peripheral blood mononuclear cells (PBMCs). TNF-α immunoassays were carried out using the QUANTIKINE® Human TNF-α assay kit (R&D systems, Abingdon UK) according to the manufacturer's instructions. Human whole blood was separated using Ficol Paque™ Plus (GE Healthcare, Arnersham, UK) and the PBMCs were plated in 24 well plates, at a density of 2.5×10⁶ in 500 μl of cell culture medium per well. Compounds were added 1 hour later in volumes of 100 μl at 6× final concentration. Five hours later lipopolysaccharide (LSP, Sigma, Poole, UK) was added in a volume of 10 μl at 60× final concentration. Plates were mixed and left overnight at 37° C. 5% $CO_2$. Plates were centrifuged and cell supernatant was transferred to a new plate. The QUANTIKINE® assay reagents and standards were prepared according to the manufacturer instructions. The QUANTIKINE® assay plate was prepared by adding 50 μl of assay diluent RD1F into each well. This was followed by 200 μl of standard or 100 μl of calibrator diluent plus 100 μl cell supernatant; this was incubated for 2 hours at room temperature (RT). The plate was washed using wash buffer 4 times. After the final wash the plate was tapped on clean paper towel to remove all residual buffer. 200 μl of TNF-α conjugate was added to each well and incubated for 1 hour at RT. The plate was then washed as before. The required amount of substrate solution was prepared by adding equal volumes of colour reagents A and B, protecting from light, 200 μl of this mix was added to each well and incubated for 20 mins at RT, protected from light. 50 μl of stop solution was added to each well in the same order as the substrate solution and the plate was read on a Biorad 680 96 well plate reader (Bio-Rad, Hemel Hempstead, UK) at 450 nm with λ correction at 570 nm. TNF-α levels were determined for mean values of duplicate samples using absorbance in nm, calibration zero values were subtracted from all results to correct for the addition of calibrator diluent in the assay.

TABLE 4

Inhibition of LPS-induced TNFα secretion from PBMCs

| Compound | Corresponding formula on page 7, 8 or 9 | Concentration (nM) | % inhibition |
|---|---|---|---|
| SAHA | N/A | 200 | 59 |
| 9A | (2) | 200 | 69 |
| 9E | (3) | 200 | 84 |
| 9F | (4) | 7.5 | 68 |

Activity Assay 8

We analysed the ability of compound 9A (the compound of formula (2) on page 7) to inhibit inflammation in mice. Balb/c mice were sensitised by application of 5% (w/v) oxazolone to abdominal shaved skin. After 7 days mice were challenged by topical application of 3% (w/v) oxalazone to the left ear and acetone to the right ear. After 30 minutes test compounds dissolved in acetone were applied to the ears (dorsal and ventral surface). After 24 hours mice were euthanized and the weight of ears determined. % inhibition was determined using the following formula where W equals average weights;

$$\%\text{inhibition} = 1 - ((W^{irritant+test\ material} - W^{vehicle}) \times 100)/(W^{irritant\ alone} - W^{vehicle}))$$

TABLE 5

In vivo inflammation

| Compound | Change in ear weight (mg)$^a$ | % inhibition compared to vehicle |
|---|---|---|
| Vehicle | 63.5 ± 3.8 | N/A |
| 9A (0.1%) | 42.4 ± 4.3 | 33.3 |
| 9A (1%) | 23.5 ± 3.2 | 63.0 |

$^a$Mean ± SD, 8 animals per group.

The invention claimed is:

1. A compound of formula (I) or (I'), or a pharmaceutically acceptable salt thereof,

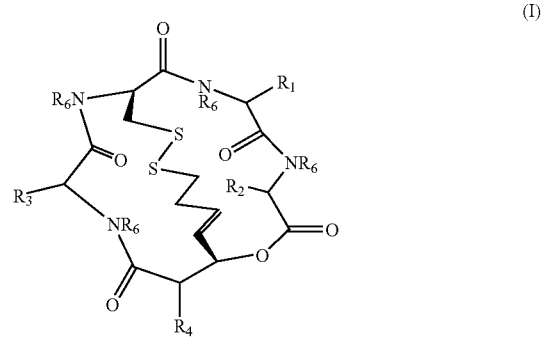

(I)

-continued (1')

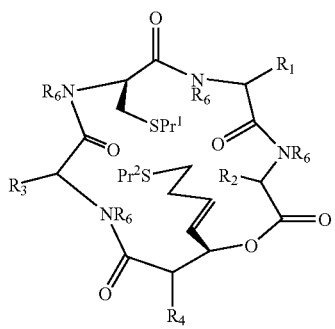

wherein $R_1$, $R_2$, $R_3$ and $R_4$ are the same or different and represent an amino acid side chain moiety, each $R_6$ is the same or different and represents hydrogen or $C_1$-$C_4$ alkyl and $Pr^1$ and $Pr^2$ are the same or different and represent hydrogen or a thiol-protecting group.

2. A pharmaceutical composition comprising a compound according to claim 1, and a pharmaceutically acceptable carrier or diluent.

3. The pharmaceutical composition according to claim 2, which is in a format suitable for oral, rectal, parenteral, intranasal or transdermal administration or administration by inhalation or by suppository.

4. The pharmaceutical composition according to claim 3, which is in the form of a tablet, capsule, troche, lozenge, aqueous or oily suspensions, dispersible powders or granules or a sub-lingual tablet.

5. The compound according to claim 1 wherein each amino acid side chain is a moiety selected from —H, —$C_1$-$C_6$ alkyl, —$C_2$-$C_6$ alkenyl, -L-O—C(O)—R', -L-C(O)—O—R", -L-A, -L-NR"R", -L-Het-C(O)-Het-R" and -L-Het-R", wherein L is a $C_1$-$C_6$ alkylene group, A is phenyl or a 5- to 6-membered heteroaryl group, each R' is the same or different and represents $C_1$-$C_4$ alkyl, each R" is the same or different and represents H or $C_1$-$C_6$ alkyl, each -Het- is the same or different and is a heteroatom spacer selected from —O—, —N(R''')— and —S— and each R''' is the same or different and represents H or $C_1$-$C_4$ alkyl.

6. The compound according to claim 5 wherein A is phenyl.

7. The compound according to claim 5 wherein -Het- is —O— or —N(R''')—.

8. The compound according to claim 1 wherein $R_1$ is a moiety selected from —H and —$C_1$-$C_6$ alkyl.

9. The compound according to claim 1 wherein $R_2$ is a moiety selected from —H and —$C_1$-$C_4$ alkyl.

10. The compound according to claim 1 wherein $R_3$ is a moiety selected from —H, —$C_1$-$C_6$ alkyl, -L-C(O)—O—R", -L-A, -L-NR"R" and -L-N(R")—C(O)—O—R".

11. The compound according to claim 1 wherein $R_4$ is a moiety selected from —H and —$C_1$-$C_4$ alkyl.

12. The compound according to claim 1 wherein $R_6$ is —H.

13. The compound according to claim 1 wherein $Pr^1$ and $Pr^2$ are the same or different and are selected from hydrogen and a protecting group selected from a benzyl group which is optionally substituted by $C_1$-$C_6$alkoxy, $C_1$-$C_6$ acyloxy, hydroxy and nitro, picolyl, picolyl-N-oxide, anthrylmethyl, diphenylmethyl, phenyl, t-butyl, adamanthyl, $C_1$-$C_6$ acyloxymethyl, $C_1$-$C_6$ alkoxymethyl, tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl and $C_1$-$C_6$ alkylcarbamoyl.

14. The compound according to claim 1 wherein $Pr^1$ and $Pr^2$ are hydrogen.

15. The compound according to claim 1 wherein each amino acid side chain is an amino acid side chain moiety present in a natural amino acid or is —$(CH_2)_2$—C(O)—O—C(CH_3)_3$, —$(CH_2)_4$—NH—C(O)—O—C(CH_3)_3$, —$(CH_2)_3$—NH—C(O)NH_2$, —$CH_2$—$CH_2OH$ or —$(CH_2)_2$—$CH_2NH_2$.

16. The compound according to claim 1 wherein the compound is a compound of formula (2), (2'), (3), (3'), (4), (4'), (5), (5'), (6), (6'), (7), (7'), (8), (8'), (9) or (9')

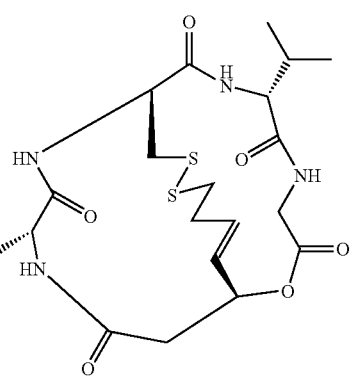

(2)

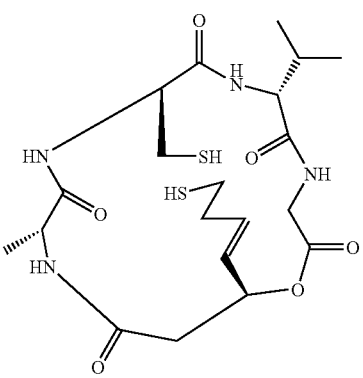

(2')

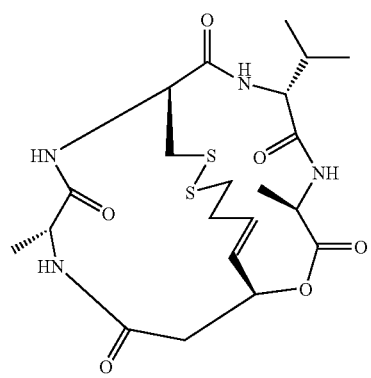

(3)

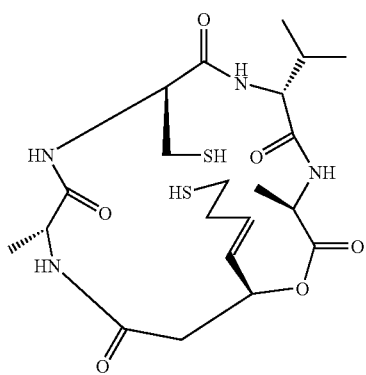
(3')
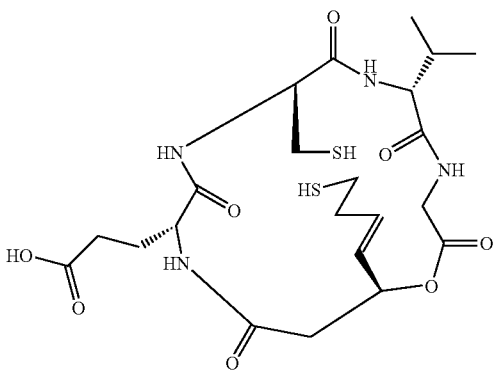
(5')
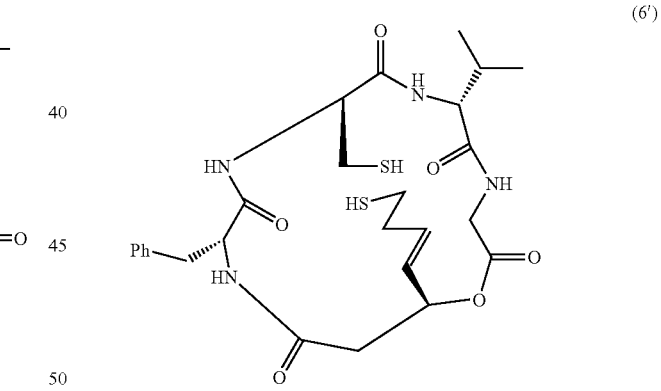
(4)
(6)
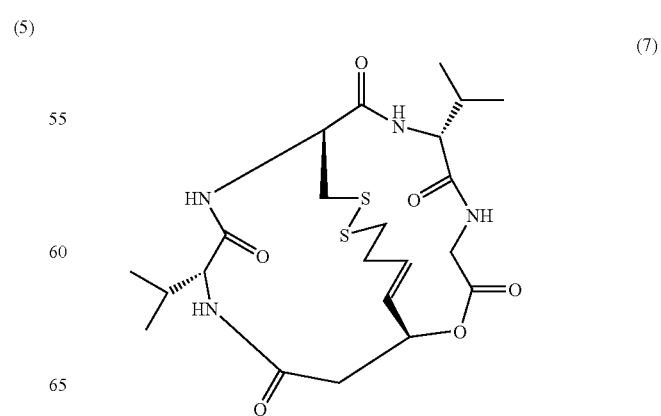
(4')
(6')
(5)
(7)

-continued
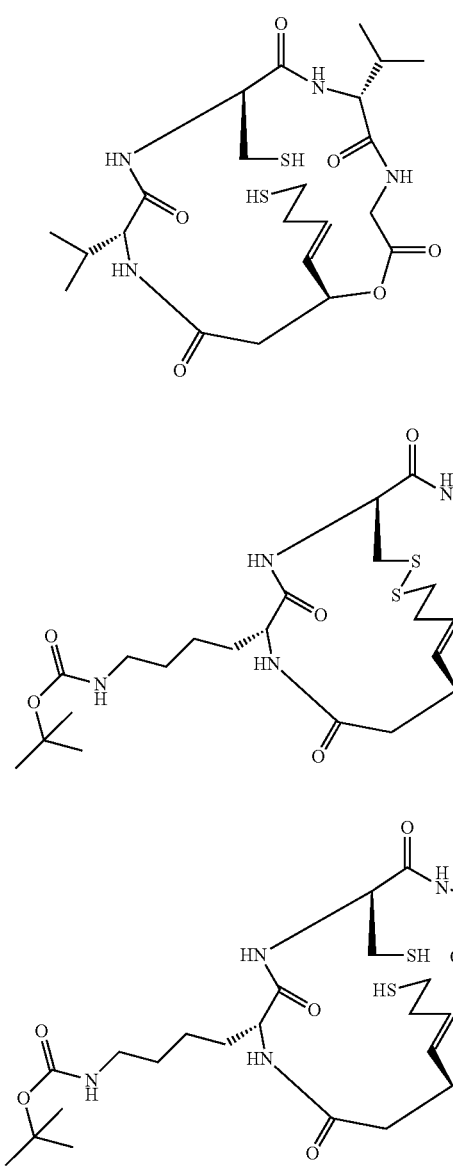
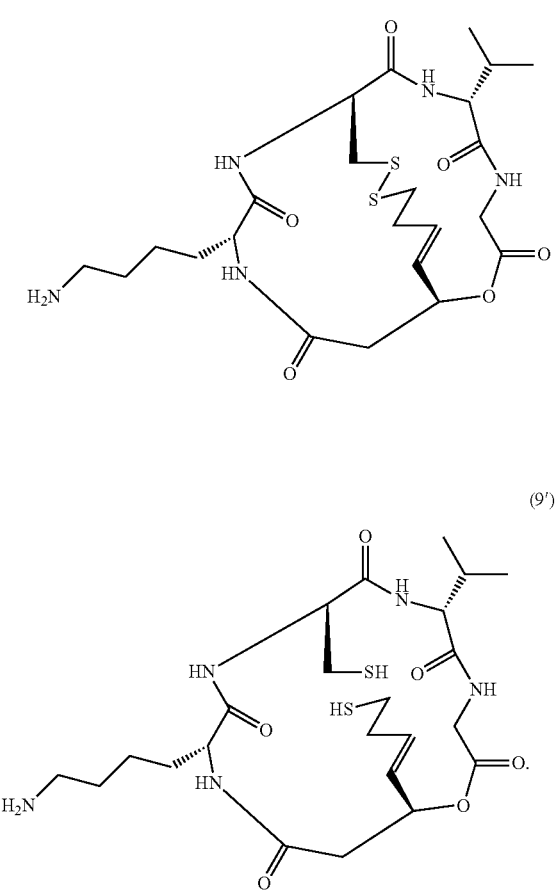
17. The compound according to claim 1 wherein the compound is a compound of formula (I), or a pharmaceutically acceptable salt thereof.
* * * * *